US011933778B2

(12) United States Patent
Wanunu et al.

(10) Patent No.: US 11,933,778 B2
(45) Date of Patent: Mar. 19, 2024

(54) LIPID-FREE ANCHORING OF THERMOPHILIC BACTERIOPHAGE G20C PORTAL ADAPTER INTO SOLID-STATE NANOPORES

(71) Applicants: Northeastern University, Boston, MA (US); University of York, York (GB)

(72) Inventors: Meni Wanunu, Needham, MA (US); Alfred Antson, York (GB); Sandra Greive, York (GB); Benjamin Cressiot, Montlignon (FR)

(73) Assignees: Northeastern University, Boston, MA (US); University of York, York (GB)

( * ) Notice: Subject to any disclaimer, the term of this patent is extended or adjusted under 35 U.S.C. 154(b) by 22 days.

(21) Appl. No.: 17/809,705

(22) Filed: Jun. 29, 2022

(65) Prior Publication Data

US 2022/0373533 A1 Nov. 24, 2022

Related U.S. Application Data

(63) Continuation of application No. 16/416,139, filed on May 17, 2019, now Pat. No. 11,408,880.

(Continued)

(51) Int. Cl.

| | |
|---|---|
| ***G01N 33/487*** | (2006.01) |
| ***B81B 1/00*** | (2006.01) |
| ***B82Y 15/00*** | (2011.01) |
| ***C07K 14/005*** | (2006.01) |
| ***C12Q 1/6869*** | (2018.01) |

(52) U.S. Cl.

CPC ....... *G01N 33/48721* (2013.01); *B81B 1/002* (2013.01); *C07K 14/005* (2013.01); *C12Q 1/6869* (2013.01); *B82Y 15/00* (2013.01); *C12N 2795/00022* (2013.01); *Y10S 930/22* (2013.01)

(58) Field of Classification Search

None

See application file for complete search history.

(56) References Cited

U.S. PATENT DOCUMENTS

| | | | |
|---|---|---|---|
| 11,408,880 | B2 | 8/2022 | Wanunu et al. |
| 2016/0076091 | A1 | 3/2016 | Huber et al. |
| 2019/0360998 | A1 | 11/2019 | Wanunu et al. |

FOREIGN PATENT DOCUMENTS

| | | | |
|---|---|---|---|
| WO | 2009020682 | A2 | 2/2009 |
| WO | 2019/222717 | A2 | 11/2019 |

OTHER PUBLICATIONS

Wanunu, M. et al. Rapid electronic detection of probe-specific microRNAs using thin nanopore sensors. Nature Nanotech 5, 807-814 (2010).

(Continued)

*Primary Examiner* — J. Christopher Ball

(74) *Attorney, Agent, or Firm* — Hamilton, Brook, Smith & Reynolds, P.C.

(57) ABSTRACT

Hybrid nanopores, comprising a protein pore supported within a solid-state membrane, which combine the robust nature of solid-state membranes with the easily tunable and precise engineering of protein nanopores. In an embodiment, a lipid-free hybrid nanopore comprises a water soluble and stable, modified portal protein of the *Thermus thermophilus* bacteriophage G20c, electrokinetically inserted into a larger nanopore in a solid-state membrane. The hybrid pore is stable and easy to fabricate, and exhibits low peripheral leakage, allowing sensing and discrimination among different types of biomolecules.

15 Claims, 14 Drawing Sheets
(14 of 14 Drawing Sheet(s) Filed in Color)
Specification includes a Sequence Listing.

Wild-type

D/N mutant

\-

\+

Related U.S. Application Data

(60) Provisional application No. 62/673,118, filed on May 17, 2018.

(56) References Cited

OTHER PUBLICATIONS

Eric Gouaux, "α-Hemolysin from *Staphylococcus aureus*: An Archetype of B-Barrel, Channel-Forming Toxins," Journal of Structural Biology 121, 110-122 (1998) Article No. SB983959.
Kadima, W. et al. The influence of ionic strength and pH on the aggregation properties of zinc-free insulin studied by static and dynamic laser light scattering. Biopolymers 33, 1643-1657 (1993).
Van Meervelt, V. et al. Real-Time Conformational Changes and Controlled Orientation of Native Proteins Inside a Protein Nanoreactor. J Am Chem Soc 139, 18640-18646 (2017).
Skinner, G. M., van den Hout, M., Broekmans, O., Dekker, C. & Dekker, N. H. Distinguishing single- and double-stranded nucleic acid molecules using solid-state nanopores. Nano Lett 9, 2953-2960 (2009).
Lin, J., Fabian, M., Sonenberg, N. & Meller, A. Nanopore detachment kinetics of poly(A) binding proteins from RNA molecules reveals the critical role of C-terminus interactions. Biophysical Journal 102, 1427-1434 (2012).
Akeson, M., Branton, D., Kasianowicz, J. J., Brandin, E. & Deamer, D. W. Microsecond time-scale discrimination among polycytidylic acid, polyadenylic acid, and polyuridylic acid as homopolymers or as segments within single RNA molecules. Biophysj 77, 3227-3233 (1999).
Larkin, J. et al. Slow DNA transport through nanopores in hafnium oxide membranes. ACS Nano 7, 10121-10128 (2013).
Guo, "Atomic model for the dimeric FO region of mitochondrial ATP synthase," Science. Nov. 1, 20177; 358(6365): 936-940.
Invitation to Pay Additional Fees and Annex of Partial International Search Report for International Application No. PCT/US2019/033006, entitiled: "Lipid-Free Anchoring of Thermophilic Bacteriophage G20c Portal Adapter into Solid-State Nanopores," dated Oct. 9, 2019.
Cressiot et al., "Porphyrin-Assisted Docking of a Thermophage Portal Protein into Lipid Bilayers: Nanopore Engineering and Characterization," ACS Nano, vol. 11, No. 12, Nov. 15, 2017, pp. 11931-11945.
Cressiot et al., "Porphyrin-Assisted Docking of a Thermophage Portal Protein into Lipid Bilayers: Nanopore Engineering and Characterization," Biophysical Journal, vol. 114, No. 3, 2018.
Hall, et al., "Hybrid Pore Formation by Directed Insertion of [alpha]-haemolysin into Solid-state Nanopores," Nature Nanotechnology, Nature Publishing Group, vol. 5, No. 12, Nov. 28, 2010, pp. 874-877.
Hall, et al., "Hybrid Biological/Solid-state Nanopores," Biophysical Journal, vol. 100, No. 3, Mar. 6, 2011, p. 168.
Khan et al., "Electromechanical impedance spectroscopy for black lipid membranes fused with channel protein supported on solid-state nanopore," European Biophysics Journal, vol. 45, No. 8, Aug. 1, 2016, pp. 843-852.
International Search Report and Written Opinion for International Application No. PCT/US2019/033006, entitiled: "Lipid-Free Anchoring of Thermophilic Bacteriophage G20c Portal Adapter into Solid-State Nanopores," dated Dec. 2, 2019.
International Preliminary Search Report and Written Opinion for International Application No. PCT/US2019/033006, entitled "Lipid-Free Anchoring of Thermophilic Bacteriophage G20c Portal Adapter into Solid-State Nanopores," consisting of 11 pages, dated Nov. 17, 2020.
Cressiot, B., et al., "Thermostable virus portal proteins as reprogrammable adapters for solid-state nanopore sensors", Nature communication, vol. 9, No. 1, Nov. 7, 2018, 1 page.
International Search Report and Written Opinion received for PCT Patent Application No. PCT/US2023/067412, dated Sep. 18, 2023, 14 pages.
Wang, H. et al. Determining the Physical Properties of Molecules with Nanometer-Scale Pores. ACS Sensors 3, 251-263 (2018).
Derrington, I. M. et al. Nanopore DNA sequencing with MspA. Proc. Natl. Acad. Sci. U.S.A. 107, 16060-16065 (2010).
Nivala, J., Marks, D. B. & Akeson, M. Unfoldase-mediated protein translocation through an α-hemolysin nanopore. Nat Biotechnol 31, 247-250 (2013).
Rodriguez-Larrea, D. & Bayley, H. Multistep protein unfolding during nanopore translocation. Nature Nanotech 8, 288-295 (2013).
Gu, L. Q., Braha, O., Conlan, S., Cheley, S. & Bayley, H. Stochastic sensing of organic analytes by a pore-forming protein containing a molecular adapter. Nature 398, 686-690 (1999).
Butler, T. Z., Pavlenok, M., Derrington, I. M., Niederweis, M. & Gundlach, J. H. Single-molecule DNA detection with an engineered MspA protein nanopore. Proc. Natl. Acad. Sci. U.S.A. 105, 20647-20652 (2008).
Kasianowicz, J. J. et al. Analytical applications for pore-forming proteins. Biochim Biophys Acta 1858, 593-606 (2016).
Zhang, M. et al. Thermophoresis-Controlled Size-Dependent DNA Translocation through an Array of Nanopores. ACS Nano acsnano. 8b00961 (2018). doi:10.1021/acsnano.8b00961.
Larkin, J., Henley, R. Y., Jadhav, V., Korlach, J. & Wanunu, M. Length-independent DNA packing into nanopore zero-mode waveguides for low-input DNA sequencing. Nat Nano 12, 1169-1175 (2017).
McNally, B. et al. Optical Recognition of Converted DNA Nucleotides for Single-Molecule DNA Sequencing Using Nanopore Arrays. Nano Lett 10, 2237-2244 (2010).
Jain, M. et al. Nanopore sequencing and assembly of a human genome with ultra-long reads. Nature Biotechnology 36, 338-345 (2018).
Jain, M. et al. Improved data analysis for the MinION nanopore sequencer. Nature Methods 12, 351-356 (2015).
Loman, N. J., Quick, J. & Simpson, J. T. A complete bacterial genome assembled de novo using only nanopore sequencing data. Nature Methods 12, 733-735 (2015).
Garalde, D. R. et al. Highly parallel direct RNA sequencing on an array of nanopores. Nature Methods 15, 201-206 (2018).
Howorka, S. & Siwy, Z. Nanopore analytics: sensing of single molecules. Chem. Soc. Rev. 38, 2360 (2009).
Kasianowicz, J. J., Brandin, E., Branton, D. & Deamer, D. W. Characterization of individual polynucleotide molecules using a membrane channel. Proc. Natl. Acad. Sci. U.S.A. 93, 13770-13773 (1996).
Mohammad, M. M. et al. Engineering a rigid protein tunnel for biomolecular detection. J Am Chem Soc 134, 9521-9531 (2012).
Robertson, J. W. F. et al. Single-molecule mass spectrometry in solution using a solitary nanopore. Proc. Natl. Acad. Sci. U.S.A. 104, 8207-8211 (2007).
Merstorf, C. et al. Wild type, mutant protein unfolding and phase transition detected by single-nanopore recording. ACS Chem Biol 7, 652-658 (2012).
Huang, G., Willems, K., Soskine, M., Wloka, C. & Maglia, G. Electro-osmotic capture and ionic discrimination of peptide and protein biomarkers with FraC nanopores. Nature Communications 8, 935 (2017).
Piguet, F. et al. Identification of single amino acid differences in uniformly charged homopolymeric peptides with aerolysin nanopore. Nature Communications 9, (2018).
Luchian, T., Shin, S.-H. & Bayley, H. Kinetics of a three-step reaction observed at the single-molecule level. Angew Chem Int Ed Engl 42, 1926-1929 (2003).
Wescoe, Z. L., Schreiber, J. & Akeson, M. Nanopores discriminate among five C5-cytosine variants in DNA. J Am Chem Soc 136, 16582-16587 (2014).
Baaken, G. et al. High-Resolution Size-Discrimination of Single Nonionic Synthetic Polymers with a Highly Charged Biological Nanopore. ACS Nano 9, 6443-6449 (2015).
Fennouri, A. A. et al. Single molecule detection of glycosaminoglycan hyaluronic acid oligosaccharides and depolymerization enzyme activity using a protein nanopore. ACS Nano 6, 9672-9678 (2012).
Lee, J. et al. Semisynthetic Nanoreactor for Reversible Single-Molecule Covalent Chemistry. ACS Nano 10, 8843-8850 (2016).

(56) References Cited

OTHER PUBLICATIONS

Willems, K., Van Meervelt, V., Wloka, C. & Maglia, G. Single-molecule nanopore enzymology. Philos. Trans. R. Soc. Lond., B, Biol. Sci. 372, (2017).
Rosen, C. B., Rodriguez-Larrea, D. & Bayley, H. Single-molecule site-specific detection of protein phosphorylation with a nanopore. Nat Biotechnol 32, 179-181 (2014).
Verschueren, D. V., Jonsson, M. P. & Dekker, C. Temperature dependence of DNA translocations through solid-state nanopores. Nanotechnology 26, 234004 (2015).
Oukhaled, A. et al. Dynamics of completely unfolded and native proteins through solid-state nanopores as a function of electric driving force. ACS Nano 5, 3628-3638 (2011).
Yamazaki, H. et al. Label-Free Single-Molecule Thermoscopy Using a Laser-Heated Nanopore. Nano Lett 17, 7067-7074 (2017).
Song, L. et al. Structure of staphylococcal alpha-hemolysin, a heptameric transmembrane pore. Science 274, 1859-1866 (1996).
Castell, O. K., Berridge, J. & Wallace, M. I. Quantification of membrane protein inhibition by optical ion flux in a droplet interface bilayer array. Angewandte Chemie International Edition 51, 3134-3138 (2012).
Williams, L. S., Levdikov, V. M., Minakhin, L., Severinov, K. & Antson, A. A. 12-Fold symmetry of the putative portal protein from the Thermus thermophilus bacteriophage G20C determined by X-ray analysis. Acta Crystallogr Sect F Struct Biol Cryst Commun 69, 1239-1241 (2013).
Casjens, S. R. & Gilcrease, E. B. Determining DNA packaging strategy by analysis of the termini of the chromosomes in tailed-bacteriophage virions. Methods Mol Biol 502, 91-111 (2009).
Lebedev, A. A. et al. Structural framework for DNA translocation via the viral portal protein. EMBO J 26, 1984-1994 (2007).
Hoogerheide, D. P., Garaj, S. & Golovchenko, J. A. Probing Surface Charge Fluctuations with Solid-State Nanopores. Physical Review Letters 102, 256804 (2009).
Henrickson, S. E., Misakian, M., Robertson, B. & Kasianowicz, J. J. Driven DNA transport into an asymmetric hanometer-scale pore. Phys Rev Lett 85, 3057-3060 (2000).
Meller, A. & Branton, D. Single molecule measurements of DNA transport through a nanopore. Electrophoresis 23, 2583-2591 (2002).
Japrung, D., Henricus, M., Li, Q., Maglia, G. & Bayley, H. Urea Facilitates the Translocation of Single-Stranded DNA and RNA Through the a-Hemolysin Nanopore. Biophysical Journal 98, 1856-1863 (2010).
Cressiot, B. et al. Dynamics and Energy Contributions for Transport of Unfolded Pertactin through a Protein Nanopore. ACS Nano 9, 9050-9061 (2015).
Pastoriza-Gallego, M. et al. Dynamics of unfolded protein transport through an aerolysin pore. J Am Chem Soc 133, 2923-2931 (2011).
Oukhaled, A., Bacri, L., Pastoriza-Gallego, M., Betton, J.-M. & Pelta, J. Sensing proteins through nanopores: fundamental to applications. ACS Chem Biol 7, 1935-1949 (2012).
Stefureac, R., Long, Y.-T., Kraatz, H.-B., Howard, P. & Lee, J. S. Transport of alpha-helical peptides through alpha-hemolysin and aerolysin pores. Biochemistry 45, 9172-9179 (2006).
Pastoriza-Gallego, M. et al. Evidence of unfolded protein translocation through a protein nanopore. ACS Nano 8, 11350-11360 (2014).
Wang, H.-Y., Ying, Y.-L., Li, Y., Kraatz, H.-B. & Long, Y.-T. Nanopore Analysis of B-Amyloid Peptide Aggregation Transition Induced by Small Molecules. Anal Chem 83, 1746-1752 (2011).
Sutherland, T. C. et al. Structure of peptides investigated by nanopore analysis. Nano Lett 4, 1273-1277 (2004).
Meng, H. et al. Nanopore analysis of tethered peptides. J Pept Sci 16, 701-708 (2010).
Mereuta, L. et al. Slowing down single-molecule trafficking through a protein nanopore reveals intermediates for peptide translocation. Sci Rep 4, 3885-3885 (2014).
Whittingham, J. L., Edwards, D. J., Antson, A. A., Clarkson, J. M. & Dodson, G. G. Interactions of phenol and m-cresol in the insulin hexamer, and their effect on the association properties of B28 pro → Asp insulin analogues. Biochemistry 37, 11516-11523 (1998).

FIG. 11A
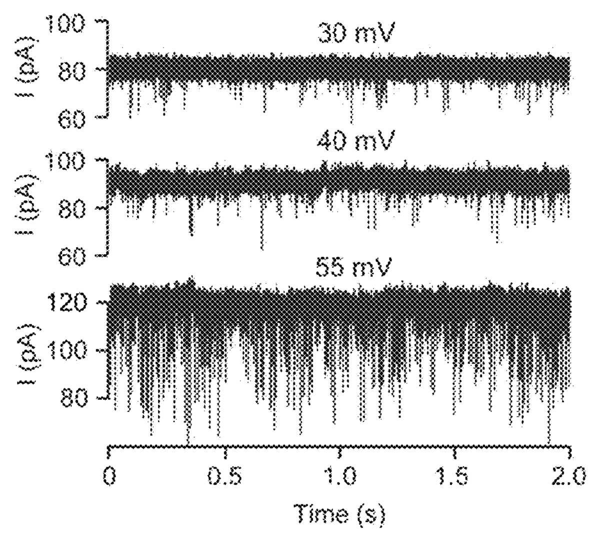
FIG. 11B
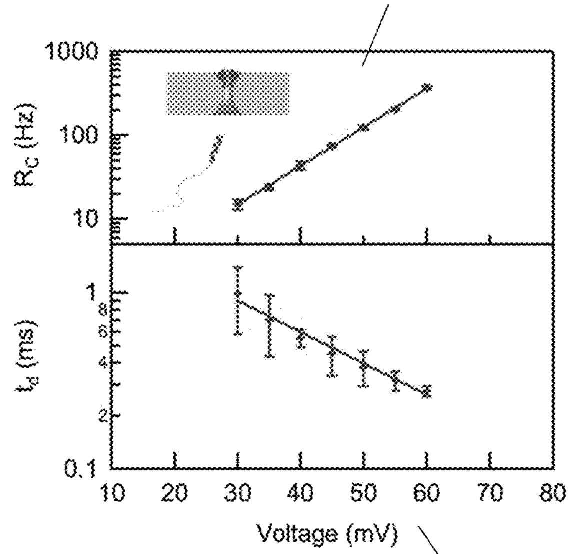
FIG. 11C

FIG. 12B (left)

FIG. 12C (left)

FIG. 12D (left)

SEQUENCE LISTING

<160> NUMBER OF SEQ ID NOS: 41

<210> SEQ ID NO 1
<211> LENGTH: 448
<212> TYPE: PRT
<213> ORGANISM: Thermus Thermophilus Bacteriophage G20C

<400> SEQUENCE: 1

```
Met Ala Lys Arg Gly Arg Lys Pro Lys Glu Leu Val Pro Gly Pro Gly
1               5                   10                  15

Ser Ile Asp Pro Ser Asp Val Pro Lys Leu Glu Gly Ala Ser Val Pro
            20                  25                  30

Val Met Ser Thr Ser Tyr Asp Val Val Val Asp Arg Glu Phe Asp Glu
        35                  40                  45

Leu Leu Gln Gly Lys Asp Gly Leu Leu Val Tyr His Lys Met Leu Ser
    50                  55                  60

Asp Gly Thr Val Lys Asn Ala Leu Asn Tyr Ile Phe Gly Arg Ile Arg
65                  70                  75                  80

Ser Ala Lys Trp Tyr Val Glu Pro Ala Ser Thr Asp Pro Glu Asp Ile
                85                  90                  95

Ala Ile Ala Ala Phe Ile His Ala Gln Leu Gly Ile Asp Asp Ala Ser
            100                 105                 110

Val Gly Lys Tyr Pro Phe Gly Arg Leu Phe Ala Ile Tyr Glu Asn Ala
        115                 120                 125

Tyr Ile Tyr Gly Met Ala Ala Gly Glu Ile Val Leu Thr Leu Gly Ala
    130                 135                 140

Asp Gly Lys Leu Ile Leu Asp Lys Ile Val Pro Ile His Pro Phe Asn
145                 150                 155                 160

Ile Asp Glu Val Leu Tyr Asp Glu Glu Gly Gly Pro Lys Ala Leu Lys
                165                 170                 175

Leu Ser Gly Glu Val Lys Gly Gly Ser Gln Phe Val Ser Gly Leu Glu
            180                 185                 190

Ile Pro Ile Trp Lys Thr Val Val Phe Leu His Asn Asp Asp Gly Ser
        195                 200                 205

Phe Thr Gly Gln Ser Ala Leu Arg Ala Ala Val Pro His Trp Leu Ala
    210                 215                 220

Lys Arg Ala Leu Ile Leu Leu Ile Asn His Gly Leu Glu Arg Phe Met
225                 230                 235                 240

Ile Gly Val Pro Thr Leu Thr Ile Pro Lys Ser Val Arg Gln Gly Thr
                245                 250                 255

Lys Gln Trp Glu Ala Ala Lys Glu Ile Val Lys Asn Phe Val Gln Lys
            260                 265                 270

Pro Arg His Gly Ile Ile Leu Pro Asp Asp Trp Lys Phe Asp Thr Val
        275                 280                 285

Asp Leu Lys Ser Ala Met Pro Asp Ala Ile Pro Tyr Leu Thr Tyr His
    290                 295                 300

Asp Ala Gly Ile Ala Arg Ala Leu Gly Ile Asp Phe Asn Thr Val Gln
305                 310                 315                 320

Leu Asn Met Gly Val Gln Ala Ile Asn Ile Gly Glu Phe Val Ser Leu
                325                 330                 335

Thr Gln Gln Thr Ile Ile Ser Leu Gln Arg Glu Phe Ala Ser Ala Val
            340                 345                 350

Asn Leu Tyr Leu Ile Pro Lys Leu Val Leu Pro Asn Trp Pro Ser Ala
        355                 360                 365
```

```
Thr Arg Phe Pro Arg Leu Thr Phe Glu Met Glu Glu Arg Asn Asp Phe
    370                 375                 380

Ser Ala Ala Ala Asn Leu Met Gly Met Leu Ile Asn Ala Val Lys Asp
385                 390                 395                 400

Ser Glu Asp Ile Pro Thr Glu Leu Lys Ala Leu Ile Asp Ala Leu Pro
                405                 410                 415

Ser Lys Met Arg Arg Ala Leu Gly Val Val Asp Glu Val Arg Glu Ala
            420                 425                 430

Val Arg Gln Pro Ala Asp Ser Arg Tyr Leu Tyr Thr Arg Arg Arg Arg
        435                 440                 445


<210> SEQ ID NO 2
<211> LENGTH: 1347
<212> TYPE: DNA
<213> ORGANISM: Thermus Thermophilus Bacteriophage G20C

<400> SEQUENCE: 2

atggctaagc gaggacgtaa acccaaagag ctggtccccg gacctggctc cattgaccca      60

tctgacgttc ccaagctcga gggcgcctcc gtgccggtga tgtccaccag ttacgacgtg     120

gtggtggacc gggagtttga cgagctactg cagggcaagg acggcttgct cgtctaccac     180

aagatgctct cggacggcac ggttaagaac gccctcaact acatcttcgg acgcatccgc     240

tcggcgaagt ggtacgtaga gcccgcctct accgacccgg aagacatcgc catcgccgcc     300

ttcatccacg cccagttagg catagacgac gcttcggtgg gcaagtatcc ctttggccgc     360

cttttcgcca tctacgaaaa cgcctacata tacggcatgg ccgccgggga aatcgtacta     420

acccttggcg cggacggcaa gctcatcctt gacaaaatcg tccctatcca ccctttcaac     480

attgacgagg tgctttacga cgaggaaggc ggtccaaagg cgctaaagct aagcggagag     540

gtgaagggcg gaagccagtt tgtgagcggg ttggagattc ctatatggaa gaccgtggtc     600

ttcctgcaca acgacgacgg ctccttcacc ggacagagcg ccctcagagc cgccgtgccg     660

cattggctag ccaaacgagc cctcattctc ctcatcaacc acgggttgga gcgcttcatg     720

attggcgtgc ccaccctcac catccccaag agcgtgcgtc agggaaccaa gcaatgggag     780

gccgccaagg aaatcgtcaa gaactttgtt caaaaaccac ggcatggtat aatactgcct     840

gacgactgga agtttgacac ggtagacctg aagtcggcca tgcccgacgc cattccctac     900

ctgacctacc acgacgcggg catcgctagg gcgcttggca tagacttcaa caccgttcaa     960

ctaaacatgg gggtacaggc gataaacatc ggcgagttcg taagcctgac ccagcagacc    1020

atcatttcgc tccagcggga gttcgctagc gcggtcaacc tctacctcat ccccaagcta    1080

gtgcttccca actggccgag cgctactcgc tttcctaggc tcacctttga gatggaggag    1140

cgcaacgact tctccgccgc ggccaacctt atgggcatgc tcatcaacgc ggttaaggac    1200

tccgaagaca ttcccaccga gctcaaggcg ctaatagacg ctctgcctag caagatgcgc    1260

cgggcgcttg gcgtggtgga cgaggtgagg gaagcggtac gccaacccgc cgattcccgc    1320

tacctgtaca cgcgaaggag gaggtag                                        1347


<210> SEQ ID NO 3
<211> LENGTH: 446
<212> TYPE: PRT
<213> ORGANISM: Thermus Thermophilus Bacteriophage G20C
```

<400> SEQUENCE: 3

```
Met Ala Lys Arg Gly Arg Lys Pro Lys Glu Leu Val Pro Gly Pro Gly
1               5                   10                  15

Ser Ile Asp Pro Ser Asp Val Pro Lys Leu Glu Gly Ala Ser Val Pro
            20                  25                  30

Val Met Ser Thr Ser Tyr Asp Val Val Val Asp Arg Glu Phe Asp Glu
        35                  40                  45

Leu Leu Gln Gly Lys Asp Gly Leu Leu Val Tyr His Lys Met Leu Ser
    50                  55                  60

Asp Gly Thr Val Lys Asn Ala Leu Asn Tyr Ile Phe Gly Arg Ile Arg
65                  70                  75                  80

Ser Ala Lys Trp Tyr Val Glu Pro Ala Ser Thr Asp Pro Glu Asp Ile
                85                  90                  95

Ala Ile Ala Ala Phe Ile His Ala Gln Leu Gly Ile Asp Asp Ala Ser
            100                 105                 110

Val Gly Lys Tyr Pro Phe Gly Arg Leu Phe Ala Ile Tyr Glu Asn Ala
        115                 120                 125

Tyr Ile Tyr Gly Met Ala Ala Gly Glu Ile Val Leu Thr Leu Gly Ala
    130                 135                 140

Asp Gly Lys Leu Ile Leu Asp Lys Ile Val Pro Ile His Pro Phe Asn
145                 150                 155                 160

Ile Asp Glu Val Leu Tyr Asp Glu Glu Gly Gly Pro Lys Ala Leu Lys
                165                 170                 175

Leu Ser Gly Glu Val Lys Gly Gly Ser Gln Phe Val Ser Gly Leu Glu
            180                 185                 190

Ile Pro Ile Trp Lys Thr Val Val Phe Leu His Asn Asp Asp Gly Ser
        195                 200                 205

Phe Thr Gly Gln Ser Ala Leu Arg Ala Ala Val Pro His Trp Leu Ala
    210                 215                 220

Lys Arg Ala Leu Ile Leu Leu Ile Asn His Gly Leu Glu Arg Phe Met
225                 230                 235                 240

Ile Gly Val Pro Thr Leu Thr Ile Pro Lys Ser Val Arg Gln Gly Thr
                245                 250                 255

Lys Gln Trp Glu Ala Ala Lys Glu Ile Val Lys Asn Phe Val Gln Lys
            260                 265                 270

Pro Arg His Gly Ile Ile Leu Pro Asp Asp Trp Lys Phe Asp Thr Val
        275                 280                 285

Asp Leu Lys Ser Ala Met Pro Asp Ala Ile Pro Tyr Leu Thr Tyr His
    290                 295                 300

Asp Ala Gly Ile Ala Arg Ala Leu Gly Ile Asp Phe Asn Thr Val Gln
305                 310                 315                 320

Leu Asn Met Gly Val Gln Ala Ile Asn Ile Gly Glu Phe Val Ser Leu
                325                 330                 335

Thr Gln Gln Thr Ile Ile Ser Leu Gln Arg Glu Phe Ala Ser Ala Val
            340                 345                 350

Asn Leu Tyr Leu Ile Pro Lys Leu Val Leu Pro Asn Trp Pro Ser Ala
        355                 360                 365

Thr Arg Phe Pro Arg Leu Thr Phe Glu Met Glu Glu Arg Asn Asp Phe
    370                 375                 380

Ser Ala Ala Ala Asn Leu Met Gly Met Leu Ile Asn Ala Val Lys Asp
385                 390                 395                 400

Ser Glu Asp Ile Pro Thr Glu Leu Lys Ala Leu Ile Asp Ala Leu Pro
                405                 410                 415
```

```
Ser Lys Met Arg Arg Ala Leu Gly Val Val Asp Glu Val Arg Glu Ala
            420                 425                 430

Val Arg Gln Pro Ala Asp Leu Glu His His His His His His
        435                 440                 445


<210> SEQ ID NO 4
<211> LENGTH: 1341
<212> TYPE: DNA
<213> ORGANISM: Artificial Sequence
<220> FEATURE:
<223> OTHER INFORMATION: Thermus Thermophilus Bacteriophage G20C and
      Affinity Tag; WT 1-438 C-term

<400> SEQUENCE: 4

atggctaagc gaggacgtaa acccaaagag ctggtccccg gacctggctc cattgaccca     60

tctgacgttc ccaagctcga gggcgcctcc gtgccggtga tgtccaccag ttacgacgtg    120

gtggtggacc gggagtttga cgagctactg cagggcaagg acggcttgct cgtctaccac    180

aagatgctct cggacggcac ggttaagaac gccctcaact acatcttcgg acgcatccgc    240

tcggcgaagt ggtacgtaga gcccgcctct accgacccgg aagacatcgc catcgccgcc    300

ttcatccacg cccagttagg catagacgac gcttcggtgg gcaagtatcc ctttggccgc    360

cttttcgcca tctacgaaaa cgcctacata tacggcatgg ccgccgggga aatcgtacta    420

acccttggcg cggacggcaa gctcatcctt gacaaaatcg tccctatcca ccctttcaac    480

attgacgagg tgctttacga cgaggaaggc ggtccaaagg cgctaaagct aagcggagag    540

gtgaagggcg gaagccagtt tgtgagcggg ttggagattc ctatatggaa gaccgtggtc    600

ttcctgcaca acgacgacgg ctccttcacc ggacagagcg ccctcagagc cgccgtgccg    660

cattggctag ccaaacgagc cctcattctc ctcatcaacc acgggttgga gcgcttcatg    720

attggcgtgc ccaccctcac catccccaag agcgtgcgtc agggaaccaa gcaatgggag    780

gccgccaagg aaatcgtcaa gaactttgtt caaaaaccac ggcatggtat aatactgcct    840

gacgactgga agtttgacac ggtagacctg aagtcggcca tgcccgacgc cattccctac    900

ctgacctacc acgacgcggg catcgctagg gcgcttggca tagacttcaa caccgttcaa    960

ctaaacatgg gggtacaggc gataaacatc ggcgagttcg taagcctgac ccagcagacc   1020

atcatttcgc tccagcggga gttcgctagc gcggtcaacc tctacctcat ccccaagcta   1080

gtgcttccca actggccgag cgctactcgc tttcctaggc tcacctttga gatggaggag   1140

cgcaacgact tctccgccgc ggccaacctt atgggcatgc tcatcaacgc ggttaaggac   1200

tccgaagaca ttcccaccga gctcaaggcg ctaatagacg ctctgcctag caagatgcgc   1260

cgggcgcttg gcgtggtgga cgaggtgagg gaagcggtac gccaacccgc cgatctcgag   1320

caccaccacc accaccacta g                                             1341


<210> SEQ ID NO 5
<211> LENGTH: 441
<212> TYPE: PRT
<213> ORGANISM: Thermus Thermophilus Bacteriophage G20C

<400> SEQUENCE: 5

Gly Pro Ala Met Ala Lys Arg Gly Arg Lys Pro Lys Glu Leu Val Pro
1               5                   10                  15

Gly Pro Gly Ser Ile Asp Pro Ser Asp Val Pro Lys Leu Glu Gly Ala
            20                  25                  30

Ser Val Pro Val Met Ser Thr Ser Tyr Asp Val Val Val Asp Arg Glu
        35                  40                  45
```

```
Phe Asp Glu Leu Leu Gln Gly Lys Asp Gly Leu Leu Val Tyr His Lys
    50                  55                  60

Met Leu Ser Asp Gly Thr Val Lys Asn Ala Leu Asn Tyr Ile Phe Gly
65                  70                  75                  80

Arg Ile Arg Ser Ala Lys Trp Tyr Val Glu Pro Ala Ser Thr Asp Pro
                85                  90                  95

Glu Asp Ile Ala Ile Ala Ala Phe Ile His Ala Gln Leu Gly Ile Asp
            100                 105                 110

Asp Ala Ser Val Gly Lys Tyr Pro Phe Gly Arg Leu Phe Ala Ile Tyr
        115                 120                 125

Glu Asn Ala Tyr Ile Tyr Gly Met Ala Ala Gly Glu Ile Val Leu Thr
    130                 135                 140

Leu Gly Ala Asp Gly Lys Leu Ile Leu Asp Lys Ile Val Pro Ile His
145                 150                 155                 160

Pro Phe Asn Ile Asp Glu Val Leu Tyr Asp Glu Glu Gly Gly Pro Lys
                165                 170                 175

Ala Leu Lys Leu Ser Gly Glu Val Lys Gly Gly Ser Gln Phe Val Ser
            180                 185                 190

Gly Leu Glu Ile Pro Ile Trp Lys Thr Val Val Phe Leu His Asn Asp
        195                 200                 205

Asp Gly Ser Phe Thr Gly Gln Ser Ala Leu Arg Ala Ala Val Pro His
    210                 215                 220

Trp Leu Ala Lys Arg Ala Leu Ile Leu Leu Ile Asn His Gly Leu Glu
225                 230                 235                 240

Arg Phe Met Ile Gly Val Pro Thr Leu Thr Ile Pro Lys Ser Val Arg
                245                 250                 255

Gln Gly Thr Lys Gln Trp Glu Ala Ala Lys Glu Ile Val Lys Asn Phe
            260                 265                 270

Val Gln Lys Pro Arg His Gly Ile Ile Leu Pro Asp Asp Trp Lys Phe
        275                 280                 285

Asp Thr Val Asp Leu Lys Ser Ala Met Pro Asp Ala Ile Pro Tyr Leu
    290                 295                 300

Thr Tyr His Asp Ala Gly Ile Ala Arg Ala Leu Gly Ile Asp Phe Asn
305                 310                 315                 320

Thr Val Gln Leu Asn Met Gly Val Gln Ala Ile Asn Ile Gly Glu Phe
                325                 330                 335

Val Ser Leu Thr Gln Gln Thr Ile Ile Ser Leu Gln Arg Glu Phe Ala
            340                 345                 350

Ser Ala Val Asn Leu Tyr Leu Ile Pro Lys Leu Val Leu Pro Asn Trp
        355                 360                 365

Pro Ser Ala Thr Arg Phe Pro Arg Leu Thr Phe Glu Met Glu Glu Arg
    370                 375                 380

Asn Asp Phe Ser Ala Ala Ala Asn Leu Met Gly Met Leu Ile Asn Ala
385                 390                 395                 400

Val Lys Asp Ser Glu Asp Ile Pro Thr Glu Leu Lys Ala Leu Ile Asp
                405                 410                 415

Ala Leu Pro Ser Lys Met Arg Arg Ala Leu Gly Val Val Asp Glu Val
            420                 425                 430

Arg Glu Ala Val Arg Gln Pro Ala Asp
        435                 440
```

<210> SEQ ID NO 6
<211> LENGTH: 1383
<212> TYPE: DNA

```
<213> ORGANISM: Artificial Sequence
<220> FEATURE:
<223> OTHER INFORMATION: Thermus Thermophilus Bacteriophage G20C and
      Affinity Tag; WT 1-438 3C prot

<400> SEQUENCE: 6

atgggcagca gccatcatca tcatcatcac agcagcggcc tggaagttct gttccaggga      60

ccagcaatgg ctaagcgagg acgtaaaccc aaagagctgg tccccggacc tggctccatt     120

gacccatctg acgttcccaa gctcgagggc gcctccgtgc cggtgatgtc caccagttac     180

gacgtggtgg tggaccggga gtttgacgag ctactgcagg gcaaggacgg cttgctcgtc     240

taccacaaga tgctctcgga cggcacggtt aagaacgccc tcaactacat cttcggacgc     300

atccgctcgg cgaagtggta cgtagagccc gcctctaccg acccggaaga catcgccatc     360

gccgccttca tccacgccca gttaggcata gacgacgctt cggtgggcaa gtatcccttt     420

ggccgccttt tcgccatcta cgaaaacgcc tacatatacg gcatggccgc cggggaaatc     480

gtactaaccc ttggcgcgga cggcaagctc atccttgaca aatcgtccc tatccaccct      540

ttcaacattg acgaggtgct ttacgacgag gaaggcggtc caaaggcgct aaagctaagc     600

ggagaggtga agggcggaag ccagtttgtg agcgggttgg agattcctat atggaagacc     660

gtggtcttcc tgcacaacga cgacggctcc ttcaccggac agagcgccct cagagccgcc     720

gtgccgcatt ggctagccaa acgagccctc attctcctca tcaaccacgg gttggagcgc     780

ttcatgattg gcgtgcccac cctcaccatc cccaagagcg tgcgtcaggg aaccaagcaa     840

tgggaggccg ccaaggaaat cgtcaagaac tttgttcaaa aaccacggca tggtataata     900

ctgcctgacg actggaagtt tgacacggta gacctgaagt cggccatgcc cgacgccatt     960

ccctacctga cctaccacga cgcgggcatc gctagggcgc ttggcataga cttcaacacc    1020

gttcaactaa acatgggggt acaggcgata aacatcggcg agttcgtaag cctgacccag    1080

cagaccatca tttcgctcca gcgggagttc gctagcgcgg tcaacctcta cctcatcccc    1140

aagctagtgc ttcccaactg gccgagcgct actcgctttc ctaggctcac ctttgagatg    1200

gaggagcgca acgacttctc cgccgcggcc aaccttatgg gcatgctcat caacgcggtt    1260

aaggactccg aagacattcc caccgagctc aaggcgctaa tagacgctct gcctagcaag    1320

atgcgccggg cgcttggcgt ggtggacgag gtgagggaag cggtacgcca acccgccgat    1380

taa                                                                  1383


<210> SEQ ID NO 7
<211> LENGTH: 417
<212> TYPE: PRT
<213> ORGANISM: Thermus Thermophilus Bacteriophage G20C

<400> SEQUENCE: 7

Gly Pro Ala Lys Leu Glu Gly Ala Ser Val Pro Val Met Ser Thr Ser
1               5                   10                  15

Tyr Asp Val Val Val Asp Arg Glu Phe Asp Glu Leu Leu Gln Gly Lys
            20                  25                  30

Asp Gly Leu Leu Val Tyr His Lys Met Leu Ser Asp Gly Thr Val Lys
        35                  40                  45

Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80
```

```
Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125

Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160

Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205

Leu Leu Ile Asn His Gly Leu Glu Arg Phe Met Ile Gly Val Pro Thr
    210                 215                 220

Leu Thr Ile Pro Lys Ser Val Arg Gln Gly Thr Lys Gln Trp Glu Ala
225                 230                 235                 240

Ala Lys Glu Ile Val Lys Asn Phe Val Gln Lys Pro Arg His Gly Ile
                245                 250                 255

Ile Leu Pro Asp Asp Trp Lys Phe Asp Thr Val Asp Leu Lys Ser Ala
            260                 265                 270

Met Pro Asp Ala Ile Pro Tyr Leu Thr Tyr His Asp Ala Gly Ile Ala
        275                 280                 285

Arg Ala Leu Gly Ile Asp Phe Asn Thr Val Gln Leu Asn Met Gly Val
    290                 295                 300

Gln Ala Ile Asn Ile Gly Glu Phe Val Ser Leu Thr Gln Gln Thr Ile
305                 310                 315                 320

Ile Ser Leu Gln Arg Glu Phe Ala Ser Ala Val Asn Leu Tyr Leu Ile
                325                 330                 335

Pro Lys Leu Val Leu Pro Asn Trp Pro Ser Ala Thr Arg Phe Pro Arg
            340                 345                 350

Leu Thr Phe Glu Met Glu Glu Arg Asn Asp Phe Ser Ala Ala Ala Asn
        355                 360                 365

Leu Met Gly Met Leu Ile Asn Ala Val Lys Asp Ser Glu Asp Ile Pro
    370                 375                 380

Thr Glu Leu Lys Ala Leu Ile Asp Ala Leu Pro Ser Lys Met Arg Arg
385                 390                 395                 400

Ala Leu Gly Val Val Asp Glu Val Arg Glu Ala Val Arg Gln Pro Ala
                405                 410                 415

Asp


<210> SEQ ID NO 8
<211> LENGTH: 1311
<212> TYPE: DNA
<213> ORGANISM: Artificial Sequence
<220> FEATURE:
<223> OTHER INFORMATION: Thermus Thermophilus Bacteriophage G20C and
      Affinity Tag; WT Nanopore

<400> SEQUENCE: 8

atgggcagca gccatcatca tcatcatcac agcagcggcc tggaagttct gttccaggga     60

ccagcaaagc tcgagggcgc ctccgtgccg gtgatgtcca ccagttacga cgtggtggtg    120
```

```
gaccgggagt ttgacgagct actgcagggc aaggacggct tgctcgtcta ccacaagatg    180

ctctcggacg gcacggttaa gaacgccctc aactacatct tcggacgcat ccgctcggcg    240

aagtggtacg tagagcccgc ctctaccgac ccggaagaca tcgccatcgc cgccttcatc    300

cacgcccagt taggcataga cgacgcttcg gtgggcaagt atccctttgg ccgccttttc    360

gccatctacg aaaacgccta catatacggc atggccgccg gggaaatcgt actaaccctt    420

ggcgcggacg gcaagctcat ccttgacaaa atcgtcccta tccacccttt caacattgac    480

gaggtgcttt acgacgagga aggcggtcca aaggcgctaa agctaagcgg agaggtgaag    540

ggcggaagcc agtttgtgag cgggttggag attcctatat ggaagaccgt ggtcttcctg    600

cacaacgacg acggctcctt caccggacag agcgccctca gagccgccgt gccgcattgg    660

ctagccaaac gagccctcat tctcctcatc aaccacgggt tggagcgctt catgattggc    720

gtgcccaccc tcaccatccc caagagcgtg cgtcagggaa ccaagcaatg ggaggccgcc    780

aaggaaatcg tcaagaactt tgttcaaaaa ccacggcatg gtataatact gcctgacgac    840

tggaagtttg acacggtaga cctgaagtcg gccatgcccg acgccattcc ctacctgacc    900

taccacgacg cgggcatcgc tagggcgctt ggcatagact tcaacaccgt tcaactaaac    960

atgggggtac aggcgataaa catcggcgag ttcgtaagcc tgacccagca gaccatcatt   1020

tcgctccagc gggagttcgc tagcgcggtc aacctctacc tcatccccaa gctagtgctt   1080

cccaactggc cgagcgctac tcgctttcct aggctcacct ttgagatgga ggagcgcaac   1140

gacttctccg ccgcggccaa ccttatgggc atgctcatca acgcggttaa ggactccgaa   1200

gacattccca ccgagctcaa ggcgctaata gacgctctgc ctagcaagat gcgccgggcg   1260

cttggcgtgg tggacgaggt gagggaagcg gtacgccaac ccgccgatta a             1311
```

```
<210> SEQ ID NO 9
<211> LENGTH: 417
<212> TYPE: PRT
<213> ORGANISM: Artificial Sequence
<220> FEATURE:
<223> OTHER INFORMATION: L230E

<400> SEQUENCE: 9

Gly Pro Ala Lys Leu Glu Gly Ala Ser Val Pro Val Met Ser Thr Ser
1               5                   10                  15

Tyr Asp Val Val Val Asp Arg Glu Phe Asp Glu Leu Leu Gln Gly Lys
            20                  25                  30

Asp Gly Leu Leu Val Tyr His Lys Met Leu Ser Asp Gly Thr Val Lys
        35                  40                  45

Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80

Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125

Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160
```

```
Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205

Glu Leu Ile Asn His Gly Leu Glu Arg Phe Met Ile Gly Val Pro Thr
    210                 215                 220

Leu Thr Ile Pro Lys Ser Val Arg Gln Gly Thr Lys Gln Trp Glu Ala
225                 230                 235                 240

Ala Lys Glu Ile Val Lys Asn Phe Val Gln Lys Pro Arg His Gly Ile
                245                 250                 255

Ile Leu Pro Asp Asp Trp Lys Phe Asp Thr Val Asp Leu Lys Ser Ala
            260                 265                 270

Met Pro Asp Ala Ile Pro Tyr Leu Thr Tyr His Asp Ala Gly Ile Ala
        275                 280                 285

Arg Ala Leu Gly Ile Asp Phe Asn Thr Val Gln Leu Asn Met Gly Val
    290                 295                 300

Gln Ala Ile Asn Ile Gly Glu Phe Val Ser Leu Thr Gln Gln Thr Ile
305                 310                 315                 320

Ile Ser Leu Gln Arg Glu Phe Ala Ser Ala Val Asn Leu Tyr Leu Ile
                325                 330                 335

Pro Lys Leu Val Leu Pro Asn Trp Pro Ser Ala Thr Arg Phe Pro Arg
            340                 345                 350

Leu Thr Phe Glu Met Glu Glu Arg Asn Asp Phe Ser Ala Ala Ala Asn
        355                 360                 365

Leu Met Gly Met Leu Ile Asn Ala Val Lys Asp Ser Glu Asp Ile Pro
    370                 375                 380

Thr Glu Leu Lys Ala Leu Ile Asp Ala Leu Pro Ser Lys Met Arg Arg
385                 390                 395                 400

Ala Leu Gly Val Val Asp Glu Val Arg Glu Ala Val Arg Gln Pro Ala
                405                 410                 415

Asp
```

<210> SEQ ID NO 10
<211> LENGTH: 1311
<212> TYPE: DNA
<213> ORGANISM: Artificial Sequence
<220> FEATURE:
<223> OTHER INFORMATION: L230E

<400> SEQUENCE: 10

```
atgggcagca gccatcatca tcatcatcac agcagcggcc tggaagttct gttccaggga      60

ccagcaaagc tcgagggcgc ctccgtgccg gtgatgtcca ccagttacga cgtggtggtg     120

gaccgggagt ttgacgagct actgcagggc aaggacggct tgctcgtcta ccacaagatg     180

ctctcggacg gcacggttaa gaacgccctc aactacatct tcggacgcat ccgctcggcg     240

aagtggtacg tagagcccgc ctctaccgac ccggaagaca tcgccatcgc cgccttcatc     300

cacgcccagt taggcataga cgacgcttcg gtgggcaagt atccctttgg ccgccttttc     360

gccatctacg aaaacgccta catatacggc atggccgccg gggaaatcgt actaaccctt     420

ggcgcggacg gcaagctcat ccttgacaaa atcgtcccta tccacccttt caacattgac     480

gaggtgcttt acgacgagga aggcggtcca aaggcgctaa agctaagcgg agaggtgaag     540

ggcggaagcc agtttgtgag cgggttggag attcctatat ggaagaccgt ggtcttcctg     600
```

```
cacaacgacg acggctcctt caccggacag agcgccctca gagccgccgt gccgcattgg    660

ctagccaaac gagccctcat tgagctcatc aaccacgggt tggagcgctt catgattggc    720

gtgcccaccc tcaccatccc caagagcgtg cgtcagggaa ccaagcaatg ggaggccgcc    780

aaggaaatcg tcaagaactt tgttcaaaaa ccacggcatg gtataatact gcctgacgac    840

tggaagtttg acacggtaga cctgaagtcg gccatgcccg acgccattcc ctacctgacc    900

taccacgacg cgggcatcgc tagggcgctt ggcatagact tcaacaccgt tcaactaaac    960

atgggggtac aggcgataaa catcggcgag ttcgtaagcc tgacccagca gaccatcatt   1020

tcgctccagc gggagttcgc tagcgcggtc aacctctacc tcatccccaa gctagtgctt   1080

cccaactggc cgagcgctac tcgctttcct aggctcacct ttgagatgga ggagcgcaac   1140

gacttctccg ccgcggccaa ccttatgggc atgctcatca acgcggttaa ggactccgaa   1200

gacattccca ccgagctcaa ggcgctaata gacgctctgc ctagcaagat gcgccgggcg   1260

cttggcgtgg tggacgaggt gagggaagcg gtacgccaac ccgccgatta a             1311


<210> SEQ ID NO 11
<211> LENGTH: 417
<212> TYPE: PRT
<213> ORGANISM: Artificial Sequence
<220> FEATURE:
<223> OTHER INFORMATION: 49C
<220> FEATURE:
<221> NAME/KEY: VARIANT
<222> LOCATION: 251
<223> OTHER INFORMATION: Xaa = Any Amino Acid

<400> SEQUENCE: 11

Gly Pro Ala Lys Leu Glu Gly Ala Ser Val Pro Val Met Ser Thr Ser
1               5                   10                  15

Tyr Asp Val Val Val Asp Arg Glu Phe Asp Glu Cys Leu Gln Gly Lys
            20                  25                  30

Asp Gly Leu Leu Val Tyr His Lys Met Leu Ser Asp Gly Thr Val Lys
        35                  40                  45

Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80

Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125

Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160

Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205

Leu Leu Ile Asn His Gly Leu Glu Arg Phe Met Ile Gly Val Pro Thr
    210                 215                 220
```

```
Leu Thr Ile Pro Lys Ser Val Arg Gln Gly Thr Lys Gln Trp Glu Ala
225                 230                 235                 240

Ala Lys Glu Ile Val Lys Asn Phe Val Gln Xaa Pro Arg His Gly Ile
                245                 250                 255

Ile Leu Pro Asp Asp Trp Lys Phe Asp Thr Val Asp Leu Lys Ser Ala
            260                 265                 270

Met Pro Asp Ala Ile Pro Tyr Leu Thr Tyr His Asp Ala Gly Ile Ala
        275                 280                 285

Arg Ala Leu Gly Ile Asp Phe Asn Thr Val Gln Leu Asn Met Gly Val
    290                 295                 300

Gln Ala Ile Asn Ile Gly Glu Phe Val Ser Leu Thr Gln Gln Thr Ile
305                 310                 315                 320

Ile Ser Leu Gln Arg Glu Phe Ala Ser Ala Val Asn Leu Tyr Leu Ile
                325                 330                 335

Pro Lys Leu Val Leu Pro Asn Trp Pro Ser Ala Thr Arg Phe Pro Arg
            340                 345                 350

Leu Thr Phe Glu Met Glu Glu Arg Asn Asp Phe Ser Ala Ala Ala Asn
        355                 360                 365

Leu Met Gly Met Leu Ile Asn Ala Val Lys Asp Ser Glu Asp Ile Pro
    370                 375                 380

Thr Glu Leu Lys Ala Leu Ile Asp Ala Leu Pro Ser Lys Met Arg Arg
385                 390                 395                 400

Ala Leu Gly Val Val Asp Glu Val Arg Glu Ala Val Arg Gln Pro Ala
                405                 410                 415

Asp


<210> SEQ ID NO 12
<211> LENGTH: 1311
<212> TYPE: DNA
<213> ORGANISM: Artificial Sequence
<220> FEATURE:
<223> OTHER INFORMATION: 49C
<220> FEATURE:
<221> NAME/KEY: misc_feature
<222> LOCATION: 810
<223> OTHER INFORMATION: n = A,T,C or G

<400> SEQUENCE: 12

atgggcagca gccatcatca tcatcatcac agcagcggcc tggaagttct gttccaggga      60

ccagcaaagc tcgagggcgc ctccgtgccg gtgatgtcca ccagttacga cgtggtggtg     120

gaccgggagt ttgacgagtg tctgcagggc aaggacggct tgctcgtcta ccacaagatg     180

ctctcggacg gcacggttaa gaacgccctc aactacatct tcggacgcat ccgctcggcg     240

aagtggtacg tagagcccgc ctctaccgac ccggaagaca tcgccatcgc cgccttcatc     300

cacgcccagt taggcataga cgacgcttcg gtgggcaagt atccctttgg ccgccttttc     360

gccatctacg aaaacgccta catatacggc atggccgccg gggaaatcgt actaaccctt     420

ggcgcggacg gcaagctcat ccttgacaaa atcgtcccta tccacccttt caacattgac     480

gaggtgcttt acgacgagga aggcggtcca aaggcgctaa agctaagcgg agaggtgaag     540

ggcggaagcc agtttgtgag cgggttggag attcctatat ggaagaccgt ggtcttcctg     600

cacaacgacg acggctcctt caccggacag agcgccctca gagccgccgt gccgcattgg     660

ctagccaaac gagccctcat tctcctcatc aaccacgggt tggagcgctt catgattggc     720

gtgcccaccc tcaccatccc caagagcgtg cgtcagggaa ccaagcaatg ggaggccgcc     780

aaggaaatcg tcaagaactt tgttcaaaan ccacggcatg gtataatact gcctgacgac     840
```

```
tggaagtttg acacggtaga cctgaagtcg gccatgcccg acgccattcc ctacctgacc    900

taccacgacg cgggcatcgc tagggcgctt ggcatagact tcaacaccgt tcaactaaac    960

atgggggtac aggcgataaa catcggcgag ttcgtaagcc tgacccagca gaccatcatt   1020

tcgctccagc gggagttcgc tagcgcggtc aacctctacc tcatccccaa gctagtgctt   1080

cccaactggc cgagcgctac tcgctttcct aggctcacct ttgagatgga ggagcgcaac   1140

gacttctccg ccgcggccaa ccttatgggc atgctcatca acgcggttaa ggactccgaa   1200

gacattccca ccgagctcaa ggcgctaata gacgctctgc ctagcaagat gcgccgggcg   1260

cttggcgtgg tggacgaggt gagggaagcg gtacgccaac ccgccgatta a            1311
```

```
<210> SEQ ID NO 13
<211> LENGTH: 417
<212> TYPE: PRT
<213> ORGANISM: Artificial Sequence
<220> FEATURE:
<223> OTHER INFORMATION: 40E
<220> FEATURE:
<221> NAME/KEY: VARIANT
<222> LOCATION: 251
<223> OTHER INFORMATION: Xaa = Any Amino Acid

<400> SEQUENCE: 13

Gly Pro Ala Lys Leu Glu Gly Ala Ser Val Pro Val Met Ser Thr Ser
1               5                   10                  15

Tyr Asp Glu Val Val Asp Arg Glu Phe Asp Glu Leu Leu Gln Gly Lys
            20                  25                  30

Asp Gly Leu Leu Val Tyr His Lys Met Leu Ser Asp Gly Thr Val Lys
        35                  40                  45

Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80

Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125

Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160

Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205

Leu Leu Ile Asn His Gly Leu Glu Arg Phe Met Ile Gly Val Pro Thr
    210                 215                 220

Leu Thr Ile Pro Lys Ser Val Arg Gln Gly Thr Lys Gln Trp Glu Ala
225                 230                 235                 240

Ala Lys Glu Ile Val Lys Asn Phe Val Gln Xaa Pro Arg His Gly Ile
                245                 250                 255
```

```
Ile Leu Pro Asp Asp Trp Lys Phe Asp Thr Val Asp Leu Lys Ser Ala
            260                 265                 270

Met Pro Asp Ala Ile Pro Tyr Leu Thr Tyr His Asp Ala Gly Ile Ala
        275                 280                 285

Arg Ala Leu Gly Ile Asp Phe Asn Thr Val Gln Leu Asn Met Gly Val
    290                 295                 300

Gln Ala Ile Asn Ile Gly Glu Phe Val Ser Leu Thr Gln Gln Thr Ile
305                 310                 315                 320

Ile Ser Leu Gln Arg Glu Phe Ala Ser Ala Val Asn Leu Tyr Leu Ile
                325                 330                 335

Pro Lys Leu Val Leu Pro Asn Trp Pro Ser Ala Thr Arg Phe Pro Arg
            340                 345                 350

Leu Thr Phe Glu Met Glu Glu Arg Asn Asp Phe Ser Ala Ala Ala Asn
        355                 360                 365

Leu Met Gly Met Leu Ile Asn Ala Val Lys Asp Ser Glu Asp Ile Pro
    370                 375                 380

Thr Glu Leu Lys Ala Leu Ile Asp Ala Leu Pro Ser Lys Met Arg Arg
385                 390                 395                 400

Ala Leu Gly Val Val Asp Glu Val Arg Glu Ala Val Arg Gln Pro Ala
                405                 410                 415

Asp
```

<210> SEQ ID NO 14
<211> LENGTH: 1311
<212> TYPE: DNA
<213> ORGANISM: Artificial Sequence
<220> FEATURE:
<223> OTHER INFORMATION: 40E
<220> FEATURE:
<221> NAME/KEY: misc_feature
<222> LOCATION: 810
<223> OTHER INFORMATION: n = A,T,C or G

<400> SEQUENCE: 14

```
atgggcagca gccatcatca tcatcatcac agcagcggcc tggaagttct gttccaggga     60

ccagcaaagc tcgagggcgc ctccgtgccg gtgatgtcca ccagttacga cgaggtggtg    120

gaccgggagt ttgacgagct actgcagggc aaggacggct tgctcgtcta ccacaagatg    180

ctctcggacg gcacggttaa gaacgccctc aactacatct tcggacgcat ccgctcggcg    240

aagtggtacg tagagcccgc ctctaccgac ccggaagaca tcgccatcgc cgccttcatc    300

cacgcccagt taggcataga cgacgcttcg gtgggcaagt atccctttgg ccgccttttc    360

gccatctacg aaaacgccta catatacggc atggccgccg gggaaatcgt actaaccctt    420

ggcgcggacg gcaagctcat ccttgacaaa atcgtcccta tccacccttt caacattgac    480

gaggtgcttt acgacgagga aggcggtcca aaggcgctaa agctaagcgg agaggtgaag    540

ggcggaagcc agtttgtgag cgggttggag attcctatat ggaagaccgt ggtcttcctg    600

cacaacgacg acggctcctt caccggacag agcgccctca gagccgccgt gccgcattgg    660

ctagccaaac gagccctcat tctcctcatc aaccacgggt tggagcgctt catgattggc    720

gtgcccaccc tcaccatccc caagagcgtg cgtcagggaa ccaagcaatg ggaggccgcc    780

aaggaaatcg tcaagaactt tgttcaaaan ccacggcatg gtataatact gcctgacgac    840

tggaagtttg acacggtaga cctgaagtcg gccatgcccg acgccattcc ctacctgacc    900

taccacgacg cgggcatcgc tagggcgctt ggcatagact tcaacaccgt tcaactaaac    960

atgggggtac aggcgataaa catcggcgag ttcgtaagcc tgacccagca gaccatcatt   1020
```

```
tcgctccagc gggagttcgc tagcgcggtc aacctctacc tcatccccaa gctagtgctt   1080

cccaactggc cgagcgctac tcgctttcct aggctcacct ttgagatgga ggagcgcaac   1140

gacttctccg ccgcggccaa ccttatgggc atgctcatca acgcggttaa ggactccgaa   1200

gacattccca ccgagctcaa ggcgctaata gacgctctgc ctagcaagat gcgccgggcg   1260

cttggcgtgg tggacgaggt gagggaagcg gtacgccaac ccgccgatta a            1311


<210> SEQ ID NO 15
<211> LENGTH: 417
<212> TYPE: PRT
<213> ORGANISM: Artificial Sequence
<220> FEATURE:
<223> OTHER INFORMATION: G

<400> SEQUENCE: 15

Gly Pro Ala Lys Leu Glu Gly Ala Ser Val Pro Val Met Ser Thr Ser
1               5                   10                  15

Tyr Asp Val Val Val Asp Arg Glu Phe Asp Glu Leu Leu Gln Gly Lys
            20                  25                  30

Asp Gly Leu Leu Val Tyr His Lys Met Leu Ser Asp Gly Thr Val Lys
        35                  40                  45

Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80

Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125

Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160

Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205

Leu Leu Ile Asn His Gly Leu Glu Arg Phe Met Ile Gly Val Pro Thr
    210                 215                 220

Leu Thr Ile Pro Lys Ser Val Arg Gln Gly Thr Lys Gln Trp Glu Ala
225                 230                 235                 240

Ala Lys Glu Ile Val Lys Asn Phe Val Gln Lys Pro Arg His Gly Ile
                245                 250                 255

Ile Leu Pro Asp Asp Trp Lys Phe Asp Thr Val Asp Leu Lys Ser Ala
            260                 265                 270

Met Pro Asp Ala Ile Pro Tyr Leu Thr Tyr His Asp Ala Gly Ile Ala
        275                 280                 285

Arg Ala Leu Gly Ile Asp Phe Asn Thr Val Gln Leu Asn Met Gly Gly
    290                 295                 300

Gln Ala Ile Asn Ile Gly Glu Phe Val Ser Leu Thr Gln Gln Thr Ile
305                 310                 315                 320
```

```
Ile Ser Leu Gln Arg Glu Phe Ala Ser Ala Val Asn Leu Tyr Leu Ile
                325                 330                 335

Pro Lys Leu Val Leu Pro Asn Trp Pro Ser Ala Thr Arg Phe Pro Arg
            340                 345                 350

Leu Thr Phe Glu Met Glu Glu Arg Asn Asp Phe Ser Ala Ala Ala Asn
        355                 360                 365

Leu Met Gly Met Leu Ile Asn Ala Val Lys Asp Ser Glu Asp Ile Pro
    370                 375                 380

Thr Glu Leu Lys Ala Leu Ile Asp Ala Leu Pro Ser Lys Met Arg Arg
385                 390                 395                 400

Ala Leu Gly Val Val Asp Glu Val Arg Glu Ala Val Arg Gln Pro Ala
                405                 410                 415

Asp


<210> SEQ ID NO 16
<211> LENGTH: 1311
<212> TYPE: DNA
<213> ORGANISM: Artificial Sequence
<220> FEATURE:
<223> OTHER INFORMATION: G

<400> SEQUENCE: 16

atgggcagca gccatcatca tcatcatcac agcagcggcc tggaagttct gttccaggga      60

ccagcaaagc tcgagggcgc ctccgtgccg gtgatgtcca ccagttacga cgtggtggtg     120

gaccgggagt ttgacgagct actgcagggc aaggacggct tgctcgtcta ccacaagatg     180

ctctcggacg gcacggttaa gaacgccctc aactacatct tcggacgcat ccgctcggcg     240

aagtggtacg tagagcccgc ctctaccgac ccggaagaca tcgccatcgc cgccttcatc     300

cacgcccagt taggcataga cgacgcttcg gtgggcaagt atccctttgg ccgccttttc     360

gccatctacg aaaacgccta catatacggc atggccgccg gggaaatcgt actaaccctt     420

ggcgcggacg gcaagctcat ccttgacaaa atcgtcccta tccacccttt caacattgac     480

gaggtgcttt acgacgagga aggcggtcca aaggcgctaa agctaagcgg agaggtgaag     540

ggcggaagcc agtttgtgag cgggttggag attcctatat ggaagaccgt ggtcttcctg     600

cacaacgacg acggctcctt caccggacag agcgccctca gagccgccgt gccgcattgg     660

ctagccaaac gagccctcat tctcctcatc aaccacgggt tggagcgctt catgattggc     720

gtgcccaccc tcaccatccc caagagcgtg cgtcagggaa ccaagcaatg ggaggccgcc     780

aaggaaatcg tcaagaactt tgttcaaaaa ccacggcatg gtataatact gcctgacgac     840

tggaagtttg acacggtaga cctgaagtcg gccatgcccg acgccattcc ctacctgacc     900

taccacgacg cgggcatcgc tagggcgctt ggcatagact tcaacaccgt tcaactaaac     960

atggggggac aggcgataaa catcggcgag ttcgtaagcc tgacccagca gaccatcatt    1020

tcgctccagc gggagttcgc tagcgcggtc aacctctacc tcatccccaa gctagtgctt    1080

cccaactggc cgagcgctac tcgctttcct aggctcacct ttgagatgga ggagcgcaac    1140

gacttctccg ccgcggccaa ccttatgggc atgctcatca acgcggttaa ggactccgaa    1200

gacattccca ccgagctcaa ggcgctaata gacgctctgc ctagcaagat gcgccgggcg    1260

cttggcgtgg tggacgaggt gagggaagcg gtacgccaac ccgccgatta a             1311


<210> SEQ ID NO 17
<211> LENGTH: 417
<212> TYPE: PRT
<213> ORGANISM: Artificial Sequence
```

<220> FEATURE:
<223> OTHER INFORMATION: M

<400> SEQUENCE: 17

```
Gly Pro Ala Lys Leu Glu Gly Ala Ser Val Pro Val Met Ser Thr Ser
1               5                   10                  15

Tyr Asp Val Val Val Asp Arg Glu Phe Asp Glu Leu Leu Gln Gly Lys
            20                  25                  30

Asp Gly Leu Leu Val Tyr His Lys Met Leu Ser Asp Gly Thr Val Lys
        35                  40                  45

Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80

Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125

Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160

Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205

Leu Leu Ile Asn His Gly Leu Glu Arg Phe Met Ile Gly Val Pro Thr
    210                 215                 220

Leu Thr Ile Pro Lys Ser Val Arg Gln Gly Thr Lys Gln Trp Glu Ala
225                 230                 235                 240

Ala Lys Glu Ile Val Lys Asn Phe Val Gln Lys Pro Arg His Gly Ile
                245                 250                 255

Ile Leu Pro Asp Asp Trp Lys Phe Asp Thr Val Asp Leu Lys Ser Ala
            260                 265                 270

Met Pro Asp Ala Ile Pro Tyr Leu Thr Tyr His Asp Ala Gly Ile Ala
        275                 280                 285

Arg Ala Leu Gly Ile Asp Phe Asn Thr Val Gln Leu Asn Met Gly Met
    290                 295                 300

Gln Ala Ile Asn Ile Gly Glu Phe Val Ser Leu Thr Gln Gln Thr Ile
305                 310                 315                 320

Ile Ser Leu Gln Arg Glu Phe Ala Ser Ala Val Asn Leu Tyr Leu Ile
                325                 330                 335

Pro Lys Leu Val Leu Pro Asn Trp Pro Ser Ala Thr Arg Phe Pro Arg
            340                 345                 350

Leu Thr Phe Glu Met Glu Glu Arg Asn Asp Phe Ser Ala Ala Ala Asn
        355                 360                 365

Leu Met Gly Met Leu Ile Asn Ala Val Lys Asp Ser Glu Asp Ile Pro
    370                 375                 380

Thr Glu Leu Lys Ala Leu Ile Asp Ala Leu Pro Ser Lys Met Arg Arg
385                 390                 395                 400
```

```
Ala Leu Gly Val Val Asp Glu Val Arg Glu Ala Val Arg Gln Pro Ala
                405                 410                 415

Asp


<210> SEQ ID NO 18
<211> LENGTH: 1311
<212> TYPE: DNA
<213> ORGANISM: Artificial Sequence
<220> FEATURE:
<223> OTHER INFORMATION: M

<400> SEQUENCE: 18

atgggcagca gccatcatca tcatcatcac agcagcggcc tggaagttct gttccaggga     60

ccagcaaagc tcgagggcgc ctccgtgccg gtgatgtcca ccagttacga cgtggtggtg    120

gaccgggagt ttgacgagct actgcagggc aaggacggct tgctcgtcta ccacaagatg    180

ctctcggacg gcacggttaa gaacgccctc aactacatct tcggacgcat ccgctcggcg    240

aagtggtacg tagagcccgc ctctaccgac ccggaagaca tcgccatcgc cgccttcatc    300

cacgcccagt taggcataga cgacgcttcg gtgggcaagt atccctttgg ccgccttttc    360

gccatctacg aaaacgccta catatacggc atggccgccg gggaaatcgt actaaccctt    420

ggcgcggacg gcaagctcat ccttgacaaa atcgtcccta tccacccttt caacattgac    480

gaggtgcttt acgacgagga aggcggtcca aaggcgctaa agctaagcgg agaggtgaag    540

ggcggaagcc agtttgtgag cgggttggag attcctatat ggaagaccgt ggtcttcctg    600

cacaacgacg acggctcctt caccggacag agcgccctca gagccgccgt gccgcattgg    660

ctagccaaac gagccctcat tctcctcatc aaccacgggt tggagcgctt catgattggc    720

gtgcccaccc tcaccatccc caagagcgtg cgtcagggaa ccaagcaatg ggaggccgcc    780

aaggaaatcg tcaagaactt tgttcaaaaa ccacggcatg gtataatact gcctgacgac    840

tggaagtttg acacggtaga cctgaagtcg gccatgcccg acgccattcc ctacctgacc    900

taccacgacg cgggcatcgc tagggcgctt ggcatagact tcaacaccgt tcaactaaac    960

atggggatgc aggcgataaa catcggcgag ttcgtaagcc tgacccagca gaccatcatt   1020

tcgctccagc gggagttcgc tagcgcggtc aacctctacc tcatccccaa gctagtgctt   1080

cccaactggc cgagcgctac tcgctttcct aggctcacct ttgagatgga ggagcgcaac   1140

gacttctccg ccgcggccaa ccttatgggc atgctcatca acgcggttaa ggactccgaa   1200

gacattccca ccgagctcaa ggcgctaata gacgctctgc ctagcaagat gcgccgggcg   1260

cttggcgtgg tggacgaggt gagggaagcg gtacgccaac ccgccgatta a             1311


<210> SEQ ID NO 19
<211> LENGTH: 417
<212> TYPE: PRT
<213> ORGANISM: Artificial Sequence
<220> FEATURE:
<223> OTHER INFORMATION: K

<400> SEQUENCE: 19

Gly Pro Ala Lys Leu Glu Gly Ala Ser Val Pro Val Met Ser Thr Ser
1               5                   10                  15

Tyr Asp Val Val Val Asp Arg Glu Phe Asp Glu Leu Leu Gln Gly Lys
            20                  25                  30

Asp Gly Leu Leu Val Tyr His Lys Met Leu Ser Asp Gly Thr Val Lys
        35                  40                  45
```

```
Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80

Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125

Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160

Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205

Leu Leu Ile Asn His Gly Leu Glu Arg Phe Met Ile Gly Val Pro Thr
    210                 215                 220

Leu Thr Ile Pro Lys Ser Val Arg Gln Gly Thr Lys Gln Trp Glu Ala
225                 230                 235                 240

Ala Lys Glu Ile Val Lys Asn Phe Val Gln Lys Pro Arg His Gly Ile
                245                 250                 255

Ile Leu Pro Asp Asp Trp Lys Phe Asp Thr Val Asp Leu Lys Ser Ala
            260                 265                 270

Met Pro Asp Ala Ile Pro Tyr Leu Thr Tyr His Asp Ala Gly Ile Ala
        275                 280                 285

Arg Ala Leu Gly Ile Asp Phe Asn Thr Val Gln Leu Asn Met Gly Val
    290                 295                 300

Gln Ala Lys Asn Ile Gly Glu Phe Val Ser Leu Thr Gln Gln Thr Ile
305                 310                 315                 320

Ile Ser Leu Gln Arg Glu Phe Ala Ser Ala Val Asn Leu Tyr Leu Ile
                325                 330                 335

Pro Lys Leu Val Leu Pro Asn Trp Pro Ser Ala Thr Arg Phe Pro Arg
            340                 345                 350

Leu Thr Phe Glu Met Glu Glu Arg Asn Asp Phe Ser Ala Ala Ala Asn
        355                 360                 365

Leu Met Gly Met Leu Ile Asn Ala Val Lys Asp Ser Glu Asp Ile Pro
    370                 375                 380

Thr Glu Leu Lys Ala Leu Ile Asp Ala Leu Pro Ser Lys Met Arg Arg
385                 390                 395                 400

Ala Leu Gly Val Val Asp Glu Val Arg Glu Ala Val Arg Gln Pro Ala
                405                 410                 415

Asp
```

<210> SEQ ID NO 20
<211> LENGTH: 1311
<212> TYPE: DNA
<213> ORGANISM: Artificial Sequence
<220> FEATURE:
<223> OTHER INFORMATION: K

<400> SEQUENCE: 20

```
atgggcagca gccatcatca tcatcatcac agcagcggcc tggaagttct gttccaggga      60
ccagcaaagc tcgagggcgc ctccgtgccg gtgatgtcca ccagttacga cgtggtggtg     120
gaccgggagt ttgacgagct actgcagggc aaggacggct tgctcgtcta ccacaagatg     180
ctctcggacg gcacggttaa gaacgccctc aactacatct tcggacgcat ccgctcggcg     240
aagtggtacg tagagcccgc ctctaccgac ccggaagaca tcgccatcgc cgccttcatc     300
cacgcccagt taggcataga cgacgcttcg gtgggcaagt atccctttgg ccgccttttc     360
gccatctacg aaaacgccta catatacggc atggccgccg ggaaatcgt actaaccctt      420
ggcgcggacg gcaagctcat ccttgacaaa atcgtcccta tccacccttt caacattgac     480
gaggtgcttt acgacgagga aggcggtcca aaggcgctaa agctaagcgg agaggtgaag     540
ggcggaagcc agtttgtgag cgggttggag attcctatat ggaagaccgt ggtcttcctg     600
cacaacgacg acggctcctt caccggacag agcgccctca gagccgccgt gccgcattgg     660
ctagccaaac gagccctcat tctcctcatc aaccacgggt tggagcgctt catgattggc     720
gtgcccaccc tcaccatccc caagagcgtg cgtcagggaa ccaagcaatg ggaggccgcc     780
aaggaaatcg tcaagaactt tgttcaaaaa ccacggcatg gtataatact gcctgacgac     840
tggaagtttg acacggtaga cctgaagtcg gccatgcccg acgccattcc ctacctgacc     900
taccacgacg cgggcatcgc tagggcgctt ggcatagact tcaacaccgt tcaactaaac     960
atgggggtac aggcgaagaa catcggcgag ttcgtaagcc tgacccagca gaccatcatt    1020
tcgctccagc gggagttcgc tagcgcggtc aacctctacc tcatccccaa gctagtgctt    1080
cccaactggc cgagcgctac tcgctttcct aggctcacct ttgagatgga ggagcgcaac    1140
gacttctccg ccgcggccaa ccttatgggc atgctcatca acgcggttaa ggactccgaa    1200
gacattccca ccgagctcaa ggcgctaata gacgctctgc ctagcaagat gcgccgggcg    1260
cttggcgtgg tggacgaggt gagggaagcg gtacgccaac ccgccgatta a             1311
```

<210> SEQ ID NO 21
<211> LENGTH: 417
<212> TYPE: PRT
<213> ORGANISM: Artificial Sequence
<220> FEATURE:
<223> OTHER INFORMATION: CGG

<400> SEQUENCE: 21

```
Gly Pro Ala Lys Leu Glu Gly Ala Ser Val Pro Val Met Ser Thr Ser
1               5                   10                  15

Tyr Asp Val Val Val Asp Arg Glu Phe Asp Glu Cys Leu Gln Gly Lys
            20                  25                  30

Asp Gly Leu Leu Val Tyr His Lys Met Leu Ser Asp Gly Thr Val Lys
        35                  40                  45

Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80

Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125
```

```
Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160

Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205

Leu Leu Ile Asn His Gly Leu Glu Arg Phe Met Ile Gly Val Pro Thr
    210                 215                 220

Leu Thr Ile Pro Lys Ser Val Arg Gln Gly Thr Lys Gln Trp Glu Ala
225                 230                 235                 240

Ala Lys Glu Ile Val Lys Asn Phe Val Gln Lys Pro Arg His Gly Ile
                245                 250                 255

Ile Leu Pro Asp Asp Trp Lys Phe Asp Thr Val Asp Leu Lys Ser Ala
            260                 265                 270

Met Pro Asp Ala Ile Pro Tyr Leu Thr Tyr His Asp Ala Gly Ile Ala
        275                 280                 285

Arg Ala Leu Gly Ile Asp Phe Asn Thr Val Gln Leu Asn Met Gly Gly
    290                 295                 300

Gln Ala Gly Asn Ile Gly Glu Phe Val Ser Leu Thr Gln Gln Thr Ile
305                 310                 315                 320

Ile Ser Leu Gln Arg Glu Phe Ala Ser Ala Val Asn Leu Tyr Leu Ile
                325                 330                 335

Pro Lys Leu Val Leu Pro Asn Trp Pro Ser Ala Thr Arg Phe Pro Arg
            340                 345                 350

Leu Thr Phe Glu Met Glu Glu Arg Asn Asp Phe Ser Ala Ala Ala Asn
        355                 360                 365

Leu Met Gly Met Leu Ile Asn Ala Val Lys Asp Ser Glu Asp Ile Pro
    370                 375                 380

Thr Glu Leu Lys Ala Leu Ile Asp Ala Leu Pro Ser Lys Met Arg Arg
385                 390                 395                 400

Ala Leu Gly Val Val Asp Glu Val Arg Glu Ala Val Arg Gln Pro Ala
                405                 410                 415

Asp


<210> SEQ ID NO 22
<211> LENGTH: 1311
<212> TYPE: DNA
<213> ORGANISM: Artificial Sequence
<220> FEATURE:
<223> OTHER INFORMATION: CGG

<400> SEQUENCE: 22

atgggcagca gccatcatca tcatcatcac agcagcggcc tggaagttct gttccaggga      60

ccagcaaagc tcgagggcgc ctccgtgccg gtgatgtcca ccagttacga cgtggtggtg     120

gaccgggagt ttgacgagtg tctgcagggc aaggacggct tgctcgtcta ccacaagatg     180

ctctcggacg gcacggttaa gaacgccctc aactacatct tcggacgcat ccgctcggcg     240

aagtggtacg tagagcccgc ctctaccgac ccggaagaca tcgccatcgc cgccttcatc     300

cacgcccagt taggcataga cgacgcttcg gtgggcaagt atccctttgg ccgccttttc     360

gccatctacg aaaacgccta catatacggc atggccgccg gggaaatcgt actaaccctt     420
```

```
ggcgcggacg gcaagctcat ccttgacaaa atcgtcccta tccacccttt caacattgac    480

gaggtgcttt acgacgagga aggcggtcca aaggcgctaa agctaagcgg agaggtgaag    540

ggcggaagcc agtttgtgag cgggttggag attcctatat ggaagaccgt ggtcttcctg    600

cacaacgacg acggctcctt caccggacag agcgccctca gagccgccgt gccgcattgg    660

ctagccaaac gagccctcat tctcctcatc aaccacgggt tggagcgctt catgattggc    720

gtgcccaccc tcaccatccc caagagcgtg cgtcagggaa ccaagcaatg ggaggccgcc    780

aaggaaatcg tcaagaactt tgttcaaaaa ccacggcatg gtataatact gcctgacgac    840

tggaagtttg acacggtaga cctgaagtcg gccatgcccg acgccattcc ctacctgacc    900

taccacgacg cgggcatcgc tagggcgctt ggcatagact tcaacaccgt tcaactaaac    960

atggggggac aggcgggaaa catcggcgag ttcgtaagcc tgacccagca gaccatcatt   1020

tcgctccagc gggagttcgc tagcgcggtc aacctctacc tcatccccaa gctagtgctt   1080

cccaactggc cgagcgctac tcgctttcct aggctcacct ttgagatgga ggagcgcaac   1140

gacttctccg ccgcggccaa ccttatgggc atgctcatca acgcggttaa ggactccgaa   1200

gacattccca ccgagctcaa ggcgctaata gacgctctgc ctagcaagat gcgccgggcg   1260

cttggcgtgg tggacgaggt gagggaagcg gtacgccaac ccgccgatta a            1311
```

<210> SEQ ID NO 23
<211> LENGTH: 416
<212> TYPE: PRT
<213> ORGANISM: Artificial Sequence
<220> FEATURE:
<223> OTHER INFORMATION: Loop2GG

<400> SEQUENCE: 23

```
Gly Pro Ala Lys Leu Glu Gly Ala Ser Val Pro Val Met Ser Thr Ser
1               5                   10                  15

Tyr Asp Val Val Val Asp Arg Glu Phe Asp Glu Leu Leu Gln Gly Lys
            20                  25                  30

Asp Gly Leu Leu Val Tyr His Lys Met Leu Ser Asp Gly Thr Val Lys
        35                  40                  45

Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80

Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125

Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160

Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205
```

```
Leu Leu Ile Asn His Gly Leu Glu Arg Phe Met Ile Gly Val Pro Thr
    210                 215                 220

Leu Thr Ile Pro Lys Ser Val Arg Gln Gly Thr Lys Gln Trp Glu Ala
225                 230                 235                 240

Ala Lys Glu Ile Val Lys Asn Phe Val Gln Lys Pro Arg His Gly Ile
                245                 250                 255

Ile Leu Pro Asp Asp Trp Lys Phe Asp Thr Val Asp Leu Lys Ser Ala
            260                 265                 270

Met Pro Asp Ala Ile Pro Tyr Leu Thr Tyr His Asp Ala Gly Ile Ala
        275                 280                 285

Arg Ala Leu Gly Ile Asp Phe Asn Thr Val Gln Leu Asn Met Gly Gly
    290                 295                 300

Gly Gly Asn Ile Gly Glu Phe Val Ser Leu Thr Gln Gln Thr Ile Ile
305                 310                 315                 320

Ser Leu Gln Arg Glu Phe Ala Ser Ala Val Asn Leu Tyr Leu Ile Pro
                325                 330                 335

Lys Leu Val Leu Pro Asn Trp Pro Ser Ala Thr Arg Phe Pro Arg Leu
            340                 345                 350

Thr Phe Glu Met Glu Glu Arg Asn Asp Phe Ser Ala Ala Ala Asn Leu
        355                 360                 365

Met Gly Met Leu Ile Asn Ala Val Lys Asp Ser Glu Asp Ile Pro Thr
    370                 375                 380

Glu Leu Lys Ala Leu Ile Asp Ala Leu Pro Ser Lys Met Arg Arg Ala
385                 390                 395                 400

Leu Gly Val Val Asp Glu Val Arg Glu Ala Val Arg Gln Pro Ala Asp
                405                 410                 415
```

<210> SEQ ID NO 24
<211> LENGTH: 1308
<212> TYPE: DNA
<213> ORGANISM: Artificial Sequence
<220> FEATURE:
<223> OTHER INFORMATION: Loop2GG

<400> SEQUENCE: 24

```
atgggcagca gccatcatca tcatcatcac agcagcggcc tggaagttct gttccaggga     60

ccagcaaagc tcgagggcgc ctccgtgccg gtgatgtcca ccagttacga cgtggtggtg    120

gaccgggagt ttgacgagct actgcagggc aaggacggct tgctcgtcta ccacaagatg    180

ctctcggacg gcacggttaa gaacgccctc aactacatct tcggacgcat ccgctcggcg    240

aagtggtacg tagagcccgc ctctaccgac ccggaagaca tcgccatcgc cgccttcatc    300

cacgcccagt taggcataga cgacgcttcg gtgggcaagt atccctttgg ccgccttttc    360

gccatctacg aaaacgccta catatacggc atggccgccg gggaaatcgt actaaccctt    420

ggcgcggacg gcaagctcat ccttgacaaa atcgtcccta tccacccttt caacattgac    480

gaggtgcttt acgacgagga aggcggtcca aaggcgctaa agctaagcgg agaggtgaag    540

ggcggaagcc agtttgtgag cgggttggag attcctatat ggaagaccgt ggtcttcctg    600

cacaacgacg acggctcctt caccggacag agcgccctca gagccgccgt gccgcattgg    660

ctagccaaac gagccctcat tctcctcatc aaccacgggt tggagcgctt catgattggc    720

gtgcccaccc tcaccatccc caagagcgtg cgtcagggaa ccaagcaatg ggaggccgcc    780

aaggaaatcg tcaagaactt tgttcaaaaa ccacggcatg gtataatact gcctgacgac    840

tggaagtttg acacggtaga cctgaagtcg gccatgcccg acgccattcc ctacctgacc    900
```

```
taccacgacg cgggcatcgc tagggcgctt ggcatagact tcaacaccgt tcaactaaac    960

atggggggag gcggtaacat cggcgagttc gtaagcctga cccagcagac catcatttcg   1020

ctccagcggg agttcgctag cgcggtcaac ctctacctca tccccaagct agtgcttccc   1080

aactggccga gcgctactcg ctttcctagg ctcacctttg agatggagga gcgcaacgac   1140

ttctccgccg cggccaacct tatgggcatg ctcatcaacg cggttaagga ctccgaagac   1200

attcccaccg agctcaaggc gctaatagac gctctgccta gcaagatgcg ccgggcgctt   1260

ggcgtggtgg acgaggtgag ggaagcggta cgccaacccg ccgattaa                1308


<210> SEQ ID NO 25
<211> LENGTH: 410
<212> TYPE: PRT
<213> ORGANISM: Artificial Sequence
<220> FEATURE:
<223> OTHER INFORMATION: 49CLoop3G

<400> SEQUENCE: 25

Gly Pro Ala Lys Leu Glu Gly Ala Ser Val Pro Val Met Ser Thr Ser
1               5                   10                  15

Tyr Asp Val Val Val Asp Arg Glu Phe Asp Glu Cys Leu Gln Gly Lys
            20                  25                  30

Asp Gly Leu Leu Val Tyr His Lys Met Leu Ser Asp Gly Thr Val Lys
        35                  40                  45

Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80

Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125

Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160

Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205

Leu Leu Ile Asn His Gly Leu Glu Arg Phe Met Ile Gly Val Pro Thr
    210                 215                 220

Leu Thr Ile Pro Lys Ser Val Arg Gln Gly Thr Lys Gln Trp Glu Ala
225                 230                 235                 240

Ala Lys Glu Ile Val Lys Asn Phe Val Gln Lys Pro Arg His Gly Ile
                245                 250                 255

Ile Leu Pro Asp Asp Trp Lys Phe Asp Thr Val Asp Leu Lys Ser Ala
            260                 265                 270

Met Pro Asp Ala Ile Pro Tyr Leu Thr Tyr His Asp Ala Gly Ile Ala
        275                 280                 285
```

```
Arg Ala Leu Gly Ile Asp Phe Asn Thr Val Gln Leu Gly Ile Gly Glu
    290                 295                 300

Phe Val Ser Leu Thr Gln Gln Thr Ile Ile Ser Leu Gln Arg Glu Phe
305                 310                 315                 320

Ala Ser Ala Val Asn Leu Tyr Leu Ile Pro Lys Leu Val Leu Pro Asn
                325                 330                 335

Trp Pro Ser Ala Thr Arg Phe Pro Arg Leu Thr Phe Glu Met Glu Glu
            340                 345                 350

Arg Asn Asp Phe Ser Ala Ala Ala Asn Leu Met Gly Met Leu Ile Asn
        355                 360                 365

Ala Val Lys Asp Ser Glu Asp Ile Pro Thr Glu Leu Lys Ala Leu Ile
    370                 375                 380

Asp Ala Leu Pro Ser Lys Met Arg Arg Ala Leu Gly Val Val Asp Glu
385                 390                 395                 400

Val Arg Glu Ala Val Arg Gln Pro Ala Asp
                405                 410
```

<210> SEQ ID NO 26
<211> LENGTH: 1269
<212> TYPE: DNA
<213> ORGANISM: Artificial Sequence
<220> FEATURE:
<223> OTHER INFORMATION: 49CLoop3G
<220> FEATURE:
<221> NAME/KEY: misc_feature
<222> LOCATION: 1266
<223> OTHER INFORMATION: n = A,T,C or G

<400> SEQUENCE: 26

```
catcatcaca gcagcggcct ggaagttctg ttccagggac cagcaaagct cgagggcgcc     60

tccgtgccgg tgatgtccac cagttacgac gtggtggtgg accgggagtt tgacgagtgt    120

ctgcagggca aggacggctt gctcgtctac cacaagatgc tctcggacgg cacggttaag    180

aacgccctca actacatctt cggacgcatc cgctcggcga agtggtacgt agagcccgcc    240

tctaccgacc cggaagacat cgccatcgcc gccttcatcc acgcccagtt aggcatagac    300

gacgcttcgg tgggcaagta tccctttggc cgccttttcg ccatctacga aaacgcctac    360

atatacggca tggccgccgg ggaaatcgta ctaacccttg gcgcggacgg caagctcatc    420

cttgacaaaa tcgtccctat ccaccctttc aacattgacg aggtgcttta cgacgaggaa    480

ggcggtccaa aggcgctaaa gctaagcgga gaggtgaagg gcggaagcca gtttgtgagc    540

gggttggaga ttcctatatg gaagaccgtg gtcttcctgc acaacgacga cggctccttc    600

accggacaga gcgccctcag agccgccgtg ccgcattggc tagccaaacg agccctcatt    660

ctcctcatca accacgggtt ggagcgcttc atgattggcg tgcccaccct caccatcccc    720

aagagcgtgc gtcagggaac caagcaatgg gaggccgcca aggaaatcgt caagaacttt    780

gttcaaaaac cacggcatgg tataatactg cctgacgact ggaagtttga cacggtagac    840

ctgaagtcgg ccatgcccga cgccattccc tacctgacct accacgacgc gggcatcgct    900

agggcgcttg gcatagactt caacaccgtt caactaggta tcggcgagtt cgtaagcctg    960

acccagcaga ccatcatttc gctccagcgg gagttcgcta gcgcggtcaa cctctacctc   1020

atccccaagc tagtgcttcc caactggccg agcgctactc gctttcctag gctcaccttt   1080

gagatggagg agcgcaacga cttctccgcc gcggccaacc ttatgggcat gctcatcaac   1140

gcggttaagg actccgaaga cattcccacc gagctcaagg cgctaataga cgctctgcct   1200
```

```
agcaagatgc gccgggcgct tggcgtggtg gacgaggtga gggaagcggt acgccaaccc   1260

gccgantaa                                                           1269


<210> SEQ ID NO 27
<211> LENGTH: 417
<212> TYPE: PRT
<213> ORGANISM: Artificial Sequence
<220> FEATURE:
<223> OTHER INFORMATION: CD/N

<400> SEQUENCE: 27

Gly Pro Ala Lys Leu Glu Gly Ala Ser Val Pro Val Met Ser Thr Ser
1               5                   10                  15

Tyr Asp Val Val Val Asp Arg Glu Phe Asp Glu Cys Leu Gln Gly Lys
            20                  25                  30

Asp Gly Leu Leu Val Tyr His Lys Met Leu Ser Asp Gly Thr Val Lys
        35                  40                  45

Asn Ala Leu Asn Tyr Ile Phe Gly Arg Ile Arg Ser Ala Lys Trp Tyr
    50                  55                  60

Val Glu Pro Ala Ser Thr Asp Pro Glu Asp Ile Ala Ile Ala Ala Phe
65                  70                  75                  80

Ile His Ala Gln Leu Gly Ile Asp Asp Ala Ser Val Gly Lys Tyr Pro
                85                  90                  95

Phe Gly Arg Leu Phe Ala Ile Tyr Glu Asn Ala Tyr Ile Tyr Gly Met
            100                 105                 110

Ala Ala Gly Glu Ile Val Leu Thr Leu Gly Ala Asp Gly Lys Leu Ile
        115                 120                 125

Leu Asp Lys Ile Val Pro Ile His Pro Phe Asn Ile Asp Glu Val Leu
    130                 135                 140

Tyr Asp Glu Glu Gly Gly Pro Lys Ala Leu Lys Leu Ser Gly Glu Val
145                 150                 155                 160

Lys Gly Gly Ser Gln Phe Val Ser Gly Leu Glu Ile Pro Ile Trp Lys
                165                 170                 175

Thr Val Val Phe Leu His Asn Asp Asp Gly Ser Phe Thr Gly Gln Ser
            180                 185                 190

Ala Leu Arg Ala Ala Val Pro His Trp Leu Ala Lys Arg Ala Leu Ile
        195                 200                 205

Leu Leu Ile Asn His Gly Leu Glu Arg Phe Met Ile Gly Val Pro Thr
    210                 215                 220

Leu Thr Ile Pro Lys Ser Val Arg Gln Gly Thr Lys Gln Trp Glu Ala
225                 230                 235                 240

Ala Lys Glu Ile Val Lys Asn Phe Val Gln Lys Pro Arg His Gly Ile
                245                 250                 255

Ile Leu Pro Asn Asp Trp Lys Phe Asn Thr Val Asn Leu Lys Ser Ala
            260                 265                 270

Met Pro Asn Ala Ile Pro Tyr Leu Thr Tyr His Asp Ala Gly Ile Ala
        275                 280                 285

Arg Ala Leu Gly Ile Asp Phe Asn Thr Val Gln Leu Asn Met Gly Val
    290                 295                 300

Gln Ala Ile Asn Ile Gly Glu Phe Val Ser Leu Thr Gln Gln Thr Ile
305                 310                 315                 320

Ile Ser Leu Gln Arg Glu Phe Ala Ser Ala Ala Asn Leu Tyr Leu Ile
                325                 330                 335

Pro Lys Leu Val Leu Pro Asn Trp Pro Ser Ala Thr Arg Phe Pro Arg
            340                 345                 350
```

```
Leu Thr Phe Glu Met Glu Glu Arg Asn Asp Phe Ser Ala Ala Ala Asn
        355                 360                 365

Leu Met Gly Met Leu Ile Asn Ala Val Lys Asp Ser Glu Asp Ile Pro
    370                 375                 380

Thr Glu Leu Lys Ala Leu Ile Asp Ala Leu Pro Ser Lys Met Arg Arg
385                 390                 395                 400

Ala Leu Gly Val Val Asp Glu Val Arg Glu Ala Val Arg Gln Pro Ala
                405                 410                 415

Asp
```

<210> SEQ ID NO 28
<211> LENGTH: 1311
<212> TYPE: DNA
<213> ORGANISM: Artificial Sequence
<220> FEATURE:
<223> OTHER INFORMATION: CD/N

<400> SEQUENCE: 28

```
atgggcagca gccatcatca tcatcatcac agcagcggcc tggaagttct gttccaggga      60

ccagcaaagc tcgagggcgc ctccgtgccg gtgatgtcca ccagttacga cgtggtggtg     120

gaccgggagt ttgacgagtg tctgcagggc aaggacggct tgctcgtcta ccacaagatg     180

ctctcggacg gcacggttaa gaacgccctc aactacatct tcggacgcat ccgctcggcg     240

aagtggtacg tagagcccgc ctctaccgac ccggaagaca tcgccatcgc cgccttcatc     300

cacgcccagt taggcataga cgacgcttcg gtgggcaagt atccctttgg ccgccttttc     360

gccatctacg aaaacgccta catatacggc atggccgccg ggaaatcgt actaaccctt      420

ggcgcggacg gcaagctcat ccttgacaaa atcgtcccta tccacccttt caacattgac     480

gaggtgcttt acgacgagga aggcggtcca aaggcgctaa agctaagcgg agaggtgaag     540

ggcggaagcc agtttgtgag cgggttggag attcctatat ggaagaccgt ggtcttcctg     600

cacaacgacg acggctcctt caccggacag agcgccctca gagccgccgt gccgcattgg     660

ctagccaaac gagccctcat tctcctcatc aaccacgggt tggagcgctt catgattggc     720

gtgcccaccc tcaccatccc caagagcgtg cgtcagggaa ccaagcaatg ggaggccgcc     780

aaggaaatcg tcaagaactt tgttcaaaaa ccacggcatg gtataatact gcctaacgac     840

tggaagttta acacggtaaa cctgaagtcg gccatgccca acgccattcc ctacctgacc     900

taccacgacg cgggcatcgc tagggcgctt ggcatagact tcaacaccgt tcaactaaac     960

atgggggtac aggcgataaa catcggcgag ttcgtaagcc tgacccagca gaccatcatt    1020

tcgctccagc gggagttcgc tagcgcggcc aacctctacc tcatccccaa gctagtgctt    1080

cccaactggc cgagcgctac tcgctttcct aggctcacct ttgagatgga ggagcgcaac    1140

gacttctccg ccgcggccaa ccttatgggc atgctcatca acgcggttaa ggactccgaa    1200

gacattccca ccgagctcaa ggcgctaata gacgctctgc ctagcaagat gcgccgggcg    1260

cttggcgtgg tggacgaggt gagggaagcg gtacgccaac ccgccgatta a             1311
```

<210> SEQ ID NO 29
<211> LENGTH: 424
<212> TYPE: PRT
<213> ORGANISM: Artificial Sequence
<220> FEATURE:
<223> OTHER INFORMATION: SIN1

<400> SEQUENCE: 29

```
Gly Pro Ala Lys Leu Glu Gly Ala Ser Val Pro Val Met Ser Thr Ser
1               5                   10                  15

Tyr Asp Val Val Val Asp Arg Glu Phe Asp Glu Gly Thr Pro Gly Ser
            20                  25                  30

Arg Gly Leu Leu Gln Gly Lys Asp Gly Leu Leu Val Tyr His Lys Met
        35                  40                  45

Leu Ser Asp Gly Thr Val Lys Asn Ala Leu Asn Tyr Ile Phe Gly Arg
    50                  55                  60

Ile Arg Ser Ala Lys Trp Tyr Val Glu Pro Ala Ser Thr Asp Pro Glu
65                  70                  75                  80

Asp Ile Ala Ile Ala Ala Phe Ile His Ala Gln Leu Gly Ile Asp Asp
                85                  90                  95

Ala Ser Val Gly Lys Tyr Pro Phe Gly Arg Leu Phe Ala Ile Tyr Glu
            100                 105                 110

Asn Ala Tyr Ile Tyr Gly Met Ala Ala Gly Glu Ile Val Leu Thr Leu
        115                 120                 125

Gly Ala Asp Gly Lys Leu Ile Leu Asp Lys Ile Val Pro Ile His Pro
    130                 135                 140

Phe Asn Ile Asp Glu Val Leu Tyr Asp Glu Glu Gly Gly Pro Lys Ala
145                 150                 155                 160

Leu Lys Leu Ser Gly Glu Val Lys Gly Gly Ser Gln Phe Val Ser Gly
                165                 170                 175

Leu Glu Ile Pro Ile Trp Lys Thr Val Val Phe Leu His Asn Asp Asp
            180                 185                 190

Gly Ser Phe Thr Gly Gln Ser Ala Leu Arg Ala Ala Val Pro His Trp
        195                 200                 205

Leu Ala Lys Arg Ala Leu Ile Leu Leu Ile Asn His Gly Leu Glu Arg
    210                 215                 220

Phe Met Ile Gly Val Pro Thr Leu Thr Ile Pro Lys Ser Val Arg Gln
225                 230                 235                 240

Gly Thr Lys Gln Trp Glu Ala Ala Lys Glu Ile Val Lys Asn Phe Val
                245                 250                 255

Gln Lys Pro Arg His Gly Ile Ile Leu Pro Asn Asp Trp Lys Phe Asn
            260                 265                 270

Thr Val Asn Leu Lys Ser Ala Met Pro Asn Ala Ile Pro Tyr Leu Thr
        275                 280                 285

Tyr His Asp Ala Gly Ile Ala Arg Ala Leu Gly Ile Asp Phe Asn Thr
    290                 295                 300

Val Gln Leu Asn Met Gly Val Gln Ala Ile Asn Ile Gly Glu Phe Val
305                 310                 315                 320

Ser Leu Thr Gln Gln Thr Ile Ile Ser Leu Gln Arg Glu Phe Ala Ser
                325                 330                 335

Ala Val Asn Leu Tyr Leu Ile Pro Lys Leu Val Leu Pro Asn Trp Pro
            340                 345                 350

Ser Ala Thr Arg Phe Pro Arg Leu Thr Phe Glu Met Glu Glu Arg Asn
        355                 360                 365

Asp Phe Ser Ala Ala Ala Asn Leu Met Gly Met Leu Ile Asn Ala Val
    370                 375                 380

Lys Asp Ser Glu Asp Ile Pro Thr Glu Leu Lys Ala Leu Ile Asp Ala
385                 390                 395                 400
```

```
Leu Pro Ser Lys Met Arg Arg Ala Leu Gly Val Val Asp Glu Val Arg
                405                 410                 415

Glu Ala Val Arg Gln Pro Ala Asp
            420


<210> SEQ ID NO 30
<211> LENGTH: 1332
<212> TYPE: DNA
<213> ORGANISM: Artificial Sequence
<220> FEATURE:
<223> OTHER INFORMATION: SIN1

<400> SEQUENCE: 30

atgggcagca gccatcatca tcatcatcac agcagcggcc tggaagttct gttccaggga     60

ccagcaaagc tcgagggcgc ctccgtgccg gtgatgtcca ccagttacga cgtggtggtg    120

gaccgggagt ttgacgaggg tacgccaggt tctcgcggcc tactgcaggg caaggacggc    180

ttgctcgtct accacaagat gctctcggac ggcacggtta agaacgccct caactacatc    240

ttcggacgca tccgctcggc gaagtggtac gtagagcccg cctctaccga cccggaagac    300

atcgccatcg ccgccttcat ccacgcccag ttaggcatag acgacgcttc ggtgggcaag    360

tatccctttg gccgcctttt cgccatctac gaaaacgcct acatatacgg catggccgcc    420

ggggaaatcg tactaaccct tggcgcggac ggcaagctca tccttgacaa aatcgtccct    480

atccaccctt tcaacattga cgaggtgctt tacgacgagg aaggcggtcc aaaggcgcta    540

aagctaagcg gagaggtgaa gggcggaagc cagtttgtga gcgggttgga gattcctata    600

tggaagaccg tggtcttcct gcacaacgac gacggctcct tcaccggaca gagcgccctc    660

agagccgccg tgccgcattg gctagccaaa cgagccctca ttctcctcat caaccacggg    720

ttggagcgct tcatgattgg cgtgcccacc ctcaccatcc ccaagagcgt gcgtcaggga    780

accaagcaat gggaggccgc caaggaaatc gtcaagaact ttgttcaaaa accacggcat    840

ggtataatac tgcctaacga ctggaagttt aacacggtaa acctgaagtc ggccatgccc    900

aacgccattc cctacctgac ctaccacgac gcgggcatcg ctagggcgct tggcatagac    960

ttcaacaccg ttcaactaaa catgggggta caggcgataa acatcggcga gttcgtaagc   1020

ctgacccagc agaccatcat ttcgctccag cgggagttcg ctagcgcggt caacctctac   1080

ctcatcccca agctagtgct tcccaactgg ccgagcgcta ctcgctttcc taggctcacc   1140

tttgagatgg aggagcgcaa cgacttctcc gccgcggcca accttatggg catgctcatc   1200

aacgcggtta aggactccga agacattccc accgagctca aggcgctaat agacgctctg   1260

cctagcaaga tgcgccgggc gcttggcgtg gtggacgagg tgagggaagc ggtacgccaa   1320

cccgccgatt aa                                                       1332


<210> SEQ ID NO 31
<211> LENGTH: 425
<212> TYPE: PRT
<213> ORGANISM: Artificial Sequence
<220> FEATURE:
<223> OTHER INFORMATION: SIN2

<400> SEQUENCE: 31

Gly Pro Ala Lys Leu Glu Gly Ala Ser Val Pro Val Met Ser Thr Ser
1               5                   10                  15

Tyr Asp Val Val Val Asp Arg Glu Phe Asp Glu Gly Arg Lys Leu Pro
            20                  25                  30
```

```
Asp Ala Gly Leu Leu Gln Gly Lys Asp Gly Leu Leu Val Tyr His Lys
        35                  40                  45

Met Leu Ser Asp Gly Thr Val Lys Asn Ala Leu Asn Tyr Ile Phe Gly
    50                  55                  60

Arg Ile Arg Ser Ala Lys Trp Tyr Val Glu Pro Ala Ser Thr Asp Pro
65                  70                  75                  80

Glu Asp Ile Ala Ile Ala Ala Phe Ile His Ala Gln Leu Gly Ile Asp
                85                  90                  95

Asp Ala Ser Val Gly Lys Tyr Pro Phe Gly Arg Leu Phe Ala Ile Tyr
            100                 105                 110

Glu Asn Ala Tyr Ile Tyr Gly Met Ala Ala Gly Glu Ile Val Leu Thr
        115                 120                 125

Leu Gly Ala Asp Gly Lys Leu Ile Leu Asp Lys Ile Val Pro Ile His
    130                 135                 140

Pro Phe Asn Ile Asp Glu Val Leu Tyr Asp Glu Glu Gly Gly Pro Lys
145                 150                 155                 160

Ala Leu Lys Leu Ser Gly Glu Val Lys Gly Gly Ser Gln Phe Val Ser
                165                 170                 175

Gly Leu Glu Ile Pro Ile Trp Lys Thr Val Val Phe Leu His Asn Asp
            180                 185                 190

Asp Gly Ser Phe Thr Gly Gln Ser Ala Leu Arg Ala Ala Val Pro His
        195                 200                 205

Trp Leu Ala Lys Arg Ala Leu Ile Leu Leu Ile Asn His Gly Leu Glu
    210                 215                 220

Arg Phe Met Ile Gly Val Pro Thr Leu Thr Ile Pro Lys Ser Val Arg
225                 230                 235                 240

Gln Gly Thr Lys Gln Trp Glu Ala Ala Lys Glu Ile Val Lys Asn Phe
                245                 250                 255

Val Gln Lys Pro Arg His Gly Ile Ile Leu Pro Asn Asp Trp Lys Phe
            260                 265                 270

Asn Thr Val Asn Leu Lys Ser Ala Met Pro Asn Ala Ile Pro Tyr Leu
        275                 280                 285

Thr Tyr His Asp Ala Gly Ile Ala Arg Ala Leu Gly Ile Asp Phe Asn
    290                 295                 300

Thr Val Gln Leu Asn Met Gly Val Gln Ala Ile Asn Ile Gly Glu Phe
305                 310                 315                 320

Val Ser Leu Thr Gln Gln Thr Ile Ile Ser Leu Gln Arg Glu Phe Ala
                325                 330                 335

Ser Ala Val Asn Leu Tyr Leu Ile Pro Lys Leu Val Leu Pro Asn Trp
            340                 345                 350

Pro Ser Ala Thr Arg Phe Pro Arg Leu Thr Phe Glu Met Glu Glu Arg
        355                 360                 365

Asn Asp Phe Ser Ala Ala Ala Asn Leu Met Gly Met Leu Ile Asn Ala
    370                 375                 380

Val Lys Asp Ser Glu Asp Ile Pro Thr Glu Leu Lys Ala Leu Ile Asp
385                 390                 395                 400

Ala Leu Pro Ser Lys Met Arg Arg Ala Leu Gly Val Val Asp Glu Val
                405                 410                 415

Arg Glu Ala Val Arg Gln Pro Ala Asp
            420                 425
```

<210> SEQ ID NO 32
<211> LENGTH: 1335
<212> TYPE: DNA

<213> ORGANISM: Artificial Sequence
<220> FEATURE:
<223> OTHER INFORMATION: SIN2

<400> SEQUENCE: 32
atgggcagca gccatcatca tcatcatcac agcagcggcc tggaagttct gttccaggga 60
ccagcaaagc tcgagggcgc ctccgtgccg gtgatgtcca ccagttacga cgtggtggtg 120
gaccgggagt ttgacgaggg tcgtaaactg ccggatgcag gcctactgca gggcaaggac 180
ggcttgctcg tctaccacaa gatgctctcg gacggcacgg ttaagaacgc cctcaactac 240
atcttcggac gcatccgctc ggcgaagtgg tacgtagagc ccgcctctac cgacccggaa 300
gacatcgcca tcgccgcctt catccacgcc cagttaggca tagacgacgc ttcggtgggc 360
aagtatccct ttggccgcct tttcgccatc tacgaaaacg cctacatata cggcatggcc 420
gccggggaaa tcgtactaac ccttggcgcg gacggcaagc tcatccttga caaaatcgtc 480
cctatccacc ctttcaacat tgacgaggtg ctttacgacg aggaaggcgg tccaaaggcg 540
ctaaagctaa gcggagaggt gaagggcgga agccagtttg tgagcgggtt ggagattcct 600
atatggaaga ccgtggtctt cctgcacaac gacgacggct ccttcaccgg acagagcgcc 660
ctcagagccg ccgtgccgca ttggctagcc aaacgagccc tcattctcct catcaaccac 720
gggttggagc gcttcatgat tggcgtgccc accctcacca tccccaagag cgtgcgtcag 780
ggaaccaagc aatgggaggc cgccaaggaa atcgtcaaga actttgttca aaaaccacgg 840
catggtataa tactgcctaa cgactggaag tttaacacgg taaacctgaa gtcggccatg 900
cccaacgcca ttccctacct gacctaccac gacgcgggca tcgctagggc gcttggcata 960
gacttcaaca ccgttcaact aaacatgggg gtacaggcga taaacatcgg cgagttcgta 1020
agcctgaccc agcagaccat catttcgctc cagcgggagt tcgctagcgc ggtcaacctc 1080
tacctcatcc ccaagctagt gcttcccaac tggccgagcg ctactcgctt tcctaggctc 1140
acctttgaga tggaggagcg caacgacttc tccgccgcgg ccaaccttat gggcatgctc 1200
atcaacgcgg ttaaggactc cgaagacatt cccaccgagc tcaaggcgct aatagacgct 1260
ctgcctagca agatgcgccg ggcgcttggc gtggtggacg aggtgaggga agcggtacgc 1320
caacccgccg attaa 1335

<210> SEQ ID NO 33
<211> LENGTH: 431
<212> TYPE: PRT
<213> ORGANISM: Artificial Sequence
<220> FEATURE:
<223> OTHER INFORMATION: SIN3

<400> SEQUENCE: 33

Gly Pro Ala Ser Ser Lys Lys Ser Gly Ser Tyr Ser Gly Ser Lys Gly
1 5 10 15

Ser Lys Leu Glu Gly Ala Ser Val Pro Val Met Ser Thr Ser Tyr Asp
20 25 30

Val Val Val Asp Arg Glu Phe Asp Glu Cys Leu Gln Gly Lys Asp Gly
35 40 45

Leu Leu Val Tyr His Lys Met Leu Ser Asp Gly Thr Val Lys Asn Ala
50 55 60

Leu Asn Tyr Ile Phe Gly Arg Ile Arg Ser Ala Lys Trp Tyr Val Glu
65 70 75 80

Pro Ala Ser Thr Asp Pro Glu Asp Ile Ala Ile Ala Ala Phe Ile His
85 90 95

```
Ala Gln Leu Gly Ile Asp Asp Ala Ser Val Gly Lys Tyr Pro Phe Gly
            100                 105                 110

Arg Leu Phe Ala Ile Tyr Glu Asn Ala Tyr Ile Tyr Gly Met Ala Ala
        115                 120                 125

Gly Glu Ile Val Leu Thr Leu Gly Ala Asp Gly Lys Leu Ile Leu Asp
    130                 135                 140

Lys Ile Val Pro Ile His Pro Phe Asn Ile Asp Glu Val Leu Tyr Asp
145                 150                 155                 160

Glu Glu Gly Gly Pro Lys Ala Leu Lys Leu Ser Gly Glu Val Lys Gly
                165                 170                 175

Gly Ser Gln Phe Val Ser Gly Leu Glu Ile Pro Ile Trp Lys Thr Val
            180                 185                 190

Val Phe Leu His Asn Asp Asp Gly Ser Phe Thr Gly Gln Ser Ala Leu
        195                 200                 205

Arg Ala Ala Val Pro His Trp Leu Ala Lys Arg Ala Leu Ile Leu Leu
    210                 215                 220

Ile Asn His Gly Leu Glu Arg Phe Met Ile Gly Val Pro Thr Leu Thr
225                 230                 235                 240

Ile Pro Lys Ser Val Arg Gln Gly Thr Lys Gln Trp Glu Ala Ala Lys
                245                 250                 255

Glu Ile Val Lys Asn Phe Val Gln Lys Pro Arg His Gly Ile Ile Leu
            260                 265                 270

Pro Asn Asp Trp Lys Phe Asn Thr Val Asn Leu Lys Ser Ala Met Pro
        275                 280                 285

Asn Ala Ile Pro Tyr Leu Thr Tyr His Asp Ala Gly Ile Ala Arg Ala
    290                 295                 300

Leu Gly Ile Asp Phe Asn Thr Val Gln Leu Asn Met Gly Val Gln Ala
305                 310                 315                 320

Ile Asn Ile Gly Glu Phe Val Ser Leu Thr Gln Gln Thr Ile Ile Ser
                325                 330                 335

Leu Gln Arg Glu Phe Ala Ser Ala Ala Asn Leu Tyr Leu Ile Pro Lys
            340                 345                 350

Leu Val Leu Pro Asn Trp Pro Ser Ala Thr Arg Phe Pro Arg Leu Thr
        355                 360                 365

Phe Glu Met Glu Glu Arg Asn Asp Phe Ser Ala Ala Ala Asn Leu Met
    370                 375                 380

Gly Met Leu Ile Asn Ala Val Lys Asp Ser Glu Asp Ile Pro Thr Glu
385                 390                 395                 400

Leu Lys Ala Leu Ile Asp Ala Leu Pro Ser Lys Met Arg Arg Ala Leu
                405                 410                 415

Gly Val Val Asp Glu Val Arg Glu Ala Val Arg Gln Pro Ala Asp
            420                 425                 430
```

<210> SEQ ID NO 34
<211> LENGTH: 1353
<212> TYPE: DNA
<213> ORGANISM: Artificial Sequence
<220> FEATURE:
<223> OTHER INFORMATION: SIN3

<400> SEQUENCE: 34

```
atgggcagca gccatcatca tcatcatcac agcagcggcc tggaagttct gttccaggga      60

ccagcaagca gtaagaaaag tggaagctat agcggcagca aaggcagcaa gctcgagggc     120

gcctccgtgc cggtgatgtc caccagttac gacgtggtgg tggaccggga gtttgacgag     180
```

```
tgtctgcagg gcaaggacgg cttgctcgtc taccacaaga tgctctcgga cggcacggtt    240

aagaacgccc tcaactacat cttcggacgc atccgctcgg cgaagtggta cgtagagccc    300

gcctctaccg acccggaaga catcgccatc gccgccttca tccacgccca gttaggcata    360

gacgacgctt cggtgggcaa gtatcccttt ggccgccttt tcgccatcta cgaaaacgcc    420

tacatatacg gcatggccgc cggggaaatc gtactaaccc ttggcgcgga cggcaagctc    480

atccttgaca aaatcgtccc tatccaccct ttcaacattg acgaggtgct ttacgacgag    540

gaaggcggtc caaaggcgct aaagctaagc ggagaggtga agggcggaag ccagtttgtg    600

agcgggttgg agattcctat atggaagacc gtggtcttcc tgcacaacga cgacggctcc    660

ttcaccggac agagcgccct cagagccgcc gtgccgcatt ggctagccaa acgagccctc    720

attctcctca tcaaccacgg gttggagcgc ttcatgattg gcgtgcccac cctcaccatc    780

cccaagagcg tgcgtcaggg aaccaagcaa tgggaggccg ccaaggaaat cgtcaagaac    840

tttgttcaaa aaccacggca tggtataata ctgcctaacg actggaagtt taacacggta    900

aacctgaagt cggccatgcc caacgccatt ccctacctga cctaccacga cgcgggcatc    960

gctagggcgc ttggcataga cttcaacacc gttcaactaa acatgggggt acaggcgata   1020

aacatcggcg agttcgtaag cctgacccag cagaccatca tttcgctcca gcgggagttc   1080

gctagcgcgg ccaacctcta cctcatcccc aagctagtgc ttcccaactg gccgagcgct   1140

actcgctttc ctaggctcac ctttgagatg gaggagcgca acgacttctc cgccgcggcc   1200

aaccttatgg gcatgctcat caacgcggtt aaggactccg aagacattcc caccgagctc   1260

aaggcgctaa tagacgctct gcctagcaag atgcgccggg cgcttggcgt ggtggacgag   1320

gtgagggaag cggtacgcca acccgccgat taa                                1353
```

```
<210> SEQ ID NO 35
<211> LENGTH: 426
<212> TYPE: PRT
<213> ORGANISM: Artificial Sequence
<220> FEATURE:
<223> OTHER INFORMATION: SIN4

<400> SEQUENCE: 35

Gly Pro Ala Lys Leu Glu Gly Ala Ser Val Pro Val Met Ser Thr Ser
1               5                   10                  15

Tyr Asp Val Val Val Asp Arg Glu Phe Asp Glu Gly Tyr Arg Pro Gly
            20                  25                  30

Phe Tyr Phe Arg Leu Leu Gln Gly Lys Asp Gly Leu Leu Val Tyr His
        35                  40                  45

Lys Met Leu Ser Asp Gly Thr Val Lys Asn Ala Leu Asn Tyr Ile Phe
    50                  55                  60

Gly Arg Ile Arg Ser Ala Lys Trp Tyr Val Glu Pro Ala Ser Thr Asp
65                  70                  75                  80

Pro Glu Asp Ile Ala Ile Ala Ala Phe Ile His Ala Gln Leu Gly Ile
                85                  90                  95

Asp Asp Ala Ser Val Gly Lys Tyr Pro Phe Gly Arg Leu Phe Ala Ile
            100                 105                 110

Tyr Glu Asn Ala Tyr Ile Tyr Gly Met Ala Ala Gly Glu Ile Val Leu
        115                 120                 125

Thr Leu Gly Ala Asp Gly Lys Leu Ile Leu Asp Lys Ile Val Pro Ile
    130                 135                 140

His Pro Phe Asn Ile Asp Glu Val Leu Tyr Asp Glu Glu Gly Gly Pro
145                 150                 155                 160
```

```
Lys Ala Leu Lys Leu Ser Gly Glu Val Lys Gly Gly Ser Gln Phe Val
                165                 170                 175

Ser Gly Leu Glu Ile Pro Ile Trp Lys Thr Val Val Phe Leu His Asn
            180                 185                 190

Asp Asp Gly Ser Phe Thr Gly Gln Ser Ala Leu Arg Ala Ala Val Pro
        195                 200                 205

His Trp Leu Ala Lys Arg Ala Leu Ile Leu Leu Ile Asn His Gly Leu
    210                 215                 220

Glu Arg Phe Met Ile Gly Val Pro Thr Leu Thr Ile Pro Lys Ser Val
225                 230                 235                 240

Arg Gln Gly Thr Lys Gln Trp Glu Ala Ala Lys Glu Ile Val Lys Asn
                245                 250                 255

Phe Val Gln Lys Pro Arg His Gly Ile Ile Leu Pro Asn Asp Trp Lys
            260                 265                 270

Phe Asn Thr Val Asn Leu Lys Ser Ala Met Pro Asn Ala Ile Pro Tyr
        275                 280                 285

Leu Thr Tyr His Asp Ala Gly Ile Ala Arg Ala Leu Gly Ile Asp Phe
    290                 295                 300

Asn Thr Val Gln Leu Asn Met Gly Val Gln Ala Ile Asn Ile Gly Glu
305                 310                 315                 320

Phe Val Ser Leu Thr Gln Gln Thr Ile Ile Ser Leu Gln Arg Glu Phe
                325                 330                 335

Ala Ser Ala Val Asn Leu Tyr Leu Ile Pro Lys Leu Val Leu Pro Asn
            340                 345                 350

Trp Pro Ser Ala Thr Arg Phe Pro Arg Leu Thr Phe Glu Met Glu Glu
        355                 360                 365

Arg Asn Asp Phe Ser Ala Ala Ala Asn Leu Met Gly Met Leu Ile Asn
    370                 375                 380

Ala Val Lys Asp Ser Glu Asp Ile Pro Thr Glu Leu Lys Ala Leu Ile
385                 390                 395                 400

Asp Ala Leu Pro Ser Lys Met Arg Arg Ala Leu Gly Val Val Asp Glu
                405                 410                 415

Val Arg Glu Ala Val Arg Gln Pro Ala Asp
            420                 425
```

<210> SEQ ID NO 36
<211> LENGTH: 1338
<212> TYPE: DNA
<213> ORGANISM: Artificial Sequence
<220> FEATURE:
<223> OTHER INFORMATION: SIN4

<400> SEQUENCE: 36

```
atgggcagca gccatcatca tcatcatcac agcagcggcc tggaagttct gttccaggga      60

ccagcaaagc tcgagggcgc ctccgtgccg gtgatgtcca ccagttacga cgtggtggtg     120

gaccgggagt ttgacgaggg atatcgcccg ggcttttatt ttcgcctact gcagggcaag     180

gacggcttgc tcgtctacca caagatgctc tcggacggca cggttaagaa cgccctcaac     240

tacatcttcg gacgcatccg ctcggcgaag tggtacgtag agcccgcctc taccgacccg     300

gaagacatcg ccatcgccgc cttcatccac gcccagttag gcatagacga cgcttcggtg     360

ggcaagtatc cctttggccg ccttttcgcc atctacgaaa acgcctacat atacggcatg     420

gccgccgggg aaatcgtact aacccttggc gcggacggca agctcatcct tgacaaaatc     480

gtccctatcc accctttcaa cattgacgag gtgctttacg acgaggaagg cggtccaaag     540
```

```
gcgctaaagc taagcggaga ggtgaagggc ggaagccagt ttgtgagcgg gttggagatt    600

cctatatgga agaccgtggt cttcctgcac aacgacgacg gctccttcac cggacagagc    660

gccctcagag ccgccgtgcc gcattggcta gccaaacgag ccctcattct cctcatcaac    720

cacgggttgg agcgcttcat gattggcgtg cccaccctca ccatccccaa gagcgtgcgt    780

cagggaacca agcaatggga ggccgccaag gaaatcgtca agaactttgt tcaaaaacca    840

cggcatggta taatactgcc taacgactgg aagtttaaca cggtaaacct gaagtcggcc    900

atgcccaacg ccattcccta cctgacctac cacgacgcgg gcatcgctag ggcgcttggc    960

atagacttca acaccgttca actaaacatg gggtacaggc cgataaacat cggcgagttc   1020

gtaagcctga cccagcagac catcatttcg ctccagcggg agttcgctag cgcggtcaac   1080

ctctacctca tccccaagct agtgcttccc aactggccga gcgctactcg ctttcctagg   1140

ctcacctttg agatggagga gcgcaacgac ttctccgccg cggccaacct tatgggcatg   1200

ctcatcaacg cggttaagga ctccgaagac attcccaccg agctcaaggc gctaatagac   1260

gctctgccta gcaagatgcg ccgggcgctt ggcgtggtgg acgaggtgag ggaagcggta   1320

cgccaacccg ccgattaa                                                 1338
```

<210> SEQ ID NO 37
<211> LENGTH: 445
<212> TYPE: PRT
<213> ORGANISM: Artificial Sequence
<220> FEATURE:
<223> OTHER INFORMATION: 400C

<400> SEQUENCE: 37

```
Met Ala Lys Arg Gly Arg Lys Pro Lys Glu Leu Val Pro Gly Pro Gly
1               5                   10                  15

Ser Ile Asp Pro Ser Asp Val Pro Lys Leu Glu Gly Ala Ser Val Pro
            20                  25                  30

Val Met Ser Thr Ser Tyr Asp Val Val Val Asp Arg Glu Phe Asp Glu
        35                  40                  45

Leu Leu Gln Gly Lys Asp Gly Leu Leu Val Tyr His Lys Met Leu Ser
    50                  55                  60

Asp Gly Thr Val Lys Asn Ala Leu Asn Tyr Ile Phe Gly Arg Ile Arg
65                  70                  75                  80

Ser Ala Lys Trp Tyr Val Glu Pro Ala Ser Thr Asp Pro Glu Asp Ile
                85                  90                  95

Ala Ile Ala Ala Phe Ile His Ala Gln Leu Gly Ile Asp Asp Ala Ser
            100                 105                 110

Val Gly Lys Tyr Pro Phe Gly Arg Leu Phe Ala Ile Tyr Glu Asn Ala
        115                 120                 125

Tyr Ile Tyr Gly Met Ala Ala Gly Glu Ile Val Leu Thr Leu Gly Ala
    130                 135                 140

Asp Gly Lys Leu Ile Leu Asp Lys Ile Val Pro Ile His Pro Phe Asn
145                 150                 155                 160

Ile Asp Glu Val Tyr Asp Glu Glu Gly Gly Pro Lys Ala Leu Lys Leu
                165                 170                 175

Ser Gly Glu Val Lys Gly Gly Ser Gln Phe Val Ser Gly Leu Glu Ile
            180                 185                 190

Pro Ile Trp Lys Thr Val Val Phe Leu His Asn Asp Asp Gly Ser Phe
        195                 200                 205

Thr Gly Gln Ser Ala Leu Arg Ala Ala Val Pro His Trp Leu Ala Lys
    210                 215                 220
```

```
Arg Ala Leu Ile Leu Leu Ile Asn His Gly Leu Glu Arg Phe Met Ile
225                 230                 235                 240

Gly Val Pro Thr Leu Thr Ile Pro Lys Ser Val Arg Gln Gly Thr Lys
                245                 250                 255

Gln Trp Glu Ala Ala Lys Glu Ile Val Lys Asn Phe Val Gln Lys Pro
            260                 265                 270

Arg His Gly Ile Ile Leu Pro Asp Asp Trp Lys Phe Asp Thr Val Asp
        275                 280                 285

Leu Lys Ser Ala Met Pro Asp Ala Ile Pro Tyr Leu Thr Tyr His Asp
    290                 295                 300

Ala Gly Ile Ala Arg Ala Leu Gly Ile Asp Phe Asn Thr Val Gln Leu
305                 310                 315                 320

Asn Met Gly Val Gln Ala Ile Asn Ile Gly Glu Phe Val Ser Leu Thr
                325                 330                 335

Gln Gln Thr Ile Ile Ser Leu Gln Arg Glu Phe Ala Ser Ala Val Asn
            340                 345                 350

Leu Tyr Leu Ile Pro Lys Leu Val Leu Pro Asn Trp Pro Ser Ala Thr
        355                 360                 365

Arg Phe Pro Arg Leu Thr Phe Glu Met Glu Glu Arg Asn Asp Phe Ser
    370                 375                 380

Ala Ala Ala Asn Leu Met Gly Met Leu Ile Asn Ala Val Lys Cys Ser
385                 390                 395                 400

Glu Asp Ile Pro Thr Glu Leu Lys Ala Leu Ile Asp Ala Leu Pro Ser
                405                 410                 415

Lys Met Arg Arg Ala Leu Gly Val Val Asp Glu Val Arg Glu Ala Val
            420                 425                 430

Arg Gln Pro Ala Asp Leu Glu His His His His His His
        435                 440                 445
```

<210> SEQ ID NO 38
<211> LENGTH: 1341
<212> TYPE: DNA
<213> ORGANISM: Artificial Sequence
<220> FEATURE:
<223> OTHER INFORMATION: 400C
<220> FEATURE:
<221> NAME/KEY: misc_feature
<222> LOCATION: 494
<223> OTHER INFORMATION: n = A,T,C or G

<400> SEQUENCE: 38

```
atggctaagc gaggacgtaa acccaaagag ctggtccccg gacctggctc cattgaccca     60

tctgacgttc ccaagctcga gggcgcctcc gtgccggtga tgtccaccag ttacgacgtg    120

gtggtggacc gggagtttga cgagctactg cagggcaagg acggcttgct cgtctaccac    180

aagatgctct cggacggcac ggttaagaac gccctcaact acatcttcgg acgcatccgc    240

tcggcgaagt ggtacgtaga gcccgcctct accgacccgg aagacatcgc catcgccgcc    300

ttcatccacg cccagttagg catagacgac gcttcggtgg gcaagtatcc ctttggccgc    360

cttttcgcca tctacgaaaa cgcctacata tacggcatgg ccgccgggga aatcgtacta    420

acccttggcg cggacggcaa gctcatcctt gacaaaatcg tccctatcca ccctttcaac    480

attgacgagg tgcnttacga cgaggaaggc ggtccaaagg cgctaaagct aagcggagag    540

gtgaagggcg gaagccagtt tgtgagcggg ttggagattc ctatatggaa gaccgtggtc    600

ttcctgcaca acgacgacgg ctccttcacc ggacagagcg ccctcagagc cgccgtgccg    660

cattggctag ccaaacgagc cctcattctc ctcatcaacc acgggttgga gcgcttcatg    720
```

-continued

```
attggcgtgc ccaccctcac catccccaag agcgtgcgtc agggaaccaa gcaatgggag    780

gccgccaagg aaatcgtcaa gaactttgtt caaaaaccac ggcatggtat aatactgcct    840

gacgactgga agtttgacac ggtagacctg aagtcggcca tgcccgacgc cattccctac    900

ctgacctacc acgacgcggg catcgctagg gcgcttggca tagacttcaa caccgttcaa    960

ctaaacatgg gggtacaggc gataaacatc ggcgagttcg taagcctgac ccagcagacc   1020

atcatttcgc tccagcggga gttcgctagc gcggtcaacc tctacctcat ccccaagcta   1080

gtgcttccca actggccgag cgctactcgc tttcctaggc tcacctttga gatggaggag   1140

cgcaacgact tctccgccgc ggccaacctt atgggcatgc tcatcaacgc ggttaagtgc   1200

tccgaagaca ttcccaccga gctcaaggcg ctaatagacg ctctgcctag caagatgcgc   1260

cgggcgcttg gcgtggtgga cgaggtgagg gaagcggtac gccaacccgc cgatctcgag   1320

caccaccacc accaccactg a                                              1341
```

<210> SEQ ID NO 39
<211> LENGTH: 436
<212> TYPE: PRT
<213> ORGANISM: Artificial Sequence
<220> FEATURE:
<223> OTHER INFORMATION: Thermus Thermophilus Bacteriophage G20C and Affinity Tag; WT Nanopore

<400> SEQUENCE: 39

```
Met Gly Ser Ser His His His His His His Ser Ser Gly Leu Glu Val
1               5                   10                  15

Leu Phe Gln Gly Pro Ala Lys Leu Glu Gly Ala Ser Val Pro Val Met
            20                  25                  30

Ser Thr Ser Tyr Asp Val Val Val Asp Arg Glu Phe Asp Glu Leu Leu
        35                  40                  45

Gln Gly Lys Asp Gly Leu Leu Val Tyr His Lys Met Leu Ser Asp Gly
    50                  55                  60

Thr Val Lys Asn Ala Leu Asn Tyr Ile Phe Gly Arg Ile Arg Ser Ala
65                  70                  75                  80

Lys Trp Tyr Val Glu Pro Ala Ser Thr Asp Pro Glu Asp Ile Ala Ile
                85                  90                  95

Ala Ala Phe Ile His Ala Gln Leu Gly Ile Asp Asp Ala Ser Val Gly
            100                 105                 110

Lys Tyr Pro Phe Gly Arg Leu Phe Ala Ile Tyr Glu Asn Ala Tyr Ile
        115                 120                 125

Tyr Gly Met Ala Ala Gly Glu Ile Val Leu Thr Leu Gly Ala Asp Gly
    130                 135                 140

Lys Leu Ile Leu Asp Lys Ile Val Pro Ile His Pro Phe Asn Ile Asp
145                 150                 155                 160

Glu Val Leu Tyr Asp Glu Glu Gly Gly Pro Lys Ala Leu Lys Leu Ser
                165                 170                 175

Gly Glu Val Lys Gly Gly Ser Gln Phe Val Ser Gly Leu Glu Ile Pro
            180                 185                 190

Ile Trp Lys Thr Val Val Phe Leu His Asn Asp Asp Gly Ser Phe Thr
        195                 200                 205

Gly Gln Ser Ala Leu Arg Ala Ala Val Pro His Trp Leu Ala Lys Arg
    210                 215                 220

Ala Leu Ile Leu Leu Ile Asn His Gly Leu Glu Arg Phe Met Ile Gly
225                 230                 235                 240
```

```
Val Pro Thr Leu Thr Ile Pro Lys Ser Val Arg Gln Gly Thr Lys Gln
                245                 250                 255

Trp Glu Ala Ala Lys Glu Ile Val Lys Asn Phe Val Gln Lys Pro Arg
            260                 265                 270

His Gly Ile Ile Leu Pro Asp Asp Trp Lys Phe Asp Thr Val Asp Leu
        275                 280                 285

Lys Ser Ala Met Pro Asp Ala Ile Pro Tyr Leu Thr Tyr His Asp Ala
    290                 295                 300

Gly Ile Ala Arg Ala Leu Gly Ile Asp Phe Asn Thr Val Gln Leu Asn
305                 310                 315                 320

Met Gly Val Gln Ala Ile Asn Ile Gly Glu Phe Val Ser Leu Thr Gln
                325                 330                 335

Gln Thr Ile Ile Ser Leu Gln Arg Glu Phe Ala Ser Ala Val Asn Leu
            340                 345                 350

Tyr Leu Ile Pro Lys Leu Val Leu Pro Asn Trp Pro Ser Ala Thr Arg
        355                 360                 365

Phe Pro Arg Leu Thr Phe Glu Met Glu Glu Arg Asn Asp Phe Ser Ala
    370                 375                 380

Ala Ala Asn Leu Met Gly Met Leu Ile Asn Ala Val Lys Asp Ser Glu
385                 390                 395                 400

Asp Ile Pro Thr Glu Leu Lys Ala Leu Ile Asp Ala Leu Pro Ser Lys
                405                 410                 415

Met Arg Arg Ala Leu Gly Val Val Asp Glu Val Arg Glu Ala Val Arg
            420                 425                 430

Gln Pro Ala Asp
        435


<210> SEQ ID NO 40
<211> LENGTH: 448
<212> TYPE: PRT
<213> ORGANISM: Thermus thermophilus bacteriophage P23-45

<400> SEQUENCE: 40

Met Ala Lys Arg Gly Arg Lys Pro Lys Glu Leu Val Pro Gly Pro Gly
1               5                   10                  15

Ser Ile Asp Pro Ser Asp Val Pro Lys Leu Glu Gly Ala Ser Val Pro
            20                  25                  30

Val Met Ser Thr Ser Tyr Asp Val Val Val Asp Arg Glu Phe Asp Glu
        35                  40                  45

Leu Leu Gln Gly Lys Asp Gly Leu Leu Val Tyr His Lys Met Leu Ser
    50                  55                  60

Asp Gly Thr Val Lys Asn Ala Leu Asn Tyr Ile Phe Gly Arg Ile Arg
65                  70                  75                  80

Ser Ala Lys Trp Tyr Val Glu Pro Ala Ser Thr Asp Pro Glu Asp Ile
                85                  90                  95

Ala Ile Ala Ala Phe Ile His Ala Gln Leu Gly Ile Asp Asp Ala Ser
            100                 105                 110

Val Gly Lys Tyr Pro Phe Gly Arg Leu Phe Ala Ile Tyr Glu Asn Ala
        115                 120                 125

Tyr Ile Tyr Gly Met Ala Ala Gly Glu Ile Val Leu Thr Leu Gly Ala
    130                 135                 140

Asp Gly Lys Leu Ile Leu Asp Lys Ile Val Pro Ile His Pro Phe Asn
145                 150                 155                 160

Ile Asp Glu Val Leu Tyr Asp Glu Glu Gly Gly Pro Lys Ala Leu Lys
                165                 170                 175
```

```
Leu Ser Gly Glu Val Lys Gly Gly Ser Gln Phe Val Asn Gly Leu Glu
            180                 185                 190

Ile Pro Ile Trp Lys Thr Val Val Phe Leu His Asn Asp Asp Gly Ser
        195                 200                 205

Phe Thr Gly Gln Ser Ala Leu Arg Ala Ala Val Pro His Trp Leu Ala
    210                 215                 220

Lys Arg Ala Leu Ile Leu Leu Ile Asn His Gly Leu Glu Arg Phe Met
225                 230                 235                 240

Ile Gly Val Pro Thr Leu Thr Ile Pro Lys Ser Val Arg Gln Gly Thr
                245                 250                 255

Lys Gln Trp Glu Ala Ala Lys Glu Ile Val Lys Asn Phe Val Gln Lys
            260                 265                 270

Pro Arg His Gly Ile Ile Leu Pro Asp Asp Trp Lys Phe Asp Thr Val
        275                 280                 285

Asp Leu Lys Ser Ala Met Pro Asp Ala Ile Pro Tyr Leu Thr Tyr His
    290                 295                 300

Asp Ala Gly Ile Ala Arg Ala Leu Gly Ile Asp Phe Asn Thr Val Gln
305                 310                 315                 320

Leu Asn Met Gly Val Gln Ala Val Asn Ile Gly Glu Phe Val Ser Leu
                325                 330                 335

Thr Gln Gln Thr Ile Ile Ser Leu Gln Arg Glu Phe Ala Ser Ala Val
            340                 345                 350

Asn Leu Tyr Leu Ile Pro Lys Leu Val Leu Pro Asn Trp Pro Gly Ala
        355                 360                 365

Thr Arg Phe Pro Arg Leu Thr Phe Glu Met Glu Glu Arg Asn Asp Phe
    370                 375                 380

Ser Ala Ala Ala Asn Leu Met Gly Met Leu Ile Asn Ala Val Lys Asp
385                 390                 395                 400

Ser Glu Asp Ile Pro Thr Glu Leu Lys Ala Leu Ile Asp Ala Leu Pro
                405                 410                 415

Ser Lys Met Arg Arg Ala Leu Gly Val Val Asp Glu Val Arg Glu Ala
            420                 425                 430

Val Arg Gln Pro Ala Asp Ser Arg Tyr Leu Tyr Thr Arg Arg Arg Arg
        435                 440                 445
```

<210> SEQ ID NO 41
<211> LENGTH: 1347
<212> TYPE: DNA
<213> ORGANISM: Thermus thermophilus bacteriophage P23-45

<400> SEQUENCE: 41

```
atggctaagc gaggacgtaa acccaaggag ctggtccccg gacctggctc cattgaccca     60

tccgacgttc ccaagctcga gggcgcctcc gtgccggtga tgtccaccag ctacgacgtg    120

gtggttgacc gggagtttga cgagctactg cagggcaagg acggcctgct cgtctaccac    180

aagatgctct cggacggcac ggtcaagaac gccctcaact acatcttcgg gcgcatccgc    240

tcggcgaagt ggtacgtaga gcccgcctct accgacccgg aggacatcgc catcgccgcc    300

ttcatccacg cccagttagg catagacgat gcttcggtag gcaagtatcc ttttggccgt    360

cttttcgcca tctacgaaaa cgcctacata tacggcatgg ccgccgggga aatcgtactg    420

acccttggcg cggacggcaa gctcatcctt gacaaaatcg tccctatcca ccctttcaac    480

attgacgagg tgctttacga cgaggaaggc ggtccaaagg cgctaaagct aagcggagag    540

gtgaagggcg gaagccagtt cgtgaacggg ctggagattc ctatctggaa gaccgtggtc    600
```

-continued

```
ttcctgcaca acgacgacgg ctccttcacc ggacagagcg ccctcagagc cgccgttccg    660
cattggctag ccaaacgcgc ccttatcctc ctcatcaacc acgggctaga gcgcttcatg    720
attggcgtgc ccaccctcac catccccaag agcgtgcgtc aggggaccaa gcaatgggag    780
gccgccaagg aaatcgtcaa gaactttgtt caaaaaccac ggcatggtat aatactgcct    840
gacgactgga agtttgacac ggtagacctg aagtcggcca tgcccgacgc cattccctac    900
ctgacctacc acgacgcggg catcgctagg gcgcttggca tagacttcaa caccgttcag    960
ctaaacatgg gggtacaggc ggtcaacatc ggcgagttcg taagcctgac ccagcagacc   1020
atcatttcgc tccagcggga gttcgctagc gcggtcaacc tctacctcat ccccaagcta   1080
gtgcttccca actggccggg cgccacccgc tttcccaggc tcacctttga gatggaggag   1140
cgtaacgact tctccgccgc ggccaacctt atgggcatgc tcatcaacgc ggttaaggac   1200
tccgaagaca ttcccaccga gctcaaggcg ctaatagacg ctctgcccag caagatgcgc   1260
cgggcgcttg gcgtggtgga cgaggtgagg gaagcggtac gccaacccgc cgattcccgc   1320
tacctgtaca cgcgaaggag gaggtag                                       1347
```

LIPID-FREE ANCHORING OF THERMOPHILIC BACTERIOPHAGE G20C PORTAL ADAPTER INTO SOLID-STATE NANOPORES

RELATED APPLICATIONS

This application is a continuation of U.S. application Ser. No. 16/416,139, filed on May 17, 2019, which claims the benefit of U.S. Provisional Application No. 62/673,118, filed on May 17, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 52002223004_SEQUENCELISTING.txt; created Jun. 27, 2022, 110,592 Bytes in size.

GOVERNMENT SUPPORT

This invention was made with government support under Grant No. 1645671 awarded by the National Science Foundation. The government has certain rights in the invention.

BACKGROUND

Nanopore-based sensors are advancing the sensitivity and selectivity of single-molecule detection in molecular medicine and biotechnology. Conventional electrical and electro-optical sensing devices are based on either membrane protein pores supported in planar lipid bilayers or solid-state pores drilled into thin metallic membranes. While both types of nanosensors have been used in a variety of applications, each has inherent disadvantages that limit their use.

SUMMARY

Hybrid nanopores in accordance with an embodiment of the invention, comprising a protein pore supported within a solid-state membrane, combine the robust nature of solid-state membranes with the easily tunable and precise engineering of protein nanopores. A lipid-free hybrid nanopore comprises a water soluble and stable, modified portal protein of the *Thermus thermophilus* bacteriophage G20c, electrokinetically inserted into a larger nanopore in a solid-state membrane. The hybrid pore is stable and easy to fabricate, and exhibits low peripheral leakage, allowing sensing and discrimination among different types of biomolecules.

In one embodiment according to the invention, there is provided a sensor. The sensor comprises: a solid-state matrix comprising a solid-state pore opening; and a hydrophilic protein channel in a stable insertion fit within the solid-state pore opening, the hydrophilic protein channel comprising a protein nanopore channel.

In further, related embodiments, a protein forming at least part of the hydrophilic protein channel may comprise a modification of an amino acid sequence comprising SEQ ID NO: 1, the modification comprising one or more of: (i) a modification of an upper internal surface residue or a lower internal surface residue of the protein of the hydrophilic protein channel, the modification comprising an alteration of an electrostatic surface potential of an upper internal surface or a lower internal surface of SEQ ID NO: 1; (ii) a modification comprising an insertion of a cysteine residue into SEQ ID NO: 1 or a replacement of an amino acid residue of SEQ ID NO: 1 with a cysteine residue; (iii) a modification of a tunnel loop residue of the protein of the hydrophilic protein channel, the modification comprising an expansion of a narrowest constriction of a tunnel loop of SEQ ID NO: 1, a restriction of the narrowest constriction of the tunnel loop of SEQ ID NO: 1, or a removal of the narrowest constriction of the tunnel loop of SEQ ID NO: 1; (iv) a modification of a tunnel loop residue of the protein of the hydrophilic protein channel, the modification resulting in an alteration of an electrostatic charge property of a tunnel loop of SEQ ID NO: 1; (v) a modification which alters an external charge of the protein of the hydrophilic protein channel; (vi) a modification which promotes binding of the protein of the hydrophilic protein channel to the solid-state matrix; (vii) a modification which extends an N-terminus or a C-terminus of SEQ ID NO: 1 or an N-terminus or a C-terminus of a cleaved portion of SEQ ID NO: 1; and (viii) a deletion of an amino acid residue of at least one of a C-terminal region and an N-terminal region of SEQ ID NO: 1. The modification of SEQ ID NO: 1 may comprise a modification of a lower internal surface residue of the protein of the hydrophilic protein channel, the modification comprising the alteration of the electrostatic surface potential of the lower internal surface of SEQ ID NO: 1, and the protein of the hydrophilic protein channel may comprise SEQ ID NO: 27. The modification of SEQ ID NO: 1 may comprises a replacement of an amino acid residue of SEQ ID NO: 1 with a cysteine residue, and the protein of the hydrophilic protein channel may comprise SEQ ID NO: 11 or SEQ ID NO: 37. The modification of SEQ ID NO: 1 may comprise a modification of the tunnel loop residue of the protein of the hydrophilic protein channel, the modification comprising the expansion of the narrowest constriction of the tunnel loop of SEQ ID NO: 1, the restriction of the narrowest constriction of the tunnel loop of SEQ ID NO: 1, or the removal of the narrowest constriction of the tunnel loop of SEQ ID NO: 1, and the protein of the hydrophilic protein channel may comprise one of: SEQ ID NO: 15, SEQ ID NO: 17, SEQ ID NO: 21, SEQ ID NO: 23 and SEQ ID NO: 25. The modification of SEQ ID NO: 1 may comprise the modification in a tunnel loop residue of the protein of the hydrophilic protein channel, the modification resulting in the alteration of the electrostatic charge property of the tunnel loop of SEQ ID NO: 1, and the protein of the hydrophilic protein channel may comprise SEQ ID NO: 19. The modification of SEQ ID NO: 1 may comprise the modification which alters an external charge of the hydrophilic protein channel, and the protein of the hydrophilic protein channel may comprise one of: SEQ ID NO: 9 and SEQ ID NO: 13. The modification of SEQ ID NO: 1 may comprise the modification which promotes binding of the hydrophilic protein channel to the solid-state matrix, and the protein of the hydrophilic protein channel may comprise one of: SEQ ID NO: 29, SEQ ID NO: 31 and SEQ ID NO: 35. The modification of SEQ ID NO: 1 may comprise the modification which extends the N-terminus of the cleaved portion of SEQ ID NO: 1, and the protein of the hydrophilic protein channel may comprise SEQ ID NO: 33. The modification of SEQ ID NO: 1 may comprise the deletion of an amino acid residue of at least one of the C-terminal region and the N-terminal region of SEQ ID NO: 1, and the modification may comprise a modification of one of: SEQ ID NO: 3, SEQ ID NO: 5 and SEQ ID NO: 7. The protein of the hydrophilic protein channel may comprise a modification of SEQ ID NO: 1, the modification comprising a modification in one or more of: a wing loop residue, a tunnel loop residue, an upper internal surface residue, a lower internal surface residue, an external surface residue, a C-terminal residue, and an N-terminal residue.

In other related embodiments, the sensor may further comprise a voltage source configured to apply a voltage to an electrolyte solution on both sides of the solid-state matrix. The solid-state matrix may comprise at least one of: silicon, hafnium and nickel. The solid-state matrix may comprise at least one of: a silicon containing nitride, a silicon containing carbide and a silicon containing oxide. The solid-state matrix may comprise a thickness of less than about 30 nm. The solid-state pore opening may comprise a diameter of between about 5.4 nm and about 6 nm. The sensor may further comprise a coating on the solid-state matrix to promote binding of the solid-state matrix to a protein forming at least part of the hydrophilic protein channel. The coating may comprise a thiol-coupling compound; and may comprise a maleimide compound.

In other related embodiments, a protein forming at least part of the hydrophilic protein channel may comprise a modification of an amino acid sequence comprising SEQ ID NO: 1, the modification comprising one or more of: a modification of residue 328 of SEQ ID NO: 1, a modification of residue 189 of SEQ ID NO: 1, and a modification of residue 367 of SEQ ID NO: 1. A protein forming at least part of the hydrophilic protein channel may comprise a modification of SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7. A protein forming at least part of the hydrophilic protein channel may comprise a modification of SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In some embodiments, where reference is made to modifications of SEQ ID NO: 1, it will be appreciated that a modification of a portal protein of the *Thermus thermophilus* bacteriophage G20c, can be used, or a modification of a portal protein from other bacteriophages (including other bacteriophages of *Thermus thermophilus*, and other bacteriophages) can be used. In one example, the portal protein of the *Thermus thermophilus* bacteriophage P23-45, or modifications of that portal protein, can be used. Likewise, in some embodiments, where reference is made to modification of SEQ ID NO: 2, it will be appreciated that other modifications of nucleic acids encoding for a portal protein of the *Thermus thermophilus* bacteriophage G20c, can be used, or those encoding for a modification of a portal protein from other bacteriophages (including other bacteriophages of *Thermus thermophilus*, and other bacteriophages) can be used. In one example, modifications of nucleic acids encoding for the portal protein of the *Thermus thermophilus* bacteriophage P23-45, or modifications of that portal protein, can be used.

In another embodiment according to the invention, there is provided a protein variant, the protein variant comprising a modification of an amino acid sequence comprising SEQ ID NO: 1, the modification comprising one or more of: (i) a modification of an upper internal surface residue or a lower internal surface residue of the protein variant, the modification comprising an alteration of an electrostatic surface potential of an upper internal surface or a lower internal surface of SEQ ID NO: 1; (ii) a modification comprising an insertion of a cysteine residue into SEQ ID NO: 1 or a replacement of an amino acid residue of SEQ ID NO: 1 with a cysteine residue; (iii) a modification of a tunnel loop residue of the protein variant, the modification comprising an expansion of a narrowest constriction of a tunnel loop of SEQ ID NO: 1, a restriction of the narrowest constriction of the tunnel loop of SEQ ID NO: 1, or a removal of the narrowest constriction of the tunnel loop of SEQ ID NO: 1; (iv) a modification of a tunnel loop residue of the protein variant, the modification resulting in an alteration of an electrostatic charge property of a tunnel loop of SEQ ID NO: 1; (v) a modification which alters an external charge of the protein variant; (vi) a modification which promotes binding of the protein variant to a solid-state matrix; (vii) a modification which extends an N-terminus or a C-terminus of SEQ ID NO: 1 or an N-terminus or a C-terminus of a cleaved portion of SEQ ID NO: 1; and (viii) a deletion of an amino acid residue of at least one of a C-terminal region and an N-terminal region of SEQ ID NO: 1.

In further, related embodiments, the modification of SEQ ID NO: 1 may comprise a modification of a lower internal surface residue of the protein variant, the modification comprising the alteration of the electrostatic surface potential of the lower internal surface of SEQ ID NO: 1, and the protein variant may comprise SEQ ID NO: 27. The modification of SEQ ID NO: 1 may comprise a replacement of an amino acid residue of SEQ ID NO: 1 with a cysteine residue, and the protein variant may comprise SEQ ID NO: 11 or SEQ ID NO: 37. The modification of SEQ ID NO: 1 may comprise a modification of the tunnel loop residue of the protein variant, the modification comprising the expansion of a narrowest constriction of a tunnel loop of SEQ ID NO: 1, the restriction of the narrowest constriction of the tunnel loop of SEQ ID NO: 1, or the removal of the narrowest constriction of the tunnel loop of SEQ ID NO: 1, and the protein variant may comprise one of: SEQ ID NO: 15, SEQ ID NO: 17, SEQ ID NO: 21, SEQ ID NO: 23, and SEQ ID NO: 25. The modification of SEQ ID NO: 1 may comprise the modification of a tunnel loop residue of the protein variant, the modification resulting in the alteration of the electrostatic charge property of the tunnel loop of SEQ ID NO: 1, and the protein variant may comprise SEQ ID NO: 19. The modification of SEQ ID NO: 1 may comprise the modification which alters the external charge of the protein variant, and the protein variant may comprise one of: SEQ ID NO: 9 and SEQ ID NO: 13. The modification of SEQ ID NO: 1 may comprise the modification which promotes binding of the protein variant to a solid-state matrix, and the protein variant may comprise one of: SEQ ID NO: 29, SEQ ID NO: 31 and SEQ ID NO: 35. The modification of SEQ ID NO: 1 may comprise the modification which extends the N-terminus of the cleaved portion of SEQ ID NO: 1, and the protein variant may comprise SEQ ID NO: 33. The modification of SEQ ID NO: 1 may comprise the deletion of an amino acid residue of at least one of the C-terminal region and the N-terminal region of SEQ ID NO: 1, and the modification may comprise a modification of one of: SEQ ID NO: 3, SEQ ID NO: 5 and SEQ ID NO: 7. The modification of SEQ ID NO: 1 may comprise a modification in one or more of: a wing loop residue, a tunnel loop residue, an upper internal surface residue, a lower internal surface residue, an external surface residue, a C-terminal residue, and an N-terminal residue.

In another embodiment according to the invention, there is provided a protein variant, the protein variant comprising a modification of an amino acid sequence comprising SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In another embodiment according to the invention, there is provided a protein variant, the protein variant comprising a modification of an amino acid sequence comprising SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In another embodiment according to the invention, there is provided a nucleic acid molecule comprising a modification of a nucleic acid sequence of SEQ ID NO: 2, the modification comprising one or more of: (i) a modification in a portion of the nucleic acid sequence that encodes an upper internal surface residue or a lower internal surface residue of a protein encoded by the nucleic acid sequence, the modification producing an alteration of an electrostatic surface potential of an upper internal surface or a lower internal surface of the protein encoded by the nucleic acid sequence; (ii) a modification comprising an insertion of a cysteine residue into a protein encoded by the nucleic acid sequence or a replacement of an amino acid residue of a protein encoded by the nucleic acid sequence with a cysteine residue; (iii) a modification to produce a modification of a tunnel loop residue of a protein encoded by the nucleic acid sequence, the modification in the tunnel loop residue comprising an expansion of a narrowest constriction of a tunnel loop of the protein encoded by the nucleic acid sequence, a restriction of the narrowest constriction of the tunnel loop of the protein encoded by the nucleic acid sequence, or a removal of the narrowest constriction of the tunnel loop of the protein encoded by the nucleic acid sequence; (iv) a modification to produce a modification of a tunnel loop residue of a protein encoded by the nucleic acid sequence, the modification resulting in an alteration of an electrostatic charge property of a tunnel loop of the protein encoded by the nucleic acid sequence; (v) a modification which alters an external charge of a protein encoded by the nucleic acid sequence; (vi) a modification which promotes binding of a protein encoded by the nucleic acid sequence to a solid-state matrix; (vii) a modification which extends an N-terminus or a C-terminus of a protein encoded by the nucleic acid sequence or an N-terminus or a C-terminus of a cleaved portion of the protein encoded by the nucleic acid sequence; and (viii) a deletion of an amino acid residue of at least one of a C-terminal region and an N-terminal region of a protein encoded by the nucleic acid sequence.

In further, related embodiments, the modification of SEQ ID NO: 2 may comprise a modification in the portion of the nucleic acid sequence that encodes the lower internal surface residue of the protein encoded by the nucleic acid sequence, the modification producing the alteration of the electrostatic surface potential of the lower internal surface of the protein encoded by the nucleic acid sequence, and the nucleic acid molecule may comprise SEQ ID NO: 28. The modification of SEQ ID NO: 2 may comprise the modification comprising an insertion of a cysteine residue into a protein encoded by the nucleic acid sequence or a replacement of an amino acid residue of a protein encoded by the nucleic acid sequence with a cysteine residue, and the nucleic acid molecule may comprise SEQ ID NO: 12 or SEQ ID NO: 38. The modification of SEQ ID NO: 2 may comprise the modification to produce a modification of a tunnel loop residue of the protein encoded by the nucleic acid sequence, the modification in the tunnel loop residue comprising the expansion of the narrowest constriction of the tunnel loop of the protein encoded by the nucleic acid sequence, the restriction of the narrowest constriction of the tunnel loop of the protein encoded by the nucleic acid sequence, or the removal of the narrowest constriction of the tunnel loop of the protein encoded by the nucleic acid sequence, and the nucleic acid molecule may comprise one of: SEQ ID NO: 16, SEQ ID NO: 18, SEQ ID NO: 22, SEQ ID NO: 24 and SEQ ID NO: 26. The modification of SEQ ID NO: 2 may comprise a modification to produce a modification of a tunnel loop residue of the protein encoded by the nucleic acid sequence, the modification resulting in the alteration of the electrostatic charge property of the tunnel loop of the protein encoded by the nucleic acid sequence, and the nucleic acid molecule may comprise SEQ ID NO: 20. The modification of SEQ ID NO: 2 may comprise the modification which alters the external charge of the protein encoded by the nucleic acid sequence, and the nucleic acid molecule may comprise one of: SEQ ID NO: 10 and SEQ ID NO: 14. The modification of SEQ ID NO: 2 may comprise the modification which promotes binding of the protein encoded by the nucleic acid sequence to the solid-state matrix, and the nucleic acid molecule may comprise one of: SEQ ID NO: 30, SEQ ID NO: 32 and SEQ ID NO: 36. The modification of SEQ ID NO: 2 may comprise the modification which extends the N-terminus of the cleaved portion of the protein encoded by the nucleic acid sequence, and the nucleic acid molecule may comprise SEQ ID NO: 34. The modification of SEQ ID NO: 2 may comprise a deletion of an amino acid residue of at least one of the C-terminal region and the N-terminal region of the protein encoded by the nucleic acid sequence, and the nucleic acid molecule may comprise one of: SEQ ID NO: 4, SEQ ID NO: 6 and SEQ ID NO: 8. The modification of SEQ ID NO: 2 may comprise a modification to produce a modification in one or more of: a wing loop residue, a tunnel loop residue, an upper internal surface residue, a lower internal surface residue, an external surface residue, a C-terminal end residue, and an N-terminal end residue; of a protein encoded by the nucleic acid sequence.

In another embodiment according to the invention, there is provided a nucleic acid molecule comprising a modification of a nucleic acid sequence of SEQ ID NO: 2, the nucleic acid molecule comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment according to the invention, there is provided a nucleic acid molecule comprising a modification of a nucleic acid sequence of SEQ ID NO: 2, the nucleic acid molecule comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment according to the invention, there is provided a method of sensing a biomolecule, the method comprising: applying a voltage to an electrolyte on both sides of a solid-state matrix, the solid-state matrix comprising a solid-state pore opening, and a hydrophilic protein channel in a stable insertion fit within the solid-state pore opening, the hydrophilic protein channel comprising a protein nanopore channel; and measuring a voltage change produced by passage of the biomolecule through the protein nanopore channel.

In further, related embodiments, the biomolecule may comprise one or more of: a protein, a nucleic acid, a biopolymer and an organic molecule. The biomolecule may comprise single-stranded DNA, double-stranded DNA or RNA. A protein forming at least part of the hydrophilic protein channel may comprise a modification of an amino acid sequence comprising SEQ ID NO: 1, the modification comprising one or more of: (i) a modification of an upper internal surface residue or a lower internal surface residue of the protein of the hydrophilic protein channel, the modification comprising an alteration of an electrostatic surface potential of an upper internal surface or a lower internal surface of SEQ ID NO: 1; (ii) a modification comprising an insertion of a cysteine residue into SEQ ID NO: 1 or a replacement of an amino acid residue of SEQ ID NO: 1 with a cysteine residue; (iii) a modification of a tunnel loop residue of the protein of the hydrophilic protein channel, the modification comprising an expansion of a narrowest constriction of a tunnel loop of SEQ ID NO: 1, a restriction of the narrowest constriction of the tunnel loop of SEQ ID NO: 1, or a removal of the narrowest constriction of the tunnel loop of SEQ ID NO: 1; (iv) a modification of a tunnel loop residue of the protein of the hydrophilic protein channel, the modification resulting in an alteration of an electrostatic charge property of a tunnel loop of SEQ ID NO: 1; (v) a modification which alters an external charge of the protein of the hydrophilic protein channel; (vi) a modification which promotes binding of the protein of the hydrophilic protein channel to the solid-state matrix; (vii) a modification which extends an N-terminus or a C-terminus of SEQ ID NO: 1 or an N-terminus or a C-terminus of a cleaved portion of SEQ ID NO: 1; and (viii) a deletion of an amino acid residue of at least one of a C-terminal region and an N-terminal region of SEQ ID NO: 1. The modification of SEQ ID NO: 1 may comprise a modification of a lower internal surface residue of the protein of the hydrophilic protein channel, the modification comprising the alteration of the electrostatic surface potential of the lower internal surface of SEQ ID NO: 1, and the protein of the hydrophilic protein channel may comprise SEQ ID NO: 27. The modification of SEQ ID NO: 1 may comprise a replacement of an amino acid residue of SEQ ID NO: 1 with a cysteine residue, and the protein of the hydrophilic protein channel may comprise SEQ ID NO: 11 or SEQ ID NO: 37. The modification of SEQ ID NO: 1 may comprise a modification of the tunnel loop residue of the protein of the hydrophilic protein channel, the modification comprising the expansion of the narrowest constriction of the tunnel loop of SEQ ID NO: 1, the restriction of the narrowest constriction of the tunnel loop of SEQ ID NO: 1, or the removal of the narrowest constriction of the tunnel loop of SEQ ID NO: 1, and the protein of the hydrophilic protein channel may comprise one of: SEQ ID NO: 15, SEQ ID NO: 17, SEQ ID NO: 21, SEQ ID NO: 23, and SEQ ID NO: 25. The modification of SEQ ID NO: 1 may comprise the modification in a tunnel loop residue of the protein of the hydrophilic protein channel, the modification resulting in the alteration of the electrostatic charge property of the tunnel loop of SEQ ID NO: 1, and the protein of the hydrophilic protein channel may comprise SEQ ID NO: 19. The modification of SEQ ID NO: 1 may comprise the modification which alters an external charge of the hydrophilic protein channel, and the protein of the hydrophilic protein channel may comprise one of: SEQ ID NO: 9 and SEQ ID NO: 13. The modification of SEQ ID NO: 1 may comprise the modification which promotes binding of the protein of the hydrophilic protein channel to the solid-state matrix, and the protein of the hydrophilic protein channel may comprises one of: SEQ ID NO: 29, SEQ ID NO: 31 and SEQ ID NO: 35. The modification of SEQ ID NO: 1 may comprise the modification to extend the N-terminal of the cleaved portion of SEQ ID NO: 1, and the protein of the hydrophilic protein channel may comprise SEQ ID NO: 33. The modification of SEQ ID NO: 1 may comprise the deletion of an amino acid residue of at least one of the C-terminal region and the N-terminal region of SEQ ID NO: 1, and the modification may comprise a modification of one of: SEQ ID NO: 3, SEQ ID NO: 5 and SEQ ID NO: 7. The protein of the hydrophilic protein channel may comprise a modification of SEQ ID NO: 1, the modification comprising a modification in one or more of: a wing loop residue, a tunnel loop residue, an upper internal surface residue, a lower internal surface residue, an external surface residue, a C-terminal residue, and an N-terminal residue. A protein forming at least part of the hydrophilic protein channel may comprise a modification of SEQ ID NO: 1, the modification comprising one or more of: a modification of residue 328 of SEQ ID NO: 1, a modification of residue 189 of SEQ ID NO: 1, and a modification of residue 367 of SEQ ID NO: 1. A protein forming at least part of the hydrophilic protein channel may comprise a modification of SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7. A protein forming at least part of the hydrophilic protein channel may comprise a modification of SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In other, related embodiments, the solid-state matrix may comprise at least one of: silicon, hafnium and nickel. The solid-state matrix may comprise at least one of: a silicon containing nitride, a silicon containing carbide and a silicon containing oxide. The solid-state matrix may comprise a thickness of less than about 30 nm. The solid-state pore opening may comprise a diameter of between about 5.4 nm and about 6 nm. The solid-state matrix may comprise a coating to promote binding of the solid-state matrix to a protein forming at least part of the hydrophilic protein channel. The coating may comprise a thiol-coupling compound. The coating may comprise a maleimide compound.

In another embodiment according to the invention, there is provided a method of manufacturing a sensor, the method comprising: applying at least one of a voltage and a pressure to an electrolyte solution on both sides of a solid-state matrix comprising a solid-state pore opening, the electrolyte solution comprising a hydrophilic protein; and as a result of the applying of the at least one of the voltage and the pressure, forming a stable insertion fit of a hydrophilic protein channel comprising the hydrophilic protein within the solid-state pore opening, the hydrophilic protein channel comprising a protein nanopore channel.

In further, related embodiments, the hydrophilic protein of the hydrophilic protein channel may comprise a modification of an amino acid sequence comprising SEQ ID NO: 1, the modification comprising one or more of: (i) a modification of an upper internal surface residue or a lower internal surface residue of the protein of the hydrophilic protein channel, the modification comprising an alteration of an electrostatic surface potential of an upper internal surface or a lower internal surface of SEQ ID NO: 1; (ii) a modification comprising an insertion of a cysteine residue into SEQ ID NO: 1 or a replacement of an amino acid residue of SEQ ID NO: 1 with a cysteine residue; (iii) a modification of a tunnel loop residue of the protein of the hydrophilic protein channel, the modification comprising an expansion of a narrowest constriction of a tunnel loop of SEQ ID NO: 1, a restriction of the narrowest constriction of the tunnel loop of SEQ ID NO: 1, or a removal of the narrowest constriction of the tunnel loop of SEQ ID NO: 1; (iv) a modification of a tunnel loop residue of the protein of the hydrophilic protein channel, the modification resulting in an alteration of an electrostatic charge property of a tunnel loop of SEQ ID NO: 1; (v) a modification which alters an external charge of the protein of the hydrophilic protein channel; (vi) a modification which promotes binding of the protein of the hydrophilic protein channel to the solid-state matrix; (vii) a modification which extends an N-terminus or a C-terminus of SEQ ID NO: 1 or an N-terminus or a C-terminus of a cleaved portion of SEQ ID NO: 1; and (viii) a deletion of an amino acid residue of at least one of a C-terminal region and an N-terminal region of SEQ ID NO: 1. The modification of SEQ ID NO: 1 may comprise a modification of the lower internal surface residue of the protein of the hydrophilic protein channel, the modification comprising the alteration of the electrostatic surface potential of the lower internal surface of SEQ ID NO: 1, and the protein of the hydrophilic protein channel may comprise SEQ ID NO: 27. The modification of SEQ ID NO: 1 may comprise a replacement of an amino acid residue of SEQ ID NO: 1 with a cysteine residue, and the protein of the hydrophilic protein channel may comprise SEQ ID NO: 11 or SEQ ID NO: 37. The modification of SEQ ID NO: 1 may comprise a modification of the tunnel loop residue of the protein of the hydrophilic protein channel, the modification comprising the expansion of the narrowest constriction of the tunnel loop of SEQ ID NO: 1, the restriction of the narrowest constriction of the tunnel loop of SEQ ID NO: 1, or the removal of the narrowest constriction of the tunnel loop of SEQ ID NO: 1, and the protein of the hydrophilic protein channel may comprise one of: SEQ ID NO: 15, SEQ ID NO: 17, SEQ ID NO: 21, SEQ ID NO: 23, and SEQ ID NO: 25. The modification of SEQ ID NO: 1 may comprise the modification in a tunnel loop residue of the protein of the hydrophilic protein channel, the modification resulting in the alteration of the electrostatic charge property of the tunnel loop of SEQ ID NO: 1, and the protein of the hydrophilic protein channel may comprise SEQ ID NO: 19. The modification of SEQ ID NO: 1 may comprise the modification which alters the external charge of the hydrophilic protein channel, and the protein of the hydrophilic protein channel may comprise one of: SEQ ID NO: 9 and SEQ ID NO: 13. The modification of SEQ ID NO: 1 may comprise the modification which promotes binding of the protein of the hydrophilic protein channel to the solid-state matrix, and the protein of the hydrophilic protein channel may comprise one of: SEQ ID NO: 29, SEQ ID NO: 31 and SEQ ID NO: 35. The modification of SEQ ID NO: 1 may comprise the modification which extends the N-terminus of the cleaved portion of SEQ ID NO: 1, and the protein of the hydrophilic protein channel may comprise SEQ ID NO: 33. The modification of SEQ ID NO: 1 may comprise the deletion of an amino acid residue of at least one of the C-terminal region and the N-terminal region of SEQ ID NO: 1, and the modification may comprise a modification of one of: SEQ ID NO: 3, SEQ ID NO: 5 and SEQ ID NO: 7. The protein of the hydrophilic protein channel may comprise a modification of SEQ ID NO: 1, the modification comprising a modification in one or more of: a wing loop residue, a tunnel loop residue, an upper internal surface residue, a lower internal surface residue, an external surface residue, a C-terminal residue, and an N-terminal residue. The protein of the hydrophilic protein channel may comprise a modification of SEQ ID NO: 1, the modification comprising one or more of: a modification of residue 328 of SEQ ID NO: 1, a modification of residue 189 of SEQ ID NO: 1, and a modification of residue 367 of SEQ ID NO: 1. A protein forming at least part of the hydrophilic protein channel may comprise a modification of SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7. A protein forming at least part of the hydrophilic protein channel may comprise a modification of SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In other related embodiments, the solid-state matrix may comprise at least one of: silicon, hafnium and nickel. The solid-state matrix may comprise at least one of: a silicon containing nitride, a silicon containing carbide and a silicon containing oxide. The solid-state matrix may comprise a thickness of less than about 30 nm. The solid-state pore opening may comprise a diameter of between about 5.4 nm and about 6 nm. The method may further comprise coating the solid-state matrix to promote binding of the solid-state matrix to a protein forming at least part of the hydrophilic protein channel. Coating the solid-state matrix may comprise applying a thiol-coupling compound to the solid-state matrix. Coating the solid-state matrix may comprise applying a coating comprising a maleimide compound to the solid-state matrix.

In another embodiment according to the invention, there is provided a protein variant encoded by a modification of a nucleic acid sequence of SEQ ID NO: 2, the modification comprising one or more of: (i) a modification in a portion of the nucleic acid sequence that encodes an upper internal surface residue or a lower internal surface residue of the protein variant encoded by the nucleic acid sequence, the modification producing an alteration of an electrostatic surface potential of an upper internal surface or a lower internal surface of the protein variant encoded by the nucleic acid sequence; (ii) a modification comprising an insertion of a cysteine residue into the protein variant encoded by the nucleic acid sequence or a replacement of an amino acid residue of the protein variant encoded by the nucleic acid sequence with a cysteine residue; (iii) a modification to produce a modification of a tunnel loop residue of the protein variant encoded by the nucleic acid sequence, the modification in the tunnel loop residue comprising an expansion of a narrowest constriction of a tunnel loop of the protein variant encoded by the nucleic acid sequence, a restriction of the narrowest constriction of the tunnel loop of the protein variant encoded by the nucleic acid sequence, or a removal of the narrowest constriction of the tunnel loop of the protein variant encoded by the nucleic acid sequence; (iv) a modification to produce a modification of a tunnel loop residue of the protein variant encoded by the nucleic acid sequence, the modification resulting in an alteration of an electrostatic charge property of a tunnel loop of the protein variant encoded by the nucleic acid sequence; (v) a modification which alters an external charge of the protein variant encoded by the nucleic acid sequence; (vi) a modification which promotes binding of the protein variant encoded by the nucleic acid sequence to a solid-state matrix; (vii) a modification which extends an N-terminus or a C-terminus of the protein variant encoded by the nucleic acid sequence or an N-terminus or a C-terminus of a cleaved portion of the protein variant encoded by the nucleic acid sequence; and (viii) a deletion of an amino acid residue of at least one of a C-terminal region and an N-terminal region of the protein variant encoded by the nucleic acid sequence.

In further, related embodiments, the modification of SEQ ID NO: 2 may comprise a modification in a portion of the nucleic acid sequence that encodes the lower internal surface residue of the protein variant encoded by the nucleic acid sequence, the modification producing the alteration of the electrostatic surface potential of the lower internal surface of the protein variant encoded by the nucleic acid sequence, and the modification of the nucleic acid sequence may comprise SEQ ID NO: 28. The modification of SEQ ID NO: 2 may comprise a replacement of an amino acid residue of the protein variant encoded by the nucleic acid sequence with the cysteine residue, and the modification of the nucleic acid sequence may comprise SEQ ID NO: 12 or SEQ ID NO: 38. The modification of SEQ ID NO: 2 may comprise the modification to produce a modification of a tunnel loop residue of the protein variant encoded by the nucleic acid sequence, the modification in the tunnel loop residue comprising the expansion of the narrowest constriction of the tunnel loop of the protein variant encoded by the nucleic acid sequence, the restriction of the narrowest constriction of the tunnel loop of the protein variant encoded by the nucleic acid sequence, or the removal of the narrowest constriction of the tunnel loop of the protein variant encoded by the nucleic acid sequence, and the modification of the nucleic acid sequence may comprise one of: SEQ ID NO: 16, SEQ ID NO: 18, SEQ ID NO: 22, SEQ ID NO: 24, and SEQ ID NO: 26. The modification of SEQ ID NO: 2 may comprise the modification to produce a modification of a tunnel loop residue of the protein variant encoded by the nucleic acid sequence, the modification resulting in an alteration of an electrostatic charge property of a tunnel loop of the protein variant encoded by the nucleic acid sequence, and the modification of the nucleic acid sequence may comprise SEQ ID NO: 20. The modification of SEQ ID NO: 2 may comprise the modification which alters the external charge of the protein variant encoded by the nucleic acid sequence, and the modification of the nucleic acid sequence may comprise one of: SEQ ID NO: 10 and SEQ ID NO: 14. The modification of SEQ ID NO: 2 may comprise the modification which promotes binding of the protein variant encoded by the nucleic acid sequence to the solid-state matrix, and the modification of the nucleic acid sequence may comprise one of: SEQ ID NO: 30, SEQ ID NO: 32 and SEQ ID NO: 36. The modification of SEQ ID NO: 2 may comprise the modification which extends the N-terminus of the cleaved portion of the protein variant encoded by the nucleic acid sequence, and the modification of the nucleic acid sequence may comprise SEQ ID NO: 34. The modification of SEQ ID NO: 2 may comprise a deletion of an amino acid residue of at least one of a C-terminal region and an N-terminal region of the protein variant encoded by the nucleic acid sequence, and the modification of the nucleic acid sequence may comprise one of: SEQ ID NO: 4, SEQ ID NO: 6 and SEQ ID NO: 8. The modification of SEQ ID NO: 2 may comprise a modification to produce a modification in one or more of: a wing loop residue, a tunnel loop residue, an upper internal surface residue, a lower internal surface residue, an external surface residue, a C-terminal residue, and an N-terminal residue; of the protein variant encoded by the modification of the nucleic acid sequence.

In another embodiment according to the invention, there is provided a protein variant encoded by a modification of a nucleic acid sequence of SEQ ID NO: 2, the modification comprising one or more of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment according to the invention, there is provided a protein variant encoded by a modification of a nucleic acid sequence of SEQ ID NO: 2, the modification comprising one or more of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment according to the invention, there is provided a vector comprising a modification of a nucleic acid sequence of SEQ ID NO: 2, the modification comprising one or more of: (i) a modification in a portion of the nucleic acid sequence that encodes an upper internal surface residue or a lower internal surface residue of a protein encoded by the nucleic acid sequence, the modification producing an alteration of an electrostatic surface potential of an upper internal surface or a lower internal surface of the protein encoded by the nucleic acid sequence; (ii) a modification comprising an insertion of a cysteine residue into a protein encoded by the nucleic acid sequence or a replacement of an amino acid residue of a protein encoded by the nucleic acid sequence with a cysteine residue; (iii) a modification to produce a modification of a tunnel loop residue of a protein encoded by the nucleic acid sequence, the modification of the tunnel loop residue comprising an expansion of a narrowest constriction of a tunnel loop of the protein encoded by the nucleic acid sequence, a restriction of the narrowest constriction of the tunnel loop of the protein encoded by the nucleic acid sequence, or a removal of the narrowest constriction of the tunnel loop of the protein encoded by the nucleic acid sequence; (iv) a modification to produce a modification of a tunnel loop residue of a protein encoded by the nucleic acid sequence, the modification resulting in an alteration of an electrostatic charge property of a tunnel loop of the protein encoded by the nucleic acid sequence; (v) a modification which alters an external charge of a protein encoded by the nucleic acid sequence; (vi) a modification which promotes binding of a protein encoded by the nucleic acid sequence to a solid-state matrix; (vii) a modification which extends an N-terminus or a C-terminus of a protein encoded by the nucleic acid sequence or an N-terminus or a C-terminus of a cleaved portion of the protein encoded by the nucleic acid sequence; and (viii) a deletion of an amino acid residue of at least one of a C-terminal region and an N-terminal region of a protein encoded by the nucleic acid sequence.

In further related embodiments, the modification of SEQ ID NO: 2 may comprise a modification in the portion of the nucleic acid sequence that encodes the lower internal surface residue of the protein encoded by the nucleic acid sequence, the modification producing the alteration of the electrostatic surface potential of the lower internal surface of the protein encoded by the nucleic acid sequence, and the modification of the nucleic acid sequence may comprise SEQ ID NO: 28. The modification of SEQ ID NO: 2 may comprise a modification comprising an insertion of a cysteine residue into the protein encoded by the nucleic acid sequence or a replacement of an amino acid residue of a protein encoded by the nucleic acid sequence with the cysteine residue, and the modification of the nucleic acid sequence may comprise one of: SEQ ID NO: 12 and SEQ ID NO: 38. The modification of SEQ ID NO: 2 may comprise a modification to produce a modification of a tunnel loop residue of the protein encoded by the nucleic acid sequence, the modification in the tunnel loop residue comprising the expansion of the narrowest constriction of the tunnel loop of the protein encoded by the nucleic acid sequence, the restriction of the narrowest constriction of the tunnel loop of the protein encoded by the nucleic acid sequence, or the removal of the narrowest constriction of the tunnel loop of the protein encoded by the nucleic acid sequence, and the modification of the nucleic acid sequence may comprise one of: SEQ ID NO: 16, SEQ ID NO: 18, SEQ ID NO: 22, SEQ ID NO: 24, and SEQ ID NO: 26. The modification of SEQ ID NO: 2 may comprise a modification to produce a modification of the tunnel loop residue of the protein encoded by the nucleic acid sequence, the modification resulting in the alteration of the electrostatic charge property of the tunnel loop of the protein encoded by the nucleic acid sequence, and the modification of the nucleic acid sequence may comprise SEQ ID NO: 20. The modification of SEQ ID NO: 2 may comprise the modification which alters the external charge of the protein encoded by the nucleic acid sequence, and the modification of the nucleic acid sequence may comprise one of: SEQ ID NO: 10 and SEQ ID NO: 14. The modification of SEQ ID NO: 2 may comprise the modification which promotes binding of the protein encoded by the nucleic acid sequence to the solid-state matrix, and the modification of the nucleic acid sequence may comprise one of: SEQ ID NO: 30, SEQ ID NO: 32 and SEQ ID NO: 36. The modification of SEQ ID NO: 2 may comprise the modification which extends the N-terminus of the cleaved portion of the protein encoded by the nucleic acid sequence, and the modification of the nucleic acid sequence may comprise SEQ ID NO: 34. The modification of SEQ ID NO: 2 may comprise the deletion of the amino acid residue of at least one of the C-terminal region and the N-terminal region of the protein encoded by the nucleic acid sequence, and the modification of the nucleic acid sequence may comprise one of: SEQ ID NO: 4, SEQ ID NO: 6 and SEQ ID NO: 8. The modification of SEQ ID NO: 2 may comprise a modification to produce a modification in one or more of: a wing loop residue, a tunnel loop residue, an upper internal surface residue, a lower internal surface residue, an external surface residue, a C-terminal residue, and an N-terminal residue; of a protein encoded by the modification of the nucleic acid sequence.

In another embodiment according to the invention, there is provided a vector comprising a modification of a nucleic acid sequence of SEQ ID NO: 2, the modification comprising one or more of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment according to the invention, there is provided a vector comprising a modification of a nucleic acid sequence of SEQ ID NO: 2, the modification comprising one or more of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In other embodiments, there is provided a cell comprising any of the vectors taught herein.

In another embodiment according to the invention, there is provided a nucleic acid sequence encoding any of the protein variants taught herein.

In further, related embodiments, the cell may be any of the vectors taught in the foregoing paragraphs.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 2 shows a slice through the middle of molecular surface colored according to charge from red (−1 kT/e) to blue (+1 kT/e).

FIG. 6 is a graph of a typical current profile over time recorded through a 5.5 nm SS pore at +100 mV. After injection of 0.1 nmol of portal protein, short current drops are detected, interpreted as portal collisions with the solid-state nanopore. FIG. 7 is a graph of a representative current vs time trace recorded for a 5.4 nm SS nanopore at +80 mV, showing stable insertion of a portal protein. FIG. 8 is a graph of current as a function of the applied voltage for a 5.5 nm SS pore recorded before (red/cross markers, with a higher slope) and after insertion of a portal protein (purple/triangle, with a lower slope). FIG.

9 is a graph of current noise analysis of a 5.5 nm diameter solid-state nanopore before (red, top curve) and after insertion of a portal protein (purple, bottom curve). FIG. 10 is a graph of conductance of solid-state nanopore vs conductance of portal hybrid pore (n=32 for CD/N hybrids and n=15 for CGG hybrids). Experiments were performed in 0.5 M NaCl, 20 mM Tris pH 7.5.

FIGS. 11A-11C are graphs showing dynamics of TPX2 peptide transport, in experiments in accordance with an embodiment of the invention. FIG. 11A is a graph showing a current vs time trace recorded through a hybrid pore at +30, +40 and +55 mV in the presence of 10.3 μM TPX2 peptide. FIG. 11B is a semi-log plot of the event frequency as a function of the applied voltage. The line is an exponential fit to the equation. FIG. 11C is a semi-log plot of the peptide dwell time as a function of the applied voltage. The lines in FIGS. 11B and 11C are exponential fits. Experiments were performed in 0.5 M NaCl, 20 mM Tris pH 7.5.

FIGS. 12A-12E are graphs illustrating sensing of different biopolymers using a hybrid nanopore, in experiments in accordance with an embodiment of the invention. Current vs time trace recorded through the hybrid pore at +60 mV in the presence of (FIG. 12A) 36.0 μM insulin, (FIG. 12B) 7.7 μM DNA hairpin, (FIG. 12C) 10.3 μM TPX2 peptide and (FIG. 12D) 16.6 μM ssDNA. The data in (FIG. 12A) were filtered at 10 kHz (grey) or 0.5 kHz (green). FIG. 12E is a scatter plot of ΔI vs dwell time for the DNA hairpin (red), the peptide (purple) and the ssDNA (orange). Experiments were performed in 0.5 M NaCl, 20 mM Tris pH 7.5.

DETAILED DESCRIPTION

Figure 1:
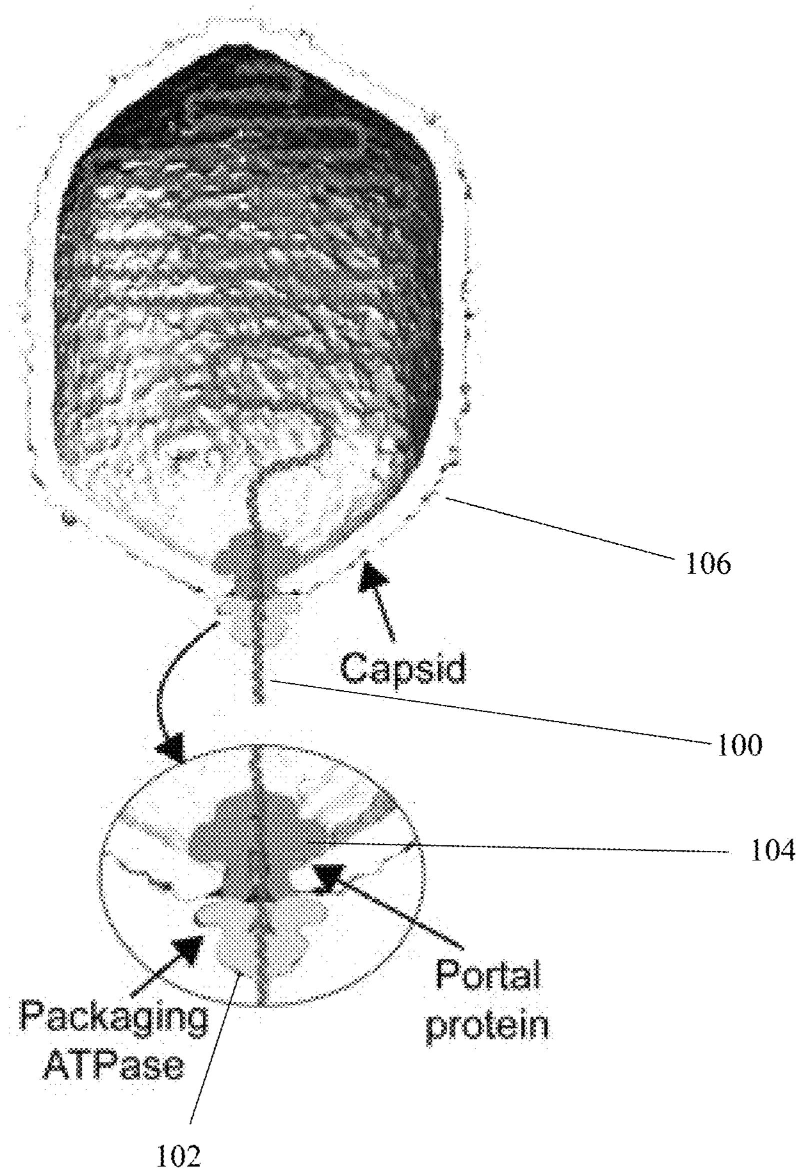
FIG. 1 is a schematic diagram of the DNA packaging machine of a dsDNA virus.

A description of example embodiments follows.

Hybrid nanopores in accordance with an embodiment of the invention, comprising a protein pore supported within a solid-state membrane, combine the robust nature of solid-state membranes with the easily tunable and precise engineering of protein nanopores. A lipid-free hybrid nanopore comprises a water soluble and stable, modified portal protein of the *Thermus thermophilus* bacteriophage G20c, electrokinetically inserted into a larger nanopore in a solid-state membrane. The hybrid pore is stable and easy to fabricate, and exhibits low peripheral leakage, allowing sensing and discrimination among different types of biomolecules.

The protein channel in accordance with embodiments of the invention can either voltage- or pressure-insert into the solid-state nanopore matrix to form the hybrid nanopore sensor device. The signal for sensing using this device can be either electrical or optical, the latter offering high-density parallelized readout from multiple adjacent pores. Embodiments include mechanisms to obtain the hybrid structure, to stabilize it, and to modify it so that different types of biomolecules can be sensed.

In embodiments, the hybrid sensor does not require any lipid support, which is typically fragile and not durable; it allows atomic-precision engineering to chemically define the pore sensor properties; and chemical methods of stabilizing the portal-to-solid-state interface are controlled by biomolecular engineering and materials science approaches. The hybrid sensor can, for example, provide the advantages of: rapid and stable insertion of a protein into a solid-state nanopore; mutations of the protein can be used for sensing improvement; and translocation of biopolymers (such as nucleic acids and polypeptides) through the hybrid sensor can be performed for sensing applications. Example potential merits of such a device are in applications that include: 1) high-resolution mapping of DNA, RNA sequencing, DNA sequencing; 2) protein identification, protein conformational change monitoring; 3) polypeptide sequencing; 4) small-molecule detection, biomolecular complex detection, and enzyme-ligand binding. The broad range of uses could potentially impact many areas of the human health, biotechnology and agri-food sectors.

The advent of single-molecule detection is having an unparalleled impact on the speed with which structural and dynamic aspects of molecules can be probed (1). In this regard, nanopores have shown much promise as electrical (2-7) and electro-optical sensors (8-10) and several nanopore-based systems are now being adopted as primary tools for DNA (11-13) and RNA (14) sequencing.

Despite recent progress, identification and quantification of molecular species in solution (15-28) requires a reproducible nanopore platform that affords physical stability, structural precision, and often, a spatially-defined pore position (for example, in electro-optical sensing). While synthetic nanopores fabricated in solid-state (SS) membranes offer physical robustness (29-31), pore-to-pore variability often limits the reproducibility of experiments, necessitating additional control checks and validation. On the contrary, protein channels embedded in organic thin membranes (e.g., a lipid-bilayer) offer the highest reproducibility due to the precise folding and repetitive nature of the constituting multi-subunit protein oligomers (32,33), but their supporting membrane is typically less chemically and physically robust, and further, the pore position is not well-defined due to in-plane diffusion of the protein channel (34). Hybrid nanopore devices, in which channel-containing proteins are embedded in larger pores made in a SS matrix, have been proposed as a strategic solution for combining the benefits—while overcoming the limitations—of existing nanopores (35). Although initial experiments based on inserting pore-containing proteins with lipophilic regions into a SS pore looked promising (35), challenges in inserting such proteins into a SS pore and in controlling the protein orientation have remained major obstacles in the applicability of hybrid nanopores to nanotechnology.

An embodiment according to the present invention provides a hybrid nanopore based on the hydrophilic portal protein derived from a thermostable virus, the *Thermus thermophilus* bacteriophage G20c (36). In double-stranded DNA viruses, the portal protein is incorporated into the capsid shell (see, e.g., FIG. 1), thereby serving as a natural pore through which DNA is moved in and out (37). FIG. 1 is a schematic diagram of the DNA packaging machine of a dsDNA virus. Viral genomic DNA 100 is translocated into the preformed virus capsid by the packaging ATPase 102 through the portal protein 104 embedded in the viral capsid 106. The protein contains a tight tunnel constriction with a repetitive chemical character, being made up by a circle of identical "tunnel loops", contributed by 12 subunits (38).

Figure 2:
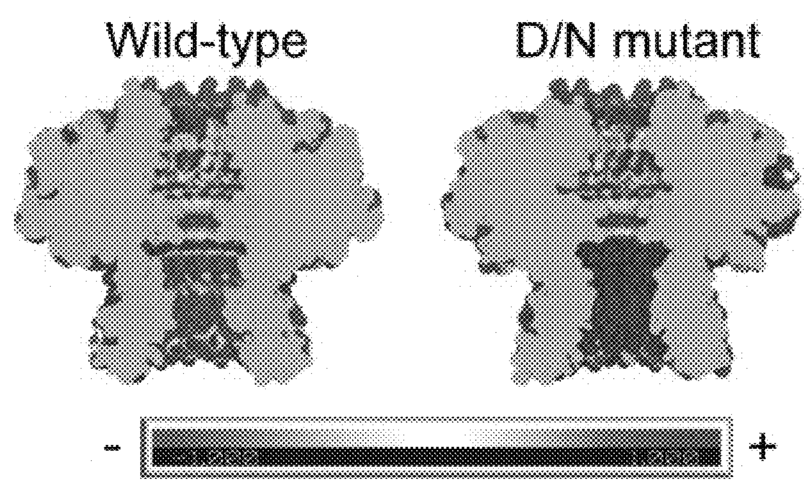
FIG. 2 is a schematic diagram showing electrostatic properties of the tunnel in wild-type (left) and mutant (right) portal proteins, where the mutant portal protein is the CD/N mutant of the G20c bacteriophage in accordance with an embodiment of the invention.

In an embodiment according to the invention, this protein is engineered to reprogram its physico-chemical and electrostatic properties. For example, in one protein version, CGG, (33) a portal with a larger minimum aperture of ~2.3 nm is defined by two residues in the tunnel loops substituted to glycines; and in another protein version, CD/N, the internal surface charges are electrostatically engineered by replacing aspartic acid (D) residues with asparagines (N). The latter CD/N mutation had a major impact on the charge of the internal tunnel's surface, (see FIG. 2) and permitted electrical sensing of biomolecules. FIG. 2 is a schematic diagram showing electrostatic properties of the tunnel in wild-type (left) and mutant (right) portal proteins, where the mutant portal protein is the CD/N mutant of the G20c bacteriophage in accordance with an embodiment of the invention. FIG. 2 shows a slice through the middle of molecular surface colored according to charge from red (−1 kT/e) to blue (+1 kT/e). In another example of this portal system, a cysteine substitution is made in an externally facing residue 49 (designated "C") which allows chemical labeling and surface immobilization of the portal protein. (33)

Figure 3:
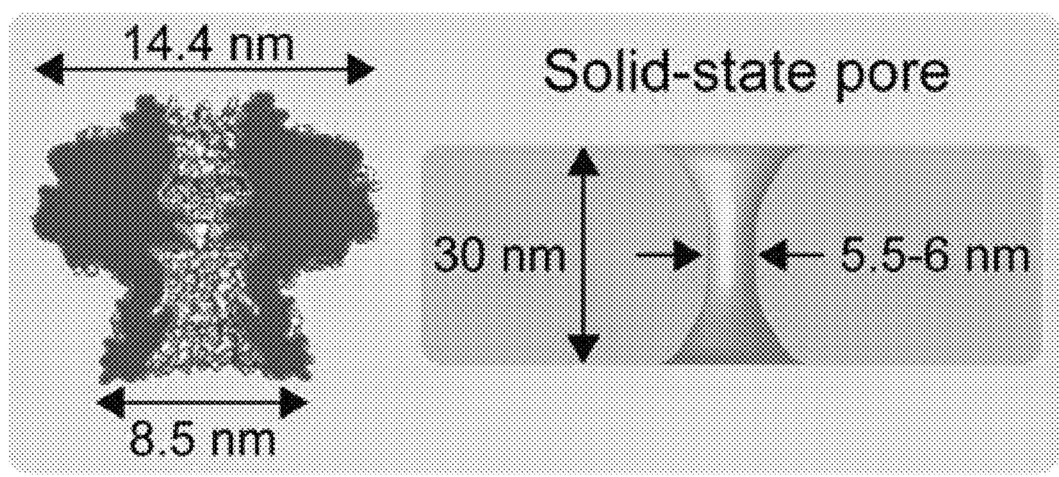
FIG. 3 is a schematic diagram showing dimensions of the portal protein (left) and the SS nanopore (right), in accordance with an embodiment of the invention.
Figure 4:
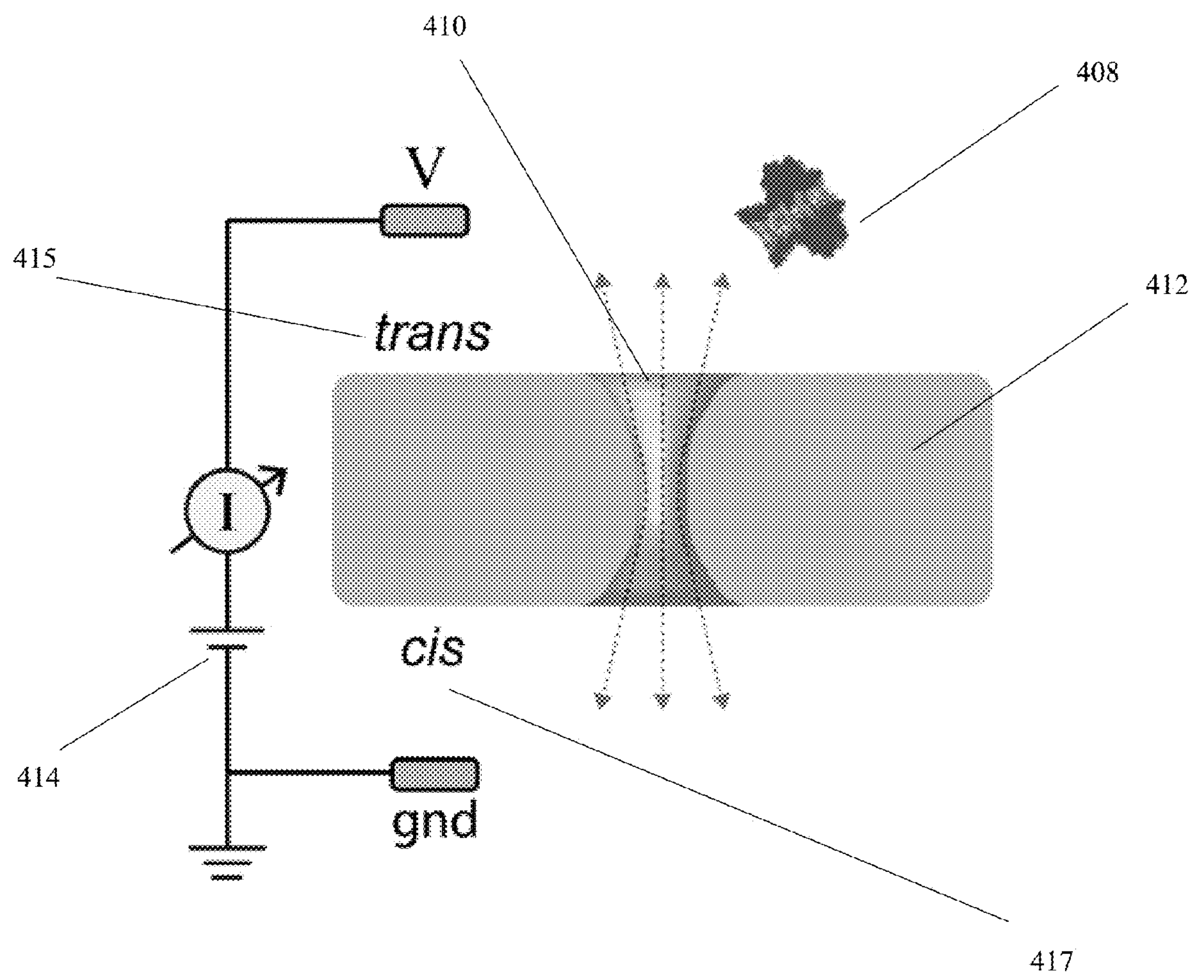
FIG. 4 is a schematic diagram illustrating insertion of a purified portal protein into a nanopore in a thin solid-state membrane, in accordance with an embodiment of the invention.
Figure 5:
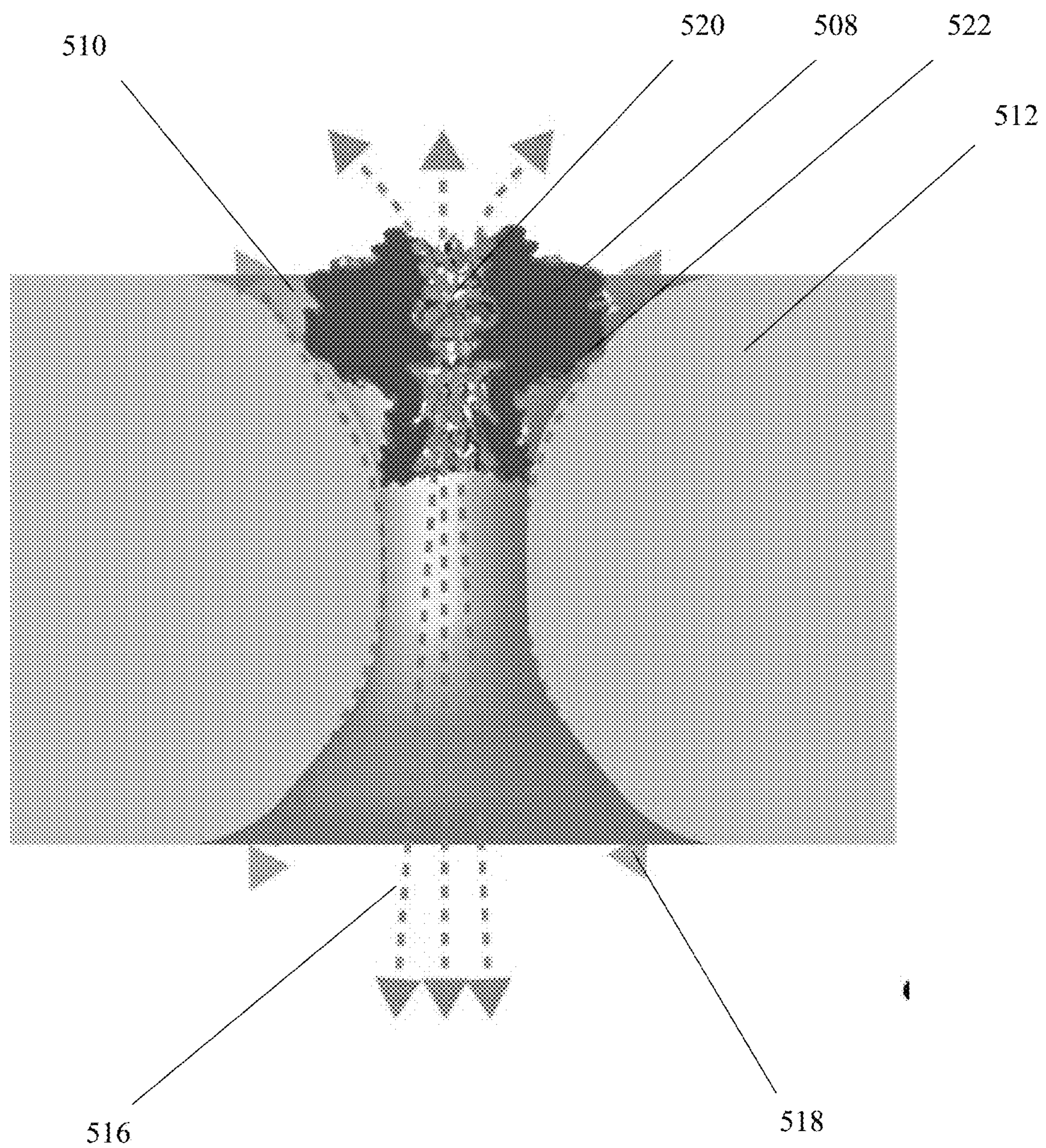
FIG. 5 is a schematic diagram of the hybrid nanopore, in accordance with an embodiment of the invention, in which application of voltage results in ion current through the pore, as well as leakage current that is peripheral to the pore.

An embodiment uses this structurally programmable portal protein as a nanoscale adapter by electrokinetically embedding it snugly inside a larger pore made in a free-standing silicon nitride (SiN), or other solid-state, membrane (see FIGS. 4 and 5). Electrokinetic "corking" occurs when the force on the protein, induced by applied voltage, is sufficient to "squeeze" the portal into the SS pore. It is found that, for stable insertion, a diameter of the solid-state nanopore of from 5.4 to 6 nm and a nominal membrane thickness of 30 nm, work well. Given the dimensions of the portal assembly (33) (see FIG. 3), the geometric constraints set by the SS pore restrict the range of possible orientations of the portal pore in it, such that the stem is inserted within the SS nanopore constriction, and the wider "cap" self-orients towards the top of the trans chamber (see FIG. 5). FIG. 3 is a schematic diagram showing dimensions of the portal protein (left) and the SS nanopore (right), in accordance with an embodiment of the invention. The portal protein is, for example, about 14.5 nm wide at its top, "cap" end, and about 8.5 nm wide at its narrower base end. The solid-state nanopore is, for example, between about 5.5 and about 6 nm wide, and about 30 nm in thickness (across the membrane). The larger size of the "cap", as compared with the SS pore diameter, prevents the entire protein from moving through the SS nanopore. Remarkably, interactions between the portal protein squeezed into the SS pore and the SS-pore surface contribute to a stable, self-inserting and self-aligning hybrid (see FIG. 5) that exhibits tolerable peripheral ion leakage, probed using cyclodextrin as a pore current modulator. FIG. 4 is a schematic diagram illustrating insertion of the purified portal protein, which assembles its dodecameric units to form a hydrophilic protein channel 408, into a nanopore solid-state pore opening 410 drilled into a thin solid-state (SS) matrix membrane 412, in accordance with an embodiment of the invention. Portal protein is applied to the trans chamber 415 of a SS nanopore device containing an electrolyte solution of 20 mM Tris pH 7.5, 0.5 M NaCl. The protein electrokinetically inserts into the SS pore during application of a positive voltage by voltage source 414. FIG. 5 is a schematic diagram of the hybrid nanopore, in accordance with an embodiment of the invention, in which application of voltage results in ion current 516 through the pore, as well as leakage current 518 that is peripheral to the pore. The hybrid nanopore sensor includes, with reference to both FIGS. 4 and 5, the voltage source 414, the electrolyte (not shown) in both the trans chamber 415 and cis chamber 417 (see FIG. 4) on both sides of the solid-state matrix 412. With reference to FIG. 5, the hybrid nanopore sensor includes: the hydrophilic protein channel 508, formed from the assembled dodecameric units of hydrophilic portal protein monomers; the solid-state matrix 512 with the solid-state pore opening 510 formed therein, where the solid-state pore opening 510 is a nanopore; and the protein nanopore channel 520 through the middle of the hydrophilic protein channel 508. The hydrophilic protein channel 508 forms a stable insertion fit 522 within the solid-state pore opening 510.

Figure 13:
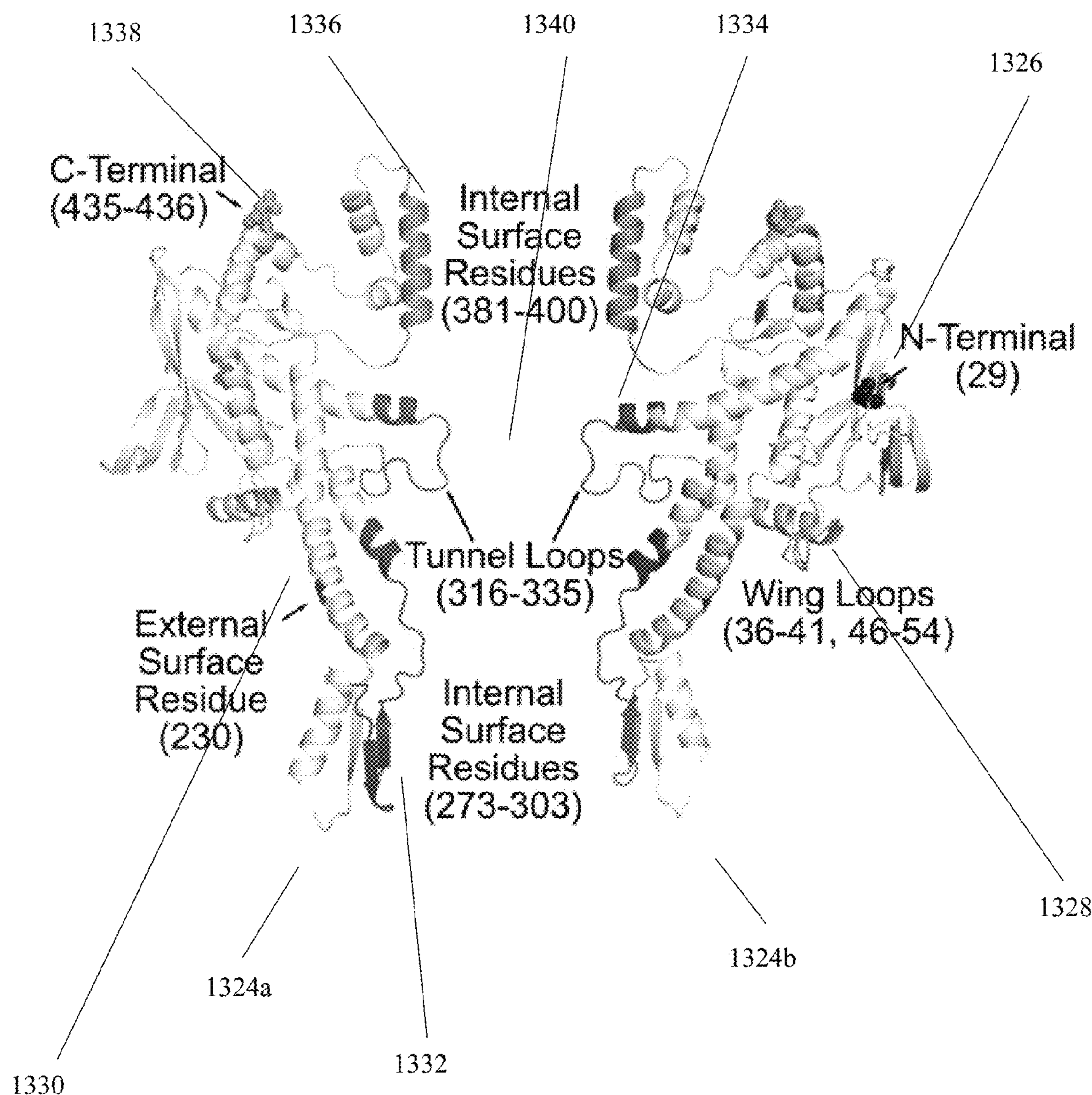
FIG. 13 is a schematic diagram showing component amino acid residue regions of the portal protein of the *Thermus thermophilus* bacteriophage G20c, which can be modified, in embodiments according to the invention, to promote assembly and operation of, and sensing with, the hybrid sensor.

FIG. 13 is a schematic diagram showing component amino acid residue regions of the portal protein of the *Thermus thermophilus* bacteriophage G20c, which can be modified, in embodiments according to the invention, to promote assembly and operation of, and sensing with, the hybrid sensor. In FIG. 13, two monomers 1324a and 1324b are shown (left and right are reflected version of each other), but it will be appreciated that twelve such monomers assemble to form the full dodecameric assembly that can create a protein channel in accordance with an embodiment of the invention. As shown in FIG. 13, the regions include: the N-terminal region 1326, which includes amino acid residue 29; the wing loop region 1328, which includes amino acid residues 36-41 and 46-54; the external surface residues 1330, which include amino acid residue 230; the internal surface residues 1332 of the lower tunnel region, which include amino acid residues 273-303; the tunnel loop region 1334, which includes amino acid residues 316-335, and forms a narrowest constriction 1340 where the tunnel loops are closest to each other; the internal surface residue 1336 of the upper tunnel region, which include amino acid residues 381-400; and the C-terminal region 1338, which includes amino acid residues 435-436.

Figure 14:
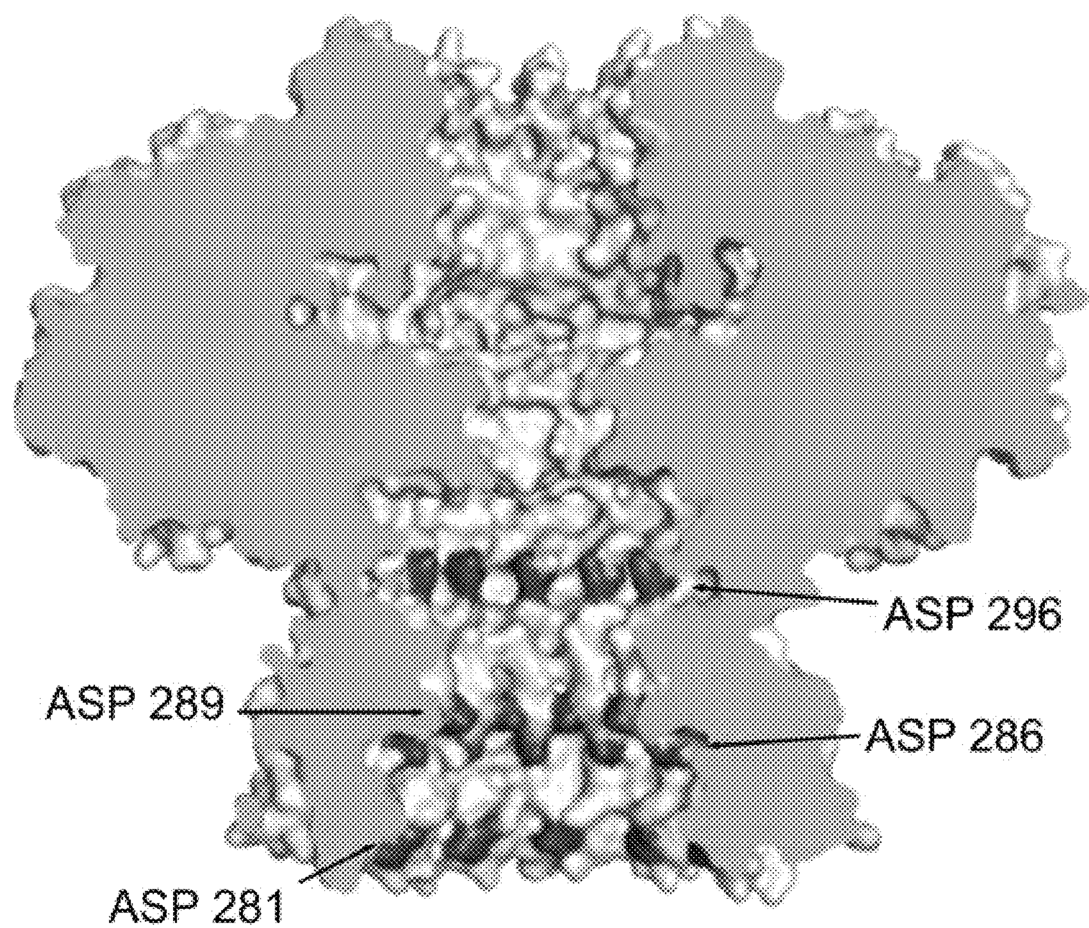
FIG. 14 is a schematic diagram showing an example of residues that can be mutated in one example, mutant, the CD/N mutant, in accordance with an embodiment of the invention.

FIG. 14 is a schematic diagram showing an example of residues that can be mutated in one example mutant, the CD/N mutant, in accordance with an embodiment of the invention. Here, residues ASP 281, ASP 286, ASP 289 and ASP 296 are mutated from aspartic acid (D) to asparagine (N).

The G20c portal protein is a stable circular dodecameric assembly of 12 monomers with a central tunnel of defined geometry and physicochemical properties. In accordance with some embodiments, a base scaffold of the protein is used that is trimmed to the core structure comprising residues 25-438 of the portal protein's amino acid sequence, where the unstructured N- and C-terminal regions (residues 1-24 and 439-448 of the wild type residues 1-448 of the protein) have been removed to improve stability. A major advantage of this scaffold is the absence of cysteine residues, which allows flexible design of cysteine-containing mutants that can be chemically derivatized for different applications, such as attachment to surfaces or insertion into membranes.

In accordance with embodiments of the invention, the properties of the portal protein can be engineered for specific sensing and device integration applications by mutating the surface residues lining the tunnel, those on the outer surface of the portal protein assembly and residues that stabilize or otherwise alter either intramonomer or intermonomer contacts. Mutations can, for example, include, but are not limited to, the segments containing internal tunnel lining residues 273-303 of the lower tunnel region and 381-400 of the upper tunnel region; tunnel loop residues 316-335; and surface residues such as the wing loops 36-41 and 46-54 that are part of a range of residues 36-54.

Further modifications to the protein can, for example, include fusion of peptide sequences, protein domains or proteins to the N or C-terminus of the protein or into external loops that will confer properties for attachment or sensing of ligand binding events to different biomolecules, bacteria, cells viruses and/or chemical assemblies.

In some embodiments, portal protein variants comprise specifically placed cysteine residues for chemical attachment to surfaces, insertion into lipid bilayers and/or linking to additional sensor components, such as ligand binding aptamers. These include the 49C or C mutant where a cysteine has been introduced into one of the wing loops at position 49; and the D400C variant where a cysteine has been placed at the top of the upper tunnel helix. Mutant proteins are referred to herein by the "Protein Version" names given in Tables 1-7, below. The 49C version has the amino acid sequence given in SEQ ID NO: 11 and the DNA sequence given in SEQ ID NO: 12. The D400C version has the amino acid sequence given in SEQ ID NO: 37 and the DNA sequence given in SEQ ID NO: 38. The 49C version can be used, either alone or in combination with other mutations, such as CGG or CD/N. D400C has been found to form dodecamer sized assemblies when purified.

In other embodiments, the tunnel properties of the portal assembly can be engineered, for example by expanding the narrowest constriction of the tunnel loops of residues 316-335 (see FIG. 13) and by altering the electrostatic surface potential of the tunnel, as in CD/N. Additional examples of other variants in the tunnel loop geometry that assemble into the characteristic circular protein complexes include: V325M designed to further restrict the narrowest aperture of the tunnel; and the Loop2GG and CLoop3G mutants that entirely remove the central constriction in the tunnel. Further charge alterations to the tunnel include the placement of a flexible positive lysine residue at the narrowest point of the tunnel loops (I328K) and proposed additional substitution of aspartic acid residues 383 and 400 in the upper tunnel helix (residues 381-400) with asparagine residues to reduce the negative charge in the upper tunnel surface.

In further embodiments, the external surface charge properties of the protein can be altered by introducing charged amino acids in place of uncharged surface residues, such as with the V40E and L230E, which are, respectively, in the wing loop region (for V40E) and the external surface residue region (for L230E). Similar alterations in the external surface residues can be made to create a more hydrophobic external surface. Peptide sequences have been successfully introduced into the wing loop 46-54 to promote binding to silicon surfaces (in the SIN1, SIN 2 and SIN 4 mutations). SIN1 and SIN2 form circular assemblies.

In other embodiments, extensions to the N- and C-terminal can be used to introduce longer peptide sequences for targeted surface (metal or lipid) interaction or to introduce ligand binding domains for specific sensing applications. Such extensions include the hexahistidine affinity tag used for nickel binding and purification. Additional N-terminal extensions include the SIN3 silicon binding sequence.

In one embodiment, the wild type full length portal protein of G20c bacteriophage, comprising SEQ ID NO: 1, can be modified in the lower internal surface residue of the hydrophilic protein channel, to alter the electrostatic surface potential of the lower internal surface of SEQ ID NO: 1. For example, for such a purpose, the hydrophilic protein channel can comprise the CD/N variant with amino acid SEQ ID NO: 27, which has a corresponding modified DNA sequence of SEQ ID NO: 28.

In another embodiment, the wild type portal protein, comprising SEQ ID NO: 1 can be modified to replace the residue of SEQ ID NO: 1 with a cysteine residue. For example, for such a purpose, the hydrophilic protein channel can comprise the 49C variant with amino acid SEQ ID NO: 11, which has a corresponding modified DNA sequence of SEQ ID NO: 12, or can comprise the D400C variant with amino acid SEQ ID NO: 37, which has a corresponding modified DNA sequence of SEQ ID NO: 38.

In another embodiment, the Wild Type portal protein of SEQ ID NO: 1 can be modified in the tunnel loop residue of the hydrophilic protein channel, the modification comprising an expansion of the narrowest constriction of the tunnel loop of SEQ ID NO: 1, a restriction of the narrowest constriction of the tunnel loop of SEQ ID NO: 1, or a removal of the narrowest constriction of the tunnel loop of SEQ ID NO: 1. For such purposes, the hydrophilic protein channel can, for example, comprise one of the G, M, CGG, Loop2GG and 49CLoop3G variants, which have, respectively, the amino acid sequences of SEQ ID NO: 15, SEQ ID NO: 17, SEQ ID NO: 21, SEQ ID NO: 23, and SEQ ID NO: 25, and the corresponding modified DNA sequences of SEQ ID NO: 16, SEQ ID NO: 18, SEQ ID NO: 22, SEQ ID NO: 24, and SEQ ID NO: 26.

In another embodiment, the Wild Type portal protein of SEQ ID NO: 1 can be modified in the tunnel loop residue of the hydrophilic protein channel, the modification comprising an alteration of an electrostatic charge property of the tunnel loop of SEQ ID NO: 1. For this purpose, the hydrophilic protein channel can, for example, comprise the K variant, which has amino acid SEQ ID NO: 19 and corresponding modified DNA sequence of SEQ ID NO: 20.

In another embodiment, the Wild Type portal protein of SEQ ID NO: 1 can be modified to alter an external charge of the hydrophilic protein channel. For example, for such a purpose, the hydrophilic protein channel can comprise one of the L230E and 40E variants, which respectively have amino acid SEQ ID NO: 9 and SEQ ID NO: 13, and corresponding modified DNA sequences SEQ ID NO: 10 and SEQ ID NO: 14.

In another embodiment, the Wild Type portal protein of SEQ ID NO: 1 can be modified to promote binding of the hydrophilic protein channel to the solid-state matrix. For example, for such a purpose, the hydrophilic protein channel can comprise one of the SIN1, SIN2 and SIN 4 variants, which respectively have amino acid SEQ ID NO: 29, SEQ ID NO: 31 and SEQ ID NO: 35, which have corresponding modified DNA sequences of SEQ ID NO: 30, SEQ ID NO: 32 and SEQ ID NO: 36.

In another embodiment, the Wild Type portal protein of SEQ ID NO: 1 can be modified to extend the N-terminal of a cleaved portion of SEQ ID NO: 1. For example, for such a purpose, the hydrophilic protein channel can comprise the SIN3 variant, which has amino acid SEQ ID NO: 33, and corresponding modified DNA sequence SEQ ID NO: 34.

In another embodiment, the Wild Type portal protein of SEQ ID NO: 1 can be modified to cleave off the amino acid residue of at least one of the C-terminal region and the N-terminal region of SEQ ID NO: 1. For example, for such a purpose, the modification can comprise a modification of one of the WT 1-438 C-term, WT 1-438 3C prot and WT Nanopore variants, for which the amino acid sequences are respectively given by SEQ ID NO: 3, SEQ ID NO: 5 and SEQ ID NO: 7, and for which the corresponding modified DNA sequences are SEQ ID NO: 4, SEQ ID NO: 6 and SEQ ID NO: 8.

In another embodiment, the Wild Type portal protein of SEQ ID NO: 1 can be modified in one or more of: a wing loop residue (such as residues in the range 36-41 or 46-54), a tunnel loop residue (such as residues in the range 316-335), an upper internal surface residue (such as residues in the range 381-400), a lower internal surface residue (such as residues in the range 273-303), an external surface residue (for example, residue 230), a C-terminal end residue (for example, residues 435-436), and an N-terminal end residue (for example, residue 29).

In addition, attachment of the portal protein to the solid-state surface can, for example, be assisted using vapor deposition of maleimide/thiol-silane compounds; by silicon binding peptides, such as binders to either, or both, SiN or SiOx; or by thiocholesterol or other maleimide-lipid conjugated to L49C by thiol chemistry. The solid-state matrix may comprise a coating to promote binding of the solid-state matrix to the hydrophilic protein channel. For example, the coating may comprise a thiol-coupling compound; and may, for example, comprise a maleimide compound or other thiol-coupling compound.

Although some embodiments herein are discussed based on use of a modified portal protein of the *Thermus thermophilus* bacteriophage G20c, it should be appreciated that portal proteins from other bacteriophages (including bacteriophages of *Thermus thermophilus*, and other bacteriophages) can be used, including any hydrophilic portal protein that achieves performance of a similar function to the hydrophilic protein channel in a stable insertion fit within a solid-state pore opening, that is taught herein. In one example, the portal protein of the *Thermus thermophilus* bacteriophage P23-45, or modifications of that portal protein, can be used. In that regard, SEQ ID NO: 40, or a modified protein based on SEQ ID NO: 40, can be used; and a protein encoded by its DNA sequence, which is SEQ ID NO: 41, or a modified protein encoded by a modified DNA of SEQ ID NO: 41, can be used. In particular, one or more of three amino acid variations of SEQ ID NO:1 can be made, which results in SEQ ID NO: 40, or a modification thereof: at residue 328 of SEQ ID NO: 1, there is an I amino acid residue, which, if changed to V, becomes the amino acid residue 328 of SEQ ID NO: 40; at residue 189 of SEQ ID NO: 1, there is an S amino acid residue, which, if changed to an N amino acid residue, becomes the amino acid residue 189 of SEQ ID NO: 40; and at amino acid residue 367 of SEQ ID NO: 1, there is an S residue, which, if changed to a G amino acid residue, becomes amino acid residue 367 of SEQ ID NO: 40. Thus, a mutation at one or more of amino acid residue locations 328, 189 and/or 367 of SEQ ID NO: 1 can be used.

In addition, it should be noted that monomer protein units of proteins taught herein can be assembled to form the full portal protein that functions to form the stable insertion fit within a solid-state pore opening that is taught herein. For example, the portal protein of the *Thermus thermophilus* bacteriophage G20c forms a dodecameric structure, made of 12 monomer protein units, which together assemble to form the full "plug" protein (see FIG. 4) that forms a stable insertion fit within the solid-state pore opening. Thus, a "hydrophilic protein channel," as used herein, can include more than one monomer of a protein, such as 12 monomer protein units assembled together to form the hydrophilic protein channel through the dodecameric combined protein structure assembled from the monomers of the protein.

EXAMPLES

There will now be described a set of example experiments, conducted in accordance with an embodiment of the invention.

Example 1

Figure 6:
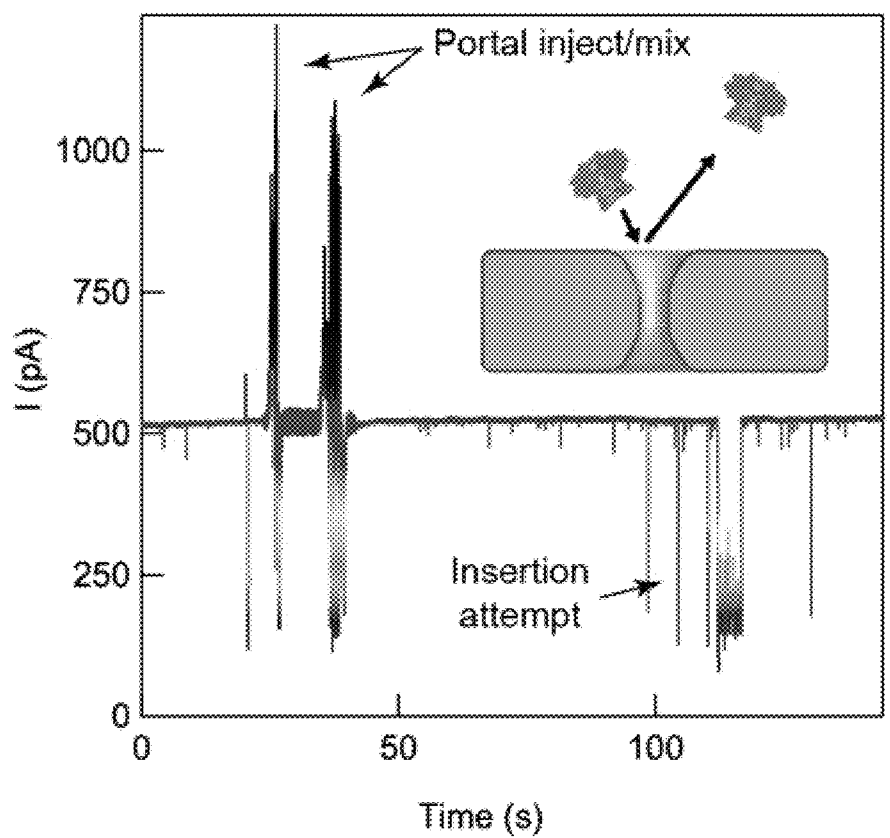
FIGS. 6-10 are graphs showing characterization of hybrid pore formation, in experiments in accordance with an embodiment of the invention.
Figure 7:
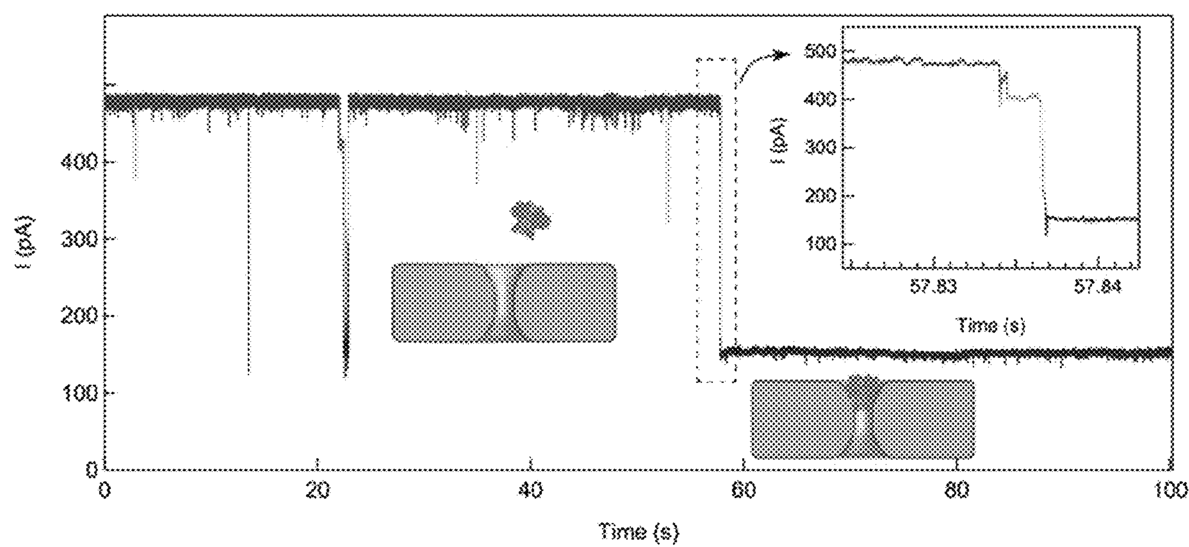
Figure 8:
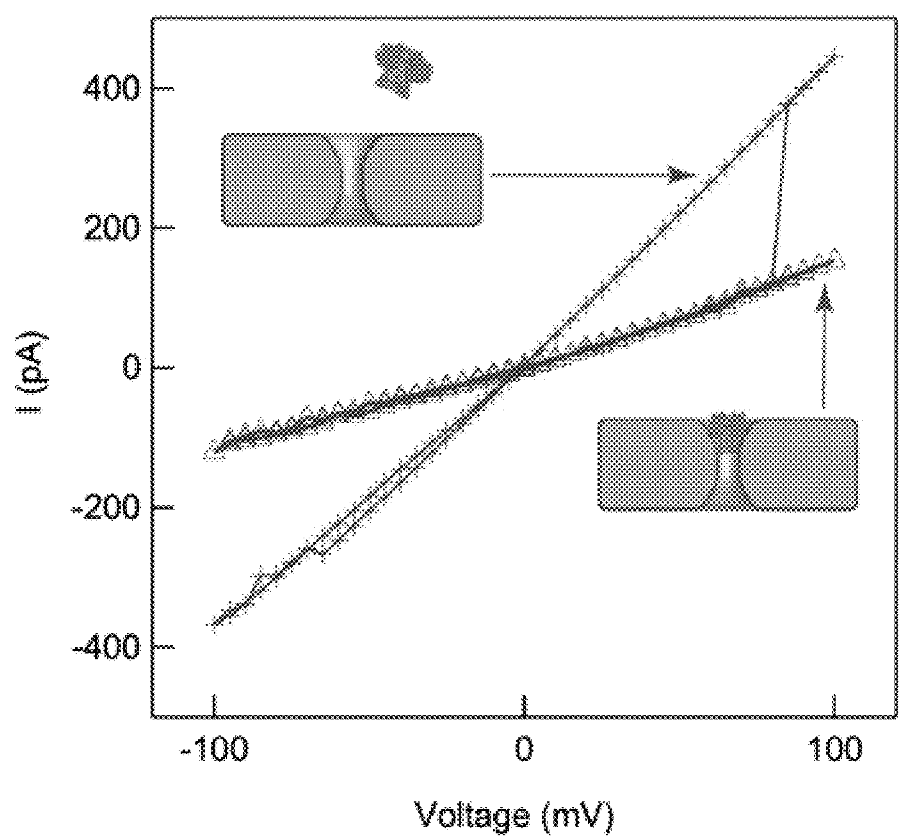
Figure 9:
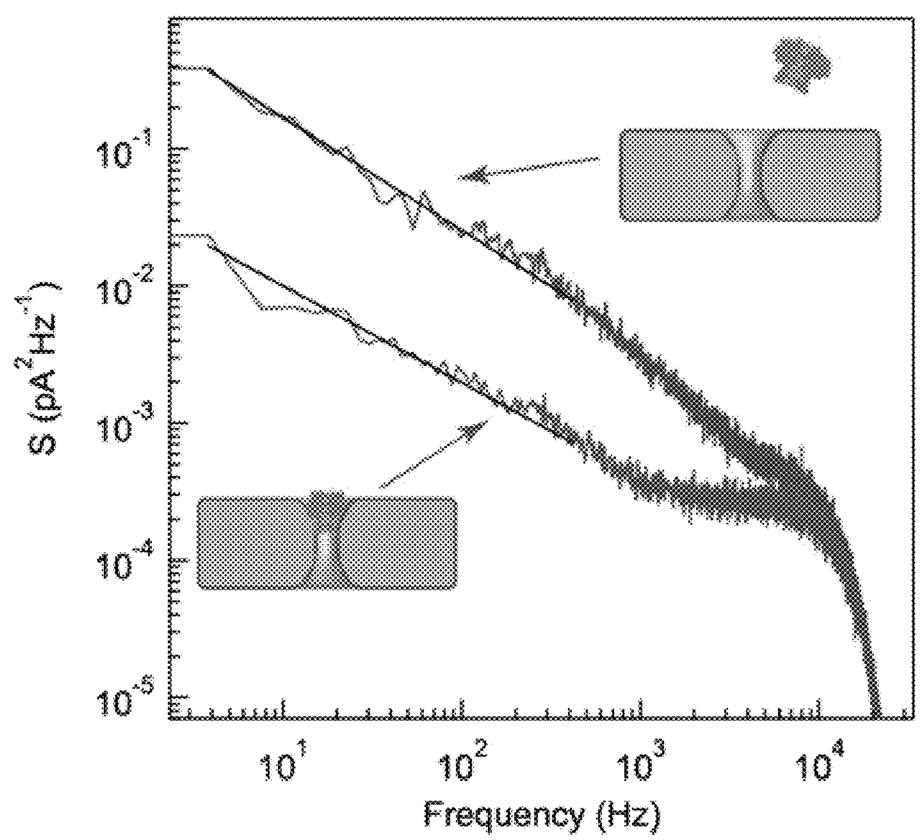
Figure 10:
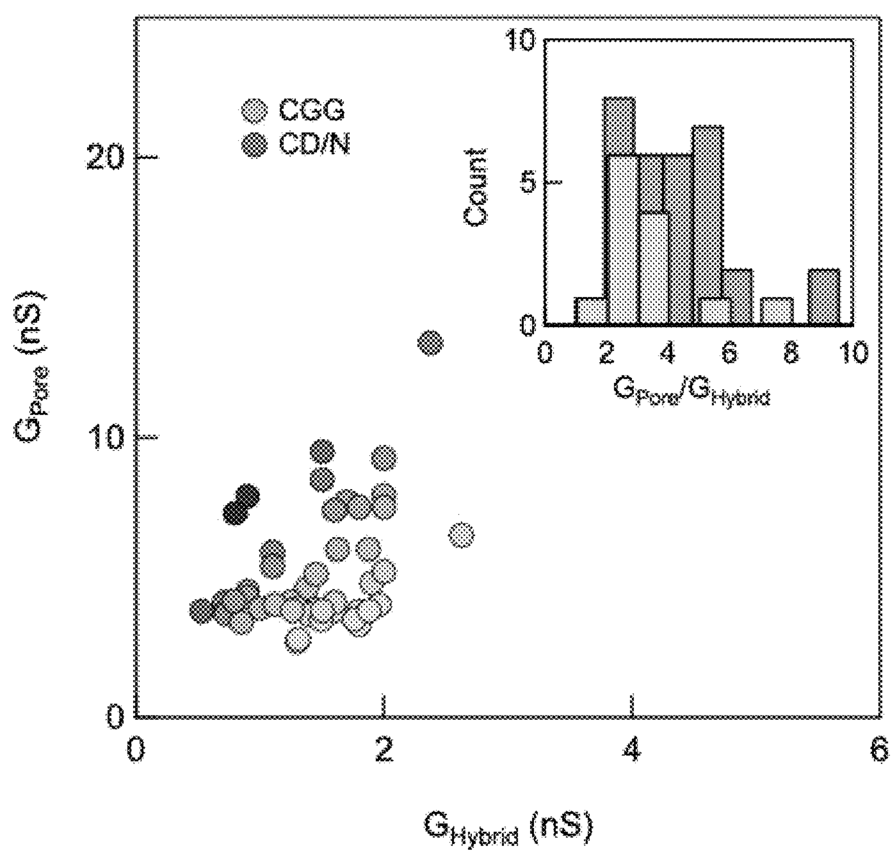

FIGS. 6-10 are graphs showing characterization of hybrid pore formation, in experiments in accordance with an embodiment of the invention. FIG. 6 is a graph of a typical current profile over time recorded through a 5.5 nm SS pore at +100 mV. After injection of 0.1 nmol of portal protein, short current drops are detected, interpreted as portal collisions with the solid-state nanopore. FIG. 7 is a graph of a representative current vs time trace recorded for a 5.4 nm SS nanopore at +80 mV, showing stable insertion of a portal protein. FIG. 8 is a graph of current as a function of the applied voltage for a 5.5 nm SS pore recorded before (red markers, with a higher slope) and after insertion of a portal protein (purple, with a lower slope). FIG. 9 is a graph of current noise analysis of a 5.5 nm diameter solid-state nanopore before (red, top curve) and after insertion of a portal protein (purple, bottom curve). FIG. 10 is a graph of conductance of solid-state nanopore vs conductance of portal hybrid pore (n=32 for CD/N hybrids and n=15 for CGG hybrids). Experiments were performed in 0.5 M NaCl, 20 mM Tris pH 7.5.

In experiments in accordance with an embodiment of the invention, the hybrid nanopores exhibit lifetimes of hours, and similar ion current noise values to a lipid bilayer-supported portal protein nanopore (33) (see FIGS. 6-10). The electrical properties of the hybrid pore were characterized and applied to electrically detect different biomolecules. Using the hybrid portal with engineered internal pore properties (CD/N, see FIG. 2, right), it was demonstrated that a folded protein larger than the pore interior does not enter the hybrid portal, whereas homopolymeric single-stranded DNA (ssDNA), double-stranded DNA (dsDNA) that contains a single-stranded tail, and a peptide predicted to have a random coil conformation with a 10-amino acid α-helix at the C-terminus, can all be discriminated based on their distinct signal amplitudes, in a way that is commensurate with their molecular cross-section. The results indicate that the hybrid portal is a versatile sensor of various biopolymer types, which may, with further development, find uses in genomic mapping as well as polypeptide and oligonucleotide sequencing.

After confirming the base current of stable SS nanopores of the desired diameter, addition of the portal protein to the trans chamber results in reversible partial blockades of the ionic current (FIGS. 6 and 7). These short-lived events are interpreted as portal protein collisions with the SS nanopore without stable insertion, where the ion current is partially blocked as the protein approaches the SS pore, prior to movement away. These short-lived events were usually followed by long-lived events (FIG. 7), of comparable current blockade levels, events that were only observed in SS pores with diameters of 5.4 to 6 nm. The long-lived events are interpreted as stable insertion of a portal protein into the SS nanopore to form a hybrid nanopore. The average conductance of these hybrid pores was calculated (FIG. 10) to be 1.50±0.48 nS and 1.33±0.42 nS for the CD/N (from 32 hybrid nanopores) and the CGG (from 15 hybrid nanopores) variants, respectively. Such hybrid pores remain stable at both positive and negative voltages up to +120 mV and −80 mV (FIG. 8), however, application of an electric field with strengths greater than −80 mV generally resulted in release of the protein from the SS nanopore. These data are consistent with the protein insertion being electrokinetically driven.

Obtaining a sufficient increase in the signal-to-noise ratio is a major challenge for properly identifying transport events by nanopore sensing. Power spectral densities of the current noise for a SS nanopore before, and after, insertion of a portal protein (FIG. 9) showed that the 1/f noise at low frequencies decreased upon formation of the hybrid pore.

This 1/f noise reduction is consistent with a reduced pore conductance, as well as an indicator of the reduced surface charge fluctuations that are hallmarks of silicon nitride surfaces (39). This, along with the observation that capacitance-dominated noise at high frequencies was comparable for both pores, suggests that no new source was introduced during hybrid pore formation. It was deduced that the observed variation in the open pore current for different hybrid nanopores was likely to be caused by differences in SS geometry and the associated leakage currents around the portal protein. It was attempted to measure the extent of ion leakage from the pore by measuring β-cyclodextrin interactions with the hybrid pore for the CGG mutant, a mutant that was previously embedded into a lipid membrane (33). The results show that β-cyclodextrin does not translocate the pore, in contrast for the same experiment conducted on the lipid-embedded version of the same portal protein. While this precludes an accurate measurement of the leakage, these results suggest that "corking" the protein into a snug SS nanopore slightly reduces the innermost pore constriction. The reproducible signals obtained from biomolecules, as well as the steady baselines of the hybrid, allow current blockades as low as ~20 pA to be accurately measured. These data demonstrate that despite a low level of constant peripheral leakage, these hybrid pores are unique lipid-free protein-based pore sensors.

Example 2

The sensing capabilities of these hybrid nanopores were then investigated by analyzing the transport of a peptide, comprising residues 1-43 of the human TPX2 protein, as a function of applied voltage (FIGS. 11A-11C).

FIGS. 11A-11C are graphs showing dynamics of TPX2 peptide transport, in experiments in accordance with an embodiment of the invention. FIG. 11A is a graph showing a current vs time trace recorded through a hybrid pore at +30, +40 and +55 mV in the presence of 10.3 μM TPX2 peptide. FIG. 11B is a semi-log plot of the event frequency as a function of the applied voltage. The line is an exponential fit to the equation. FIG. 11C is a semi-log plot of the peptide dwell time as a function of the applied voltage. The lines in FIGS. 11B and 11C are exponential fits. Experiments were performed in 0.5 M NaCl, 20 mM Tris pH 7.5.

The TPX2 peptide is negatively charged at pH 7.5 (pI=3.7) and was added to the cis chamber, on the opposite side of the membrane to which the portal protein was introduced (see inset to FIG. 11B). Adjusting the applied voltage from +30 to +60 mV resulted in an increased baseline ion current through the hybrid pore, as well as the frequency of observed current blockades (FIG. 11A). Two kinds of current blockades associated with two different events were detected: bumping events, characterized by brief, low-level current blockades, arising from diffusion of the peptide close to the hybrid pore entrance; and translocation events, characterized by larger current blockades of longer duration. These two types of events are typically seen during translocation of DNA (40-42) and proteins (43-45) through protein channels. The inter-event time distribution is well fit by a single exponential equation. The entry frequency (FIG. 11B) of the peptide into the hybrid pore is described by a Van't Hoff Arrhenius relationship (44,46), $f=f_0 \exp(V/V_0)$, consistent with both translocation of DNA (40-42), proteins (43,47) and peptides (46, 48-51) through either α-hemolysin or aerolysin; and a significant entropic barrier for peptide entry into the pore. The dwell time distributions were well fit by a double-exponential equation, which are typically due to two types of processes, normally associated with short bumping and longer translocation events (16). It was found that the average frequency for both types of events increases exponentially (FIG. 11B), while the average dwell time for the long events decreased exponentially with the applied voltage (FIG. 11C). Based on prior work that employed the α-hemolysin and aerolysin nanopores, (43, 45) it was concluded that the long events represent transport of the peptide through the hybrid pore to the trans chamber.

Example 3

In order to further demonstrate the sensing capabilities of this hybrid pore, the transport of other biopolymers was further investigated: dsDNA that contains a ssDNA tail, ssDNA, a folded protein as well as the TPX2 peptide (FIGS. 12A-12E).

Figures 12A, 12E:
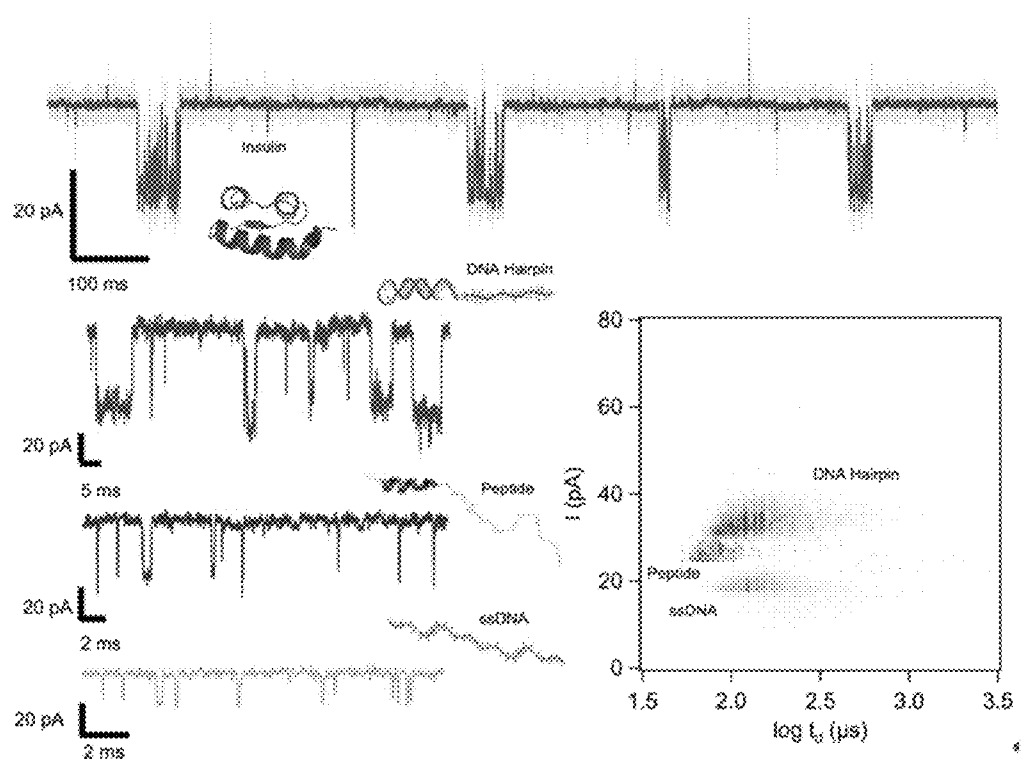

FIGS. 12A-12E are graphs illustrating sensing of different biopolymers using a hybrid nanopore, in experiments in accordance with an embodiment of the invention. Current vs time trace recorded through the hybrid pore at +60 mV in the presence of (FIG. 12A) 36.0 μM insulin, (FIG. 12B) 7.7 μM DNA hairpin, (FIG. 12C) 10.3 μM TPX2 peptide and (FIG. 12D) 16.6 μM ssDNA. The data in (FIG. 12A) were filtered at 10 kHz (grey) or 0.5 kHz (green). FIG. 12E is a scatter plot of ΔI vs dwell time for the DNA hairpin (red), the peptide (purple) and the ssDNA (orange). Experiments were performed in 0.5 M NaCl, 20 mM Tris pH 7.5.

Since all of these polymers are negatively charged at pH 7.5, following their addition to the cis chamber (the opposite side of the SS membrane to portal insertion), electrophoresis allows molecular capture into the base of the portal protein. After addition of each biopolymer: 36.0 μM Insulin (FIG. 12A); 7.7 μM hairpin-poly$dT_{50}$ (FIG. 12B); 10.3 μM TPX2 peptide (FIGS. 11A-11C and 12C); 6.9 μM 60 bp-poly$dT_{30}$; and 16.6 μM ssDNA poly$dA_{20}dC_{20}dA_{20}$ (FIG. 12D); reversible partial blockades of the ionic current are observed at +60 mV. Similar short-lived bumping events as well as longer events were observed for each biopolymer, as described above for the TPX2 peptide (FIGS. 11A-11C). These types of blockades were also observed at several different voltages for DNA molecules, with voltage dependent changes in event frequency and duration for ssDNA poly$dA_{20}dC_{20}dA_{20}$ consistent with translocation occurring, as noted for the peptide above (FIGS. 11A-11C). Conversely, the folded, globular molecule of insulin, with a smallest dimension of ~3 nm (PDB code: lzeh) (52, 53) is too large for the ~2 nm constriction of the hybrid pore and therefore does not translocate. It is however possible that insulin explores the cavity at the portal tunnel's entrance (~5 nm) without being transported to the trans chamber, producing structured events that are long-lived and have a low current blockade level. Such events have been previously observed for nanoreactors, where biomolecules are "captured" or "tethered" within ClyA and FracC nanopores (20, 54).

Lastly, the event characteristics for different biopolymers were compared at the same applied voltage of +60 mV by overlaying their scatter plots of ΔI vs. dwell times, as shown in FIG. 12E. The level of current blockade, ΔI, appeared to be biopolymer dependent. Current blockades were found for the dsDNA (FIG. 12E) of ΔI=34.6±4.2 pA, while in contrast, ΔI=18.1±3.2 pA was found for ssDNA. This is nearly two times less than for the partially dsDNA, and is consistent with values found for dsDNA and ssDNA in SS nanopores (55), where the difference in conductance was found to be ~2.75 fold. For the peptide, ΔI=30.1±5.5 pA was found. Since it was shown that the peptide is transported through the pore (FIGS. 11A-11C) and the peptide is predicted to contain an α-helix of ~1.4 nm in diameter as seen in the structure of the TPX2 peptide bound to its partner kinase, Aurora A (PDB: 10L5), the data are compatible with translocation through the narrowest constriction of the hybrid pore (~2 nm diameter). The ΔI value found for the peptide is consistent with the α-helical region being the main cause of the blockade, and with its diameter being intermediate between that of dsDNA and ssDNA. These data suggest that the predicted α-helix is present in the isolated peptide under these experimental conditions. While transport of structured biopolymers has been reported for nucleic acids (56, 57), it is believed that only a single report presents transport of an α-helical peptide through a protein nanopore (45).

Hybrid nanopores, supported by SS membranes could offer superior properties to both the planar lipid bilayer based pores (that are sensitive to temperature, osmotic pressure, and applied electric field strength and not geometrically controllable) and SS nanopores (that are prone to edge erosion and difficult to reproducibly fabricate with diameters <5 nm). However, despite having been the subject of industrial and academic research, development of a device that can be easily fabricated, has proven difficult. For example, producing a hybrid pore based on the α-hemolysin, a membrane protein, noted relatively short hybrid pore lifetime and required complex protein modifications (35). In contrast, the hybrid nanopore described here is based on a soluble, stable and relatively hydrophilic viral portal protein, whose chemical properties, including those inside tunnel, can be easily tuned.

An embodiment demonstrates biomolecule sensing capabilities of a novel lipid-free hybrid nanopore comprising the G20c portal protein inserted into a thin SS SiN membrane. This hybrid pore is easy to assemble, with the portal protein readily electrokinetically inserting into the SS-pores and typically remaining stable for hours of experimental time. The electrical sensing data clearly show characteristic readout for ds and ssDNA, as well as a peptide and a globular protein. The hybrid pore demonstrates utility as a nanosensor.

Materials and Methods

1. Preparation of CGG and CD/N

To produce the mutant portal protein, CGG, the following procedure was followed. An analogous procedure was used to produce a different mutant portal protein, CD/N. The following method of cloning, expression and purification of G20C portal proteins was used (here described for CGG and 49C mutants). The DNA encoding for G20c portal protein (residues 25-438) was amplified by PCR using Phusion high fidelity DNA polymerase (New England Biolabs, Ipswich, Massachusetts, U.S.A.), and cloned into the YSBL-Lic+ (Bonsor, D.; Butz, S. F.; Solomons, J.; Grant, S.; Fairlamb, I. J. S.; Fogg, M. J.; Grogan, G. Ligation Independent Cloning (LIC) as a Rapid Route to Families of Recombinant Biocatalysts From Sequenced Prokaryotic Genomes. *Org. Biomol. Chem.* 2006, 4, 1252-1260) expression plasmid encoding an N-terminal 3C protease cleavable hexahistidine tag using the HiFi DNA assembly master mix (New England Biolabs, Ipswich, Massachusetts, U.S.A.). All mutant variations of the wild-type (WT) protein were produced using a variation of the linear exponential PCR and ligase-dependent production of closed circular plasmid DNA using Phusion DNA polymerase (New England Biolabs, Ipswich, Massachusetts, U.S.A.). Briefly, primer sets were designed to introduce the mutation(s) and amplify the entire plasmid by PCR, after which the DNA product was purified using a PCR cleanup kit (Thermofisher). Phosphorylation and ligation of the amplified DNA ends and Dpn I digest of the template plasmid was achieved in a 3 h reaction at 37° C., containing 1× Cutsmart buffer (New England Biolabs, Ipswich, Massachusetts, U.S.A.), 1 mM ATP, 10 mM DTT, and 1 unit each of Dpn I, T4 polynucleotide kinase, T4 ligase (New England Biolabs, Ipswich, Massachusetts, U.S.A.). Ligated closed circular plasmid DNA was transformed into competent DH5a cells. Mutants were screened by colony PCR and confirmed by DNA sequencing in both directions.

Wild type and mutant proteins G20c WT (WT) and G20c V325G_I328G (GG)) were expressed and purified from *E. coli* BL21 (DE3) pLys S cells. Proteins containing cysteine mutants, G20c-L49C (49C) and G20c-L49C_V325G_I328G (CGG) were expressed and purified from the SHuffle (New England Biolabs, Ipswich, Massachusetts, U.S.A.) expression strain. Protein expression and purification was conducted as described (Williams, L. S.; Levdikov, V. M.; Minakhin, L.; Severinov, K.; Antson, A. A. 12-Fold Symmetry of the Putative Portal Protein From the *Thermus Thermophilus* Bacteriophage G20C Determined by XRay Analysis. *Acta Crystallogr., Sect. F: Struct. Biol. Cryst. Commun.* 2013, 69, 1239-1241.) in LB (Melford) containing 35 μg/mL kanamycin and 50 μg/mL chloramphenicol. Briefly, 10 mL of an overnight culture was inoculated into 1 L of LB (containing antibiotics) and incubated at 37° C. until the $OD_{600}$ reached 0.8, followed by induction overnight at 16° C. with 0.5 mM IPTG when the cells were harvested by centrifugation at 4000 rpm for 30 min and the pellets snap frozen in liquid nitrogen and stored at ~80° C. until use. Proteins (49C and CGG) expressed in Shuffle cells were incubated at 30° C. before and after induction. Cell pellets were thawed and resuspended in 5 mL/g of lysis buffer (50 mM Tris pH 8, 1 M NaCl, 10 mM imidazole, 100 mM AEBSF, 10 mg/mL lysozyme) and lysed by sonication on ice. The lysate was clarified by centrifugation at 15000 rpm for 30 min, filtered through a 0.22 μm membrane before loading on a HisTrap FF 5 mL (GE Healthcare Life Sciences). The His-tagged G20c protein was eluted using a gradient to 100% Buffer B (1 M NaCl, 50 mM Tris pH 7.5, 500 mM imidazole) over 10 column volumes. Fractions of the purified protein were pooled, buffer exchanged into 50 mM Tris pH 8, 500 mM NaCl 50 mM potassium glutamate, and the histidine tag removed by 3C protease digestion at rt overnight. The cleaved protein was then further purified over a HisTrap FF 5 mL. Fractions containing cleaved G20c protein were pooled, concentrated, and finally purified on a 16/600 Superose 6 (GE healthcare Life Sciences) gel filtration column in 20 mM Tris pH8, 1 M NaCl, 50 mM potassium glutamate, concentrated by ultrafiltration using a 100 kDa cutoff filter (Vivaspin) to ~4 mg/mL for biophysical experiments or ~10 mg/mL for crystallographic studies, snap frozen on liquid nitrogen and stored at −80° C. Proteins containing the L49C mutation were purified in buffers containing 2 mM DTT.

Likewise, other mutant proteins taught herein were expressed and purified in a similar fashion as described in the preceding paragraph.

2. Protein Engineering and Purification:

Mutant portal proteins, CGG (33) was produced as described in Section 1 ("Preparation of CGG and CD/N"), above, in *E. coli*, and CD/N was prepared in an analogous fashion, with the exception that two buffer exchange steps over a desalting column (GE Healthcare) were used to improve 3C cleavage of the histidine affinity tag (50 mM Tris pH 8, 500 mM NaCl, 50 mM K Glutamate, 1 mM DTT)

prior to a second IMAC step and purification to homogeneity in 20 mM Tris pH 8, 1 M NaCl, 1 mM DTT, before freezing in liquid nitrogen and storage at −80° C. Protein was exchanged into 20 mM Tris pH 7.5, 0.5 M NaCl buffer (Zeba Spin Columns, Thermofisher) for use in hybrid nanopore formation. CD/N mutant proteins where characterized for stability and assembly state by nanoDSF and negative stained TEM.

3. Experimental Set-Up:

Nanopores were fabricated in 30 nm thick SiN membranes using previously reported methods (58,59). The pore diameters ranged between 5.4 and 6 nm in order to squeeze properly the portal protein. Nanopores were cleaned with hot piranha (3:1 $H_2SO_4/H_2O_2$), followed by hot deionized water before each experiment. After being dried under vacuum, nanopore chips were assembled in a custom cell equipped with Ag/AgCl electrodes, and quick-curing silicone elastomer was applied between the chip and the cell to seal the device and thereby reduce the noise by minimizing the chip capacitance. We introduced 0.5 M NaCl, 20 mM Tris pH 7.5 as an electrolyte solution onto both sides of the chip. Portal protein was always added to the trans chamber and the biopolymers to the cis chamber. All experiments were carried out at ambient temperature. Human insulin was purchased from Alfa Aesar (Thermofisher), dsDNA Hairpin (5'-GCTGTCTGTTGCTCTCTCGCAACAGACAGC $T_{50}$-3'), ssDNA (5'-$dA_{20}dC_{20}dA_{20}$-3'), 60 bp-polydT30 ((5'-TCAGGGTTTTTTTACT)$_4$ $T_{30}$-3') and its complementary strand ((3'-AGTAAAAAAACCCTGA-5')$_4$) were synthesized by Integrated DNA Technology.

4. Electrical Detection and Data Acquisition:

The ionic current through SS nanopores and portal hybrid protein was measured using an Axopatch 200B amplifier (Molecular Devices). Data were filtered at 10 kHz and acquired at 250 kHz using the DigiData 1200 digitizer with a custom National Instruments LabVIEW program. Data was processed and events were detected using Pythion software (https://github.com/rhenley/Pyth-Ion/). The values for the open pore current ($I_0$) and the standard deviation of the noise (a) was extracted. (The threshold (Th) applied in Pythion to separate events from the noise is given by $Th=I_0-4\sigma$. The average duration of blockades is deduced from the distribution of blockade duration, $\tau_t$. The two blockade time distributions of independent events are adjusted with a double exponential function, $y=A_1 \exp(t/\tau_1) A_2\exp(t/\tau_2)$. All statistical analyses were performed using Igor Pro software (WaveMetrics Inc.).

Definitions and Discussion of Terminology

As used herein, a "protein" is a biological molecule consisting of one or more chains of amino acids. Proteins differ from one another primarily in their sequence of amino acids, which is dictated by the nucleotide sequence of the encoding gene. A peptide is a single linear polymer chain of two or more amino acids bonded together by peptide bonds between the carboxyl and amino groups of adjacent amino acid residues; multiple peptides in a chain can be referred to as a polypeptide. Proteins can be made of one or more polypeptides. Shortly after or even during synthesis, the residues in a protein are often chemically modified by posttranslational modification, which alters the physical and chemical properties, folding, stability, activity, and ultimately, the function of the proteins. Sometimes proteins have non-peptide groups attached, which can be called prosthetic groups or cofactors.

As used herein, a "protein variant" refers to a protein that differs from a reference peptide by one or more modifications, for example, substitutions, insertions or deletions, and is not naturally occurring. A protein variant can include an isolated protein, which is not naturally occurring, and is free from the cell, or other proteins in a medium, in which it was produced. An isolated protein is a protein or fragment thereof that is substantially free of other proteins, and encompasses proteins that are isolated to a higher purity, such as proteins that are 80%, 81%, 82%, 83%, 84%, 85%, 86%, 87%, 88%, 89%, 90%, 91%, 92%, 93%, 94%, 95%, 96%, 97%, 98%, 99% or 100% pure. The protein can, for example, be isolated from the extracellular medium in which the microorganism to be assayed is growing, or from the cell membrane of the microorganism, using standard protein purification techniques, described, for example, in (See, e.g., Ausubel, F. M. et al. ("*Current Protocols in Molecular Biology*", John Wiley & Sons, (1998) the entire teachings of which are incorporated herein by reference).

The proteins of embodiments also encompass fragments and sequence variants of the proteins described herein. Variants include a substantially homologous protein encoded by the same genetic locus in an organism, i.e., an allelic variant, as well as other variants. Variants also encompass proteins derived from other genetic loci in an organism. Variants also include proteins substantially homologous or identical to these proteins but derived from another organism and/or d and 1 isomers (i.e., an ortholog), produced by chemical synthesis, or produced by recombinant methods.

In some embodiments, the protein variant comprises an amino acid sequence, such as one of the sequences listed herein or a sequence having at least 50%, 60%, 70%, 80%, 85%, 90%, 95%, or 99% sequence identity to one of the sequences listed herein, as determined using a sequence comparison program and parameters described herein.

The percent identity of two amino acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions×100). In certain embodiments, the length of the amino acid sequence aligned for comparison purposes is at least 30%, preferably, at least 40%, more preferably, at least 60%, and even more preferably, at least 70%, 80%, 90%, or 100% of the length of the reference sequence. The actual comparison of the two sequences can be accomplished by well-known methods, for example, using a mathematical algorithm. A preferred, non-limiting example of such a mathematical algorithm is described in Karlin et al., 90 PROC. NAT'L ACAD. SCI. USA 5873-77 (1993), which is incorporated herein by reference. Such an algorithm is incorporated into the BLAST programs (version 2.2) as described by Schaffer et al., 29 NUCLEIC ACIDS RES. 2994-3005 (2001), which is incorporated herein by reference. When utilizing BLAST and Gapped BLAST programs, the default parameters of the respective programs can be used. In one embodiment, the database searched is a non-redundant database, and parameters for sequence comparison can be set at: no filters; Expect value of 10; Word Size of 3; the Matrix is BLOSUM62; and Gap Costs have an Existence of 11 and an Extension of 1.

In another embodiment, the percent identity between two amino acid sequences can be determined by using the GAP program in the GCG software package (available from Accelrys, Inc. of San Diego, CA) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be determined using a gap weight of 50 and a length weight of 3. Other preferred sequence comparison methods are described herein.

The invention also encompasses proteins having a lower degree of identity but having sufficient similarity so as to perform one or more of the same functions performed by a protein encoded by a nucleic acid molecule of the invention (e.g., the ability to provide the hydrophilic protein channel in a stable insertion fit within a solid-state pore opening). Similarity is determined by conserved amino acid substitution. Such substitutions are those that substitute a given amino acid in a peptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., SCIENCE 247:1306-10 (1990), which is incorporated herein by reference.

Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncations or a substitution, insertion, inversion, or deletion in a critical residue or critical region.

The invention also includes protein and peptide fragments of the amino acid sequences of the various mentioned proteins or variants (e.g., functional variants) thereof.

Fragments can be discrete (not fused to other amino acids or peptides) or can be within a larger peptide. Further, several fragments can be comprised within a single larger peptide. The peptides can, for example, be produced using standard recombinant protein techniques (See, e.g., Ausubel, F. M. et al. ("*Current Protocols in Molecular Biology*", John Wiley & Sons, (1998) the entire teachings of which are incorporated herein by reference). In addition, the proteins of the present invention can also be generated using recombinant techniques.

In some embodiments, protein variants are produced by mutation of amino acid sequences, but protein variants in embodiments can also be produced by removing or adding one or more amino acid residues through other well-known means, including chemical synthesis.

As used herein, a "modification" of a protein refers to a substitution, insertion or deletion of one or more amino acids.

As used herein, a "modification of an amino acid sequence" refers to a mutant amino acid sequence that is not naturally occurring, and that has a mutation relative to a reference amino acid sequence, that is, by an alteration of the amino acid sequence of the reference amino acid sequence, such as by substitution, insertion or deletion of one or more amino acid residues.

As used herein, "nucleic acid" refers to a macromolecule composed of chains (a polymer or an oligomer) of monomeric nucleotide. The most common nucleic acids are deoxyribonucleic acid (DNA) and ribonucleic acid (RNA). It should be further understood that the present invention can be used for sensing biomolecules containing artificial nucleic acids such as peptide nucleic acid (PNA), morpholino, locked nucleic acid (LNA), glycol nucleic acid (GNA) and threose nucleic acid (TNA), among others. In various embodiments of the present invention, nucleic acids can be derived from a variety of sources such as bacteria, virus, humans, and animals, as well as sources such as plants and fungi, among others. The source can be a pathogen. Alternatively, the source can be a synthetic organism. Nucleic acids can, for example, be genomic, extrachromosomal or synthetic. In addition, the term "nucleic acid," is used herein to include a polymeric form of nucleotides of any length, including, but not limited to, ribonucleotides or deoxyribonucleotides. Further, the term refers only to the primary structure of the molecule. Thus, in certain embodiments the term can include triple-, double- and single-stranded DNA, PNA, complementary DNA (cDNA), as well as triple-, double- and single-stranded RNA. It can also include modifications, such as by methylation and/or by capping, and unmodified forms of a polynucleotide. More particularly, the term "nucleic acid," includes polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from Anti-Virals, Inc., Corvallis, Oreg., U.S.A., as Neugene) polymers, and other synthetic sequence-specific nucleic acid polymers providing that the polymers contain nucleobases in a configuration which allows for base pairing and base stacking, such as is found in DNA and RNA. In addition, a "nucleic acid" can include a plasmid DNA (pDNA), such as a plasmid DNA vector.

As used herein, a "modification of a nucleic acid sequence" refers to a mutant nucleic acid (e.g., DNA) that is not naturally occurring, and that has a mutation relative to a reference nucleic acid, that is, by an alteration of the nucleotide sequence of the reference nucleic acid sequence, such as by substitution, insertion or deletion of one or more nucleotides. In some embodiments, the mutation can be a missense mutation, which is a type of nonsynonymous substitution that is a point mutation in which a single nucleotide change results in a codon that codes for a different amino acid. In some embodiments, modifications of a nucleic acid sequence produce modified proteins and peptides described herein.

In some embodiments, a nucleic acid molecule comprising a modification of a nucleic acid sequence can be isolated or recombinant. In addition, such a modification of a nucleic acid sequence can be produced using techniques of cell-free protein synthesis, which produce protein using biological machinery in a cell-free system, without the use of living cells. Cell free expression systems can, for example, be used, that use linear DNA sequences propagated by polymerase chain reaction (PCR) reactions.

As used herein, a "vector" is a molecule, e.g., a plasmid or virus designed for gene expression in cells. The vector is used to introduce a specific gene into a target cell, and can commandeer the cell's mechanism for protein synthesis to produce the protein encoded by the gene. In addition, in some embodiments, a "vector" comprising a modification of a nucleic acid sequence can refer to any DNA plasmid containing the sequence for propagation of the DNA plasmid and/or for expression of the peptide encoded by the modification of a nucleic acid sequence in any cellular system (such as a bacteria, yeast or eukaryotic cell system).

Modifications of a nucleic acid sequence taught herein can, for example, be produced using the techniques taught in "Improved Methods for Site-directed Mutagenesis using NEBuilder® HiFi DNA Assembly Master Mix," New England BioLabs® Inc., Ipswich, Massachusetts, U.S.A., found at the URL https://www.neb.com/applications/cloning-and-synthetic-biology/dna-assembly-and-cloning/-/media/nebus/files/application-notes/improved-methods-for-site-directed-mutagenesis-using-nebuilder- hifi-dna-assembly-master-mix.pdf.. where ".." replaces a hyperlink. Other means of mutating or modifying nucleic acids are well known in the art.

As used herein, a "biomolecule" refers to a nucleic acid, a protein, a biopolymer, or any other biological molecule, or an organic molecule, or fragment or variant thereof, or any combination of such nucleic acids, proteins, biopolymers, other biological molecules, or organic molecules, or any combination thereof. For example, the biomolecule can, in some embodiments, be or include single-stranded DNA, double-stranded DNA or RNA. In addition, a "biomolecule" can include (1) an antibody, such as a monoclonal antibody, or another ligand specific molecule, and (2) other molecules that may have or could affect biologic and/or cellular activity.

In some embodiments, a protein included in a hydrophilic protein channel comprises a modification of SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In another embodiment, a protein included in a hydrophilic protein channel comprises a modification of SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In other embodiments, a protein variant comprises a modification of SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In another embodiment, a protein variant comprises a modification of SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In other embodiments, a nucleic acid molecule comprises a modification of a nucleic acid sequence of SEQ ID NO: 2, the modification of the nucleic acid sequence comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment, a nucleic acid molecule comprises a modification of a nucleic acid sequence of SEQ ID NO: 2, the modification of the nucleic acid sequence comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In other embodiments, a protein variant is encoded by a modification of a nucleic acid sequence of SEQ ID NO: 2, the modification of the nucleic acid sequence comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment, a protein variant is encoded by a modification of a nucleic acid sequence of SEQ ID NO: 2, the modification of the nucleic acid sequence comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In other embodiments, a vector comprises a modification of a nucleic acid sequence of SEQ ID NO: 2, the modification of the nucleic acid sequence comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment, a vector comprises a modification of a nucleic acid sequence of SEQ ID NO: 2, the modification of the nucleic acid sequence comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In other embodiments, a cell comprises a vector that comprises a modification of a nucleic acid sequence of SEQ ID NO: 2, the modification of the nucleic acid sequence comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment, a cell comprises a vector that comprises a modification of a nucleic acid sequence of SEQ ID NO: 2, the modification of the nucleic acid sequence comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

As used herein, a "nanopore" refers to a pore with a maximum pore dimension of less than about 20 nanometers, such as less than about 10 nanometers, or less than about 5 nanometers, or about 2 nanometers or less.

As used herein, a "solid-state matrix" refers to matrix made of a solid-state material, which is non-molecular solid material. For example, the solid-state matrix can be made of materials such as a silicon-containing nitride (e.g., silicon nitride), a silicon-containing carbide (e.g., silicon carbon), a silicon-containing oxide (e.g. silicon oxide), nickel, silicon, hafnium, or other solid-state materials.

As used herein, a "solid-state pore opening" refers to a pore opening formed in a solid-state matrix.

As used herein, a "hydrophilic protein" refers to a protein that includes residues that are soluble in water, at least over a substantial portion of a surface that is in contact with the water, such as an external surface of the hydrophilic protein.

As used herein, a "hydrophilic protein channel" refers to a protein structure comprising a channel opening therethrough, the structure being formed by one or more hydrophilic proteins.

As used herein a "stable insertion fit" of a hydrophilic protein channel within a solid-state pore opening refers to a substantially snug fit of the hydrophilic protein channel's external surface within the solid-state pore opening, such that the hydrophilic protein channel is stable for at least 2 hours, for example more than 3 hours, 4 hours, 5 hours or more, including substantially permanently stable, in the solid-state pore opening, while in the presence of a water solvent.

As used herein, a "protein nanopore channel" refers to a channel opening formed by and through a protein, the channel having a diameter less than about 20 nanometers, such as less than about 10 nanometers, or less than about 5 nanometers, or about 2 nanometers or less.

As used herein, a "wing loop residue" refers to an amino acid residue in a portion of a protein that is positioned in a substantially wing-shaped external portion of the protein. For example, on the portal protein of the *Thermus thermophilus* bacteriophage G20c, the wing loop residue can be one of the residues 36-41 or 46-54.

As used herein, a "tunnel loop residue" refers to an amino acid residue in a portion of a protein that forms an intruding loop within a channel that is formed by the protein, such as by multiple monomers of the protein or within a single monomer of the protein. For example, on the portal protein of the *Thermus thermophilus* bacteriophage G20c, the tunnel loop residue can be one of the residues 316-335.

As used herein, an "upper internal surface residue" refers to an amino acid residue in a portion of a protein that forms an internal surface of a tunnel portion of a channel that is formed by the protein, such as by multiple monomers of the protein or within a single monomer of the protein, and that is positioned "upwards" as determined by an accepted orientation of the protein, for example one that is in a "cap" portion of a cork-shaped protein that becomes inserted in a pore with its cap portion upwards and its "stem" portion embedded further into the pore. For example, on the portal protein of the *Thermus thermophilus* bacteriophage G20c, the upper internal surface residue can be one of the residues 381-400.

As used herein, a "lower internal surface residue" refers to an amino acid residue in a portion of a protein that forms an internal surface of a tunnel portion of a channel that is formed by the protein, such as by multiple monomers of the protein or within a single monomer of the protein, and that is positioned "downwards" or in a lower portion as determined by an accepted orientation of the protein, for example one that is in a "stem" portion of a cork-shaped protein that becomes inserted in a pore with its cap portion upwards and its "stem" portion embedded further into the pore. For example, on the portal protein of the *Thermus thermophilus* bacteriophage G20c, the lower internal surface residue can be one of the residues 273-303.

As used herein, an "external surface residue" refers to a residue on an outer surface of the protein, such as one that is exposed to a solid-state pore. For example, on the portal protein of the *Thermus thermophilus* bacteriophage G20c, the external surface residue can be residue 230, although is not limited to that residue and can include other external surface residues.

Tables and Sequences on Protein Versions and the Associated DNA

The below tables, Tables 1-7, provide properties of protein versions taught herein, and the associated DNA. In the left column of each table, the protein version is provided, corresponding to the same protein version listed in the other tables.

TABLE 1

Protein Version with Mutant Grouping and Amino Acid Range

| Protein Version | Mutant Grouping | Amino Acid Range |
|---|---|---|
| WT Full Length | None | 1-448 |
| WT 1-438 C-term | C-terminal Extension | 1-438 |
| WT 1-438 3C prot | WT | 1-438 |
| WT Nanopore | WT | 25-438 |
| L230E | External Surface | 25-438 |
| 49C | Wing Loops | 25-438 |
| 40E | Wing Loops | 25-438 |
| G | Tunnel Loops | 25-438 |
| M | Tunnel Loops | 25-438 |
| K | Tunnel Loops | 25-438 |
| CGG | Wing Loops/Tunnel Loops | 25-438 |
| Loop2GG | Tunnel Loops | 25-438 |
| 49CLoop3G | Tunnel Loops | 25-438 |
| CD/N | Wing Loops/Lower Tunnel | 25-438 |
| SIN1 | Wing Loop Insertion | 25-438 |
| SIN2 | Wing Loop Insertion | 25-438 |
| SIN3 | N-Terminal Extension | 25-438 |
| SIN4 | Wing Loop Insertion | 25-438 |
| 400C | Upper Tunnel/Crown | 1-438 |

TABLE 2

Protein Version with Expression Construct and Affinity Purification Tag

| Protein Version | Expression Construct | Affinity Purification Tag |
|---|---|---|
| WT Full Length | None | None |
| WT 1-438 C-term | pET22b | C-terminal HexaHistidine |
| WT 1-438 3C prot | pYSBL_Lic+ | N-terminal HexaHistidine 3CProtease |
| WT Nanopore | pYSBL_Lic+ | N-terminal HexaHistidine 3CProtease |
| L230E | pYSBL_Lic+ | N-terminal HexaHistidine 3CProtease |
| 49C | pYSBL_Lic+ | N-terminal HexaHistidine 3CProtease |
| 40E | pYSBL_Lic+ | N-terminal HexaHistidine 3CProtease |
| G | pYSBL_Lic+ | N-terminal HexaHistidine 3CProtease |
| M | pYSBL_Lic+ | N-terminal HexaHistidine 3CProtease |
| K | pYSBL_Lic+ | N-terminal HexaHistidine 3CProtease |
| CGG | pYSBL_Lic+ | N-terminal HexaHistidine 3CProtease |
| Loop2GG | pYSBL_Lic+ | N-terminal HexaHistidine 3CProtease |
| 49CLoop3G | pYSBL_Lic+ | N-terminal HexaHistidine 3CProtease |
| CD/N | pYSBL_Lic+ | N-terminal HexaHistidine 3CProtease |
| SIN1 | pYSBL_Lic+ | N-terminal HexaHistidine 3CProtease |
| SIN2 | pYSBL_Lic+ | N-terminal HexaHistidine 3CProtease |
| SIN3 | pYSBL_Lic+ | N-terminal HexaHistidine 3CProtease |
| SIN4 | pYSBL_Lic+ | N-terminal HexaHistidine 3CProtease |
| 400C | pYSBL_Lic+ | C-terminal HexaHistidine |

In the below sequences, the affinity tags in the protein sequence are included for those constructs where they are not removed post purification, for example, SEQ ID NO: 3 and SEQ ID NO: 37. However, since histidine tags can perturb nucleic acid interaction with proteins, particularly a circular ring of twelve such tags as is formed in a dodecameric assembly of proteins, the final purified protein (with, for example, a hexahistadine tag) can be cleaved with 3C protease to remove the hexahistidine tag, leaving GPA as the remaining part of the tag at the N-terminus of the protein. Hence, GPA is the sequence for the N-terminal 3 amino acids for the following sequence listings, which reflect those proteins after having been cleaved: SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33 and SEQ ID NO: 35. However, the full length tag sequence present prior to cleavage is included in the DNA sequence of the full open reading frame used to express the protein in *E. coli*. For the protein version WT Nanopore, below, the full length amino acid sequence prior to cleavage is given in SEQ ID NO: 39. The cleaved amino acid sequence of this protein is given in SEQ ID NO: 7.

TABLE 3

Protein Version with Amino Acid Mutation
Residue position number in full length wild type (WT) amino acid sequence.

| Protein Version | Amino Acid Mutation |
|---|---|
| WT Full Length | N/A |
| WT 1-438 C-term | N/A (cleaving off residues 439 through 448) |
| WT 1-438 3C prot | N/A (cleaving off residues 439 through 448) |
| WT Nanopore | N/A (cleaving off residues 1 through 24 and 439 through 448) |
| L230E | L230E |
| 49C | L49C |
| 40E | V40E |
| G | V325G |
| M | V325M |
| K | I328K |
| CGG | L49C/V325G/I328G |
| Loop2GG | V325G/Δ326/A327G/I328G |
| 49CLoop3G | L49C/Δ281-296G |
| CD/N | L49C/D281N/D286N/D289N/D296N/V352A |
| SIN1 | Insert E48_GTPGSRG_L49/D281N/D286N/ D289N/D296N |
| SIN2 | Insert E48_GRKLPDAG_L49/D281N/D286N/ D289N/D296N |
| SIN3 | Insert SSKKSGSYSGSKGS_K25/L49C/D281N/ D286N/D289N/D296N |
| SIN4 | Insert E48_GYRPGFYFR_L49/D281N/D286N/ D289N/D296N |
| 400C | D400C |

TABLE 4

Protein Version with DNA Mutation
Nucleotide position number in the full length wild type DNA sequence of the open reading frame coding for the protein.

| Protein Version | DNA Mutation |
|---|---|
| WT Full Length | N/A |
| WT 1-438 C-term | N/A |
| WT 1-438 3C prot | N/A |
| WT Nanopore | N/A |
| L230E | GAG_681-683_CTC |
| 49C | CTA_139-141_TGT |
| *40E | T_119_A |
| G | GTA_973-975_GGA |
| *M | GTA_973-975_ATG |
| K | TA_983-984_AG |
| CGG | CTA_139-141_TGT/GTA_973-975_ GGA/AT_A_982-984_GGA |
| Loop2GG | GTACAGGCGATA_973-984_GGAGGCGGT |
| 49CLoop3G | CTA_139-141_TGT/AAC_ATGGGGT_AC_ AGGCGAT_AAAC_964-987_GGT |
| CD/N | CTA_139-141_TGT/G_841_A/G_856_ A/G_865_A/G_886_A/T_1055_C |
| SIN1 | Insert GAG_143-145_GGTACGCCAGG TTCTCGCGGC_146-148_CTA |
| SIN2 | Insert GAG_143_-145_GGTCGTAAAC 1TGCCGGATGC_AGGC_I46-48_CTA |
| SIN3 | Insert AGCAGTAAGAAAAGTGGAAGCTA TAGCGGCAGCAAAGGCAGC73- 75_AAG/CTA_139-141_TGT |
| SIN4 | Insert_GAG_143-145_GGATATCGCCC GGGCTTTTATTTTCGC146-148_CTA |
| *400C | GA_1198-1199_TG |

Sequences marked with an "*" in Table 4, above, were sequenced in one direction (across the new introduced mutation) and the complete sequence was assembled from the data available from the template used to produce the new mutant construct. All other sequences assembled from original DNA sequencing data.

TABLE 5

Protein Version with Amino Acid Sequence and DNA Sequence

| Protein Version | Amino Acid Sequence | DNA Sequence |
|---|---|---|
| WT Full Length | SEQ ID NO: 1 | SEQ ID NO: 2 |
| WT 1-438 C-term | SEQ ID NO: 3 | SEQ ID NO: 4 |
| WT 1-438 3C prot | SEQ ID NO: 5 | SEQ ID NO: 6 |
| WT Nanopore | SEQ ID NO: 7 | SEQ ID NO: 8 |
| L230E | SEQ ID NO: 9 | SEQ ID NO: 10 |
| 49C | SEQ ID NO: 11 | SEQ ID NO: 12 |
| 40E | SEQ ID NO: 13 | SEQ ID NO: 14 |
| G | SEQ ID NO: 15 | SEQ ID NO: 16 |
| M | SEQ ID NO: 17 | SEQ ID NO: 18 |
| K | SEQ ID NO: 19 | SEQ ID NO: 20 |
| CGG | SEQ ID NO: 21 | SEQ ID NO: 22 |
| Loop2GG | SEQ ID NO: 23 | SEQ ID NO: 24 |
| 49CLoop3G | SEQ ID NO: 25 | SEQ ID NO: 26 |
| CD/N | SEQ ID NO: 27 | SEQ ID NO: 28 |
| SIN1 | SEQ ID NO: 29 | SEQ ID NO: 30 |
| SIN2 | SEQ ID NO: 31 | SEQ ID NO: 32 |

TABLE 5-continued

| Protein Version with Amino Acid Sequence and DNA Sequence | | |
|---|---|---|
| Protein Version | Amino Acid Sequence | DNA Sequence |
| SIN3 | SEQ ID NO: 33 | SEQ ID NO: 34 |
| SIN4 | SEQ ID NO: 35 | SEQ ID NO: 36 |
| 400C | SEQ ID NO: 37 | SEQ ID NO: 38 |

TABLE 6

| Example-Protein Version with Nanopore Insertion Performed | |
|---|---|
| Protein Version | Nanopore Insertion Performed |
| WT 1-438 C-term | Thick Hafnium 6-8 nm |
| WT 1-438 3C prot | Thick SiN 6-8 nm |
| WT Nanopore | Thick SiN 6-8 nm |
| 49C | Planar Lipid Bilayer |
| CGG | Thick SiN 6-8 nm/planar lipid bilayer |
| CD/N | Thick SiN 6-8 nm |

TABLE 7

| Example-Protein Version with Nanopore Translocation Performed | |
|---|---|
| Protein Version | Nanopore Translocation Performed |
| 49C | Cyclodextrin |
| CGG | Cyclodextrin |
| CD/N | dsDNA/ssDNA/peptide |

In the below sequences, a letter "X" signifies "any amino acid," and a letter "n" signifies any nucleotide (n=A, T, C or G).

SEQ ID NO: 1

```
MAKRGRKPKELVPGPGSIDPSDVPKLEGASVPVMS

TSYDVVVDREFDELLQGKDGLLVYHKMLSDGTVKN

ALNYIFGRIRSAKWYVEPASTDPEDIAIAAFIHAQ

LGIDDASVGKYPFGRLFAIYENAYIYGMAAGEIVL

TLGADGKLILDKIVPIHPFNIDEVLYDEEGGPKAL

KLSGEVKGGSQFVSGLEIPIWKTVVFLHNDDGSFT

GQSALRAAVPHWLAKRALILLINHGLERFMIGVPT

LTIPKSVRQGTKQWEAAKEIVKNFVQKPRHGIILP

DDWKFDTVDLKSAMPDAIPYLTYHDAGIARALGID

FNTVQLNMGVQAINIGEFVSLTQQTIISLQREFAS

AVNLYLIPKLVLPNWPSATRFPRLTFEMEERNDFS

AAANLMGMLINAVKDSEDIPTELKALIDALPSKMR

RALGVVDEVREAVRQPADSRYLYTRRRR
```

SEQ ID NO: 2

```
ATGGCTAAGCGAGGACGTAAACCCAAAGAGCTGGT

CCCCGGACCTGGCTCCATTGACCCATCTGACGTTC

CCAAGCTCGAGGGCGCCTCCGTGCCGGTGATGTCC

ACCAGTTACGACGTGGTGGTGGACCGGGAGTTTGA
```

-continued

```
CGAGCTACTGCAGGGCAAGGACGGCTTGCTCGTCT

ACCACAAGATGCTCTCGGACGGCACGGTTAAGAAC

GCCCTCAACTACATCTTCGGACGCATCCGCTCGGC

GAAGTGGTACGTAGAGCCCGCCTCTACCGACCCGG

AAGACATCGCCATCGCCGCCTTCATCCACGCCCAG

TTAGGCATAGACGACGCTTCGGTGGGCAAGTATCC

CTTTGGCCGCCTTTTCGCCATCTACGAAAACGCCT

ACATATACGGCATGGCCGCCGGGGAAATCGTACTA

ACCCTTGGCGCGGACGGCAAGCTCATCCTTGACAA

AATCGTCCCTATCCACCCTTTCAACATTGACGAGG

TGCTTTACGACGAGGAAGGCGGTCCAAAGGCGCTA

AAGCTAAGCGGAGAGGTGAAGGGCGGAAGCCAGTT

TGTGAGCGGGTTGGAGATTCCTATATGGAAGACCG

TGGTCTTCCTGCACAACGACGACGGCTCCTTCACC

GGACAGAGCGCCCTCAGAGCCGCCGTGCCGCATTG

GCTAGCCAAACGAGCCCTCATTCTCCTCATCAACC

ACGGGTTGGAGCGCTTCATGATTGGCGTGCCCACC

CTCACCATCCCCAAGAGCGTGCGTCAGGGAACCAA

GCAATGGGAGGCCGCCAAGGAAATCGTCAAGAACT

TTGTTCAAAAACCACGGCATGGTATAATACTGCCT

GACGACTGGAAGTTTGACACGGTAGACCTGAAGTC

GGCCATGCCCGACGCCATTCCCTACCTGACCTACC

ACGACGCGGGCATCGCTAGGGCGCTTGGCATAGAC

TTCAACACCGTTCAACTAAACATGGGGGTACAGGC

GATAAACATCGGCGAGTTCGTAAGCCTGACCCAGC

AGACCATCATTTCGCTCCAGCGGGAGTTCGCTAGC

GCGGTCAACCTCTACCTCATCCCCAAGCTAGTGCT

TCCCAACTGGCCGAGCGCTACTCGCTTTCCTAGGC

TCACCTTTGAGATGGAGGAGCGCAACGACTTCTCC

GCCGCGGCCAACCTTATGGGCATGCTCATCAACGC

GGTTAAGGACTCCGAAGACATTCCCACCGAGCTCA

AGGCGCTAATAGACGCTCTGCCTAGCAAGATGCGC

CGGGCGCTTGGCGTGGTGGACGAGGTGAGGGAAGC

GGTACGCCAACCCGCCGATTCCCGCTACCTGTACA

CGCGAAGGAGGAGGTAG
```

SEQ ID NO: 3

```
MAKRGRKPKELVPGPGSIDPSDVPKLEGASVPVMS

TSYDVVVDREFDELLQGKDGLLVYHKMLSDGTVKN

ALNYIFGRIRSAKWYVEPASTDPEDIAIAAFIHAQ

LGIDDASVGKYPFGRLFAIYENAYIYGMAAGEIVL

TLGADGKLILDKIVPIHPFNIDEVLYDEEGGPKAL
```

-continued

KLSGEVKGGSQFVSGLEIPIWKTVVFLHNDDGSFT
GQSALRAAVPHWLAKRALILLINHGLERFMIGVPT
LTIPKSVRQGTKQWEAAKEIVKNFVQKPRHGIILP
DDWKFDTVDLKSAMPDAIPYLTYHDAGIARALGID
FNTVQLNMGVQAINIGEFVSLTQQTIISLQREFAS
AVNLYLIPKLVLPNWPSATRFPRLTFEMEERNDFS
AAANLMGMLINAVKDSEDIPTELKALIDALPSKMR
RALGVVDEVREAVRQPADLEHHHHHH

SEQ ID NO: 4
ATGGCTAAGCGAGGACGTAAACCCAAAGAGCTGGT
CCCCGGACCTGGCTCCATTGACCCATCTGACGTTC
CCAAGCTCGAGGGCGCCTCCGTGCCGGTGATGTCC
ACCAGTTACGACGTGGTGGTGGACCGGGAGTTTGA
CGAGCTACTGCAGGGCAAGGACGGCTTGCTCGTCT
ACCACAAGATGCTCTCGGACGGCACGGTTAAGAAC
GCCCTCAACTACATCTTCGGACGCATCCGCTCGGC
GAAGTGGTACGTAGAGCCCGCCTCTACCGACCCGG
AAGACATCGCCATCGCCGCCTTCATCCACGCCCAG
TTAGGCATAGACGACGCTTCGGTGGGCAAGTATCC
CTTTGGCCGCCTTTTCGCCATCTACGAAAACGCCT
ACATATACGGCATGGCCGCCGGGGAAATCGTACTA
ACCCTTGGCGCGGACGGCAAGCTCATCCTTGACAA
AATCGTCCCTATCCACCCTTTCAACATTGACGAGG
TGCTTTACGACGAGGAAGGCGGTCCAAAGGCGCTA
AAGCTAAGCGGAGAGGTGAAGGGCGGAAGCCAGTT
TGTGAGCGGGTTGGAGATTCCTATATGGAAGACCG
TGGTCTTCCTGCACAACGACGACGGCTCCTTCACC
GGACAGAGCGCCCTCAGAGCCGCCGTGCCGCATTG
GCTAGCCAAACGAGCCCTCATTCTCCTCATCAACC
ACGGGTTGGAGCGCTTCATGATTGGCGTGCCCACC
CTCACCATCCCCAAGAGCGTGCGTCAGGGAACCAA
GCAATGGGAGGCCGCCAAGGAAATCGTCAAGAACT
TTGTTCAAAAACCACGGCATGGTATAATACTGCCT
GACGACTGGAAGTTTGACACGGTAGACCTGAAGTC
GGCCATGCCCGACGCCATTCCCTACCTGACCTACC
ACGACGCGGGCATCGCTAGGGCGCTTGGCATAGAC
TTCAACACCGTTCAACTAAACATGGGGGTACAGGC
GATAAACATCGGCGAGTTCGTAAGCCTGACCCAGC
AGACCATCATTTCGCTCCAGCGGGAGTTCGCTAGC
GCGGTCAACCTCTACCTCATCCCCAAGCTAGTGCT
TCCCAACTGGCCGAGCGCTACTCGCTTTCCTAGGC

-continued

TCACCTTTGAGATGGAGGAGCGCAACGACTTCTCC
GCCGCGGCCAACCTTATGGGCATGCTCATCAACGC
GGTTAAGGACTCCGAAGACATTCCCACCGAGCTCA
AGGCGCTAATAGACGCTCTGCCTAGCAAGATGCGC
CGGGCGCTTGGCGTGGTGGACGAGGTGAGGGAAGC
GGTACGCCAACCCGCCGATctcgagcaccaccacc
accaccacTAG SEQ ID NO: 5
GPAMAKRGRKPKELVPGPGSIDPSDVPKLEGASVP
VMSTSYDVVVDREFDELLQGKDGLLVYHKMLSDGT
VKNALNYIFGRIRSAKWYVEPASTDPEDIAIAAFI
HAQLGIDDASVGKYPFGRLFAIYENAYIYGMAAGE
IVLTLGADGKLILDKIVPIHPFNIDEVLYDEEGGP
KALKLSGEVKGGSQFVSGLEIPIWKTVVFLHNDDG
SFTGQSALRAAVPHWLAKRALILLINHGLERFMIG
VPTLTIPKSVRQGTKQWEAAKEIVKNFVQKPRHGI
ILPDDWKFDTVDLKSAMPDAIPYLTYHDAGIARAL
GIDFNTVQLNMGVQAINIGEFVSLTQQTIISLQRE
FASAVNLYLIPKLVLPNWPSATRFPRLTFEMEERN
DFSAAANLMGMLINAVKDSEDIPTELKALIDALPS
KMRRALGVVDEVREAVRQPAD SEQ ID NO: 6
ATGGGCAGCAGCCATCATcATCATCATCACAGCAG
CGGCCTGGAAGTTCTGTTCCAGGGACCAGCAATGG
CTAAGCGAGGACGTAAACCCAAAGAGCTGGTCCCC
GGACCTGGCTCCATTGACCCATCTGACGTTCCCAA
GCTCGAGGGCGCCTCCGTGCCGGTGATGTCCACCA
GTTACGACGTGGTGGTGGACCGGGAGTTTGACGAG
CTACTGCAGGGCAAGGACGGCTTGCTCGTCTACCA
CAAGATGCTCTCGGACGGCACGGTTAAGAACGCCC
TCAACTACATCTTCGGACGCATCCGCTCGGCGAAG
TGGTACGTAGAGCCCGCCTCTACCGACCCGGAAGA
CATCGCCATCGCCGCCTTCATCCACGCCCAGTTAG
GCATAGACGACGCTTCGGTGGGCAAGTATCCCTTT
GGCCGCCTTTTCGCCATCTACGAAAACGCCTACAT
ATACGGCATGGCCGCCGGGGAAATCGTACTAACCC
TTGGCGCGGACGGCAAGCTCATCCTTGACAAAATC
GTCCCTATCCACCCTTTCAACATTGACGAGGTGCT
TTACGACGAGGAAGGCGGTCCAAAGGCGCTAAAGC
TAAGCGGAGAGGTGAAGGGCGGAAGCCAGTTTGTG
AGCGGGTTGGAGATTCCTATATGGAAGACCGTGGT
CTTCCTGCACAACGACGACGGCTCCTTCACCGGAC -continued AGAGCGCCCTCAGAGCCGCCGTGCCGCATTGGCTA
GCCAAACGAGCCCTCATTCTCCTCATCAACCACGG
GTTGGAGCGCTTCATGATTGGCGTGCCCACCCTCA
CCATCCCCAAGAGCGTGCGTCAGGGAACCAAGCAA
TGGGAGGCCGCCAAGGAAATCGTCAAGAACTTTGT
TCAAAAACCACGGCATGGTATAATACTGCCTGACG
ACTGGAAGTTTGACACGGTAGACCTGAAGTCGGCC
ATGCCCGACGCCATTCCCTACCTGACCTACCACGA
CGCGGGCATCGCTAGGGCGCTTGGCATAGACTTCA
ACACCGTTCAACTAAACATGGGGGTACAGGCGATA
AACATCGGCGAGTTCGTAAGCCTGACCCAGCAGAC
CATCATTTCGCTCCAGCGGGAGTTCGCTAGCGCGG
TCAACCTCTACCTCATCCCCAAGCTAGTGCTTCCC
AACTGGCCGAGCGCTACTCGCTTTCCTAGGCTCAC
CTTTGAGATGGAGGAGCGCAACGACTTCTCCGCCG
CGGCCAACCTTATGGGCATGCTCATCAACGCGGTT
AAGGACTCCGAAGACATTCCCACCGAGCTCAAGGC
GCTAATAGACGCTCTGCCTAGCAAGATGCGCCGGG
CGCTTGGCGTGGTGGACGAGGTGAGGGAAGCGGTA
CGCCAACCCGCCGATTAA

SEQ ID NO: 7

GPAKLEGASVPVMSTSYDVVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPDDWKFDTVDLKSAMPDAIPYL
TYHDAGIARALGIDFNTVQLNMGVQAINIGEFVSL
TQQTIISLQREFASAVNLYLIPKLVLPNWPSATRF
PRLTFEMEERNDFSAAANLMGMLINAVKDSEDIPT
ELKALIDALPSKMRRALGVVDEVREAVRQPAD

SEQ ID NO: 8

ATGGGCAGCAGCCATCATCcATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGCT
ACTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA

-continued

TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCGGGGAAATCGTACTAACCCTT
GGCGCGGACGGCAAGCTCATCCTTGACAAAATCGT
CCCTATCCACCCTTTCAACATTGACGAGGTGCTTT
ACGACGAGGaAGGCGGTCCAAAGGCGCTAAAGCTA
AGCGGAGAGGTGAAGGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAATCGTCAAGAACTTTGTTC
AAAAACCacGGCATGGTATAATACTGCCTGACGAC
TGGAAGTTTGACACGGTAGACCTGAAGTCGGCCAT
GCCCGACGCCATTCCCTACCTGACCTACCACGACG
CGGGCATCGCTAGGGCGCTTGGCATAGACTTCAAC
ACCGTTCAACTAAACATGGGGGTACAGGCGATAAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACTTCtcCGCCGCG
GCCAACCTTATGGGCATGCTCATCaACGCGGTTAA
GGACTCCGAAGACATTCCCacCGAGCTcaaGGCGC
TAATAGACGCTCTGCCTAGCaAGATGCGCCGGGCG
CTTGGCGTGGTGGACGAGGTGAGGGAAGCGGTACG
CCaACCCGcCgATTAA

SEQ ID NO: 9

GPAKLEGASVPVMSTSYDVVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALIEL
INHGLERFMIGVPTLTIPKSVRQGTKQWEAAKEIV
KNFVQKPRHGIILPDDWKFDTVDLKSAMPDAIPYL
TYHDAGIARALGIDFNTVQLNMGVQAINIGEFVSL
TQQTIISLQREFASAVNLYLIPKLVLPNWPSATRF

-continued

PRLTFEMEERNDFSAAANLMGMLINAVKDSEDIPT

ELKALIDALPSKMRRALGVVDEVREAVRQPAD

SEQ ID NO: 10

ATGGGCAGCAGCCATcatCAtCATCATCACAGCAG

CGGCCTGGAAGTTCTGTTCCAGGgaCCAGCAAAGC

TCGAGGGCGCCTCCgtGCCGgtgATGTCCACCAGT

TACGACGTGgtGGTGGACCGGGAGTTTGACGAGCT

ACTGCAGGGCAAGGACGGCTTGCTCGTCTACCACA

AGATGCTCTCGGACGGCACGGTTAAGAACGCCCTC

AACTACATCTTCGGACGCATCCGCTCGGCGAAGTG

GTACGTAGAGCCCGCCTCTACCGACCCGGAAGACA

TCGCCATCGCCGCCTTCATCCACGCCCAGTTAGGC

ATAGACGACGCTTCGGTGGGCAAGTATCCCTTTGG

CCGCCTTTTCGCCATCTACGAAAACGCCTACATAT

ACGGCATGGCCGCCGGGGAAATCGTACTAACCCTT

GGCGCGGACGGCAAGCTCATCCTTGACAAAATCGT

CCCTATCCACCCTTTCAACATTGACGAGGTGCTTT

ACGACGAGGAAGGCGGTCCAAAGGCGCTAAAGCTA

AGCGGAGAGGTGAAGGGCGGAAGCCAGTTTGTGAG

CGGGTTGGAGATTCCTATATGGAAGACCGTGGTCT

TCCTGCACAACGACGACGGCTCCTTCACCGGACAG

AGCGCCCTCAGAGCCGCCGTGCCGCATTGGCTAGC

CAAACGAGCCCTCATTGAGCTCATCAACCACGGGT

TGGAGCGCTTCATGATTGGCGTGCCCACCCTCACC

ATCCCCAAGAGCGTGCGTCAGGGAACCAAGCAATG

GGAGGCCGCCAAGGAAATCGTCAAGAACTTTGTTC

AAAAACCACGGCATGGTATAATACTGCCTGACGAC

TGGAAGTTTGACACGGTAGACCTGAAGTCGGCCAT

GCCCGACGCCATTCCCTACCTGACCTACCACGACG

CGGGCATCGCTAGGGCGCTTGGCATAGACTTCAAC

ACCGTTCAACTAAACATGGGGgTaCAGGCGATAAA

CATCGGCGAGTTCGTAAGCCTGACCcAGCAGACCA

TCATTtCgCTCCAGCGGGAGTtcGCTAGCGCGGTC

AACCTCTACCTCATCCCcAAGCTAGTgcTtCCcAA

CTGGCCGAGCGCTACTCGCTTTCCTAGGCTCACCT

TTGAGATGGAGGAGCGCAACGACTTCtcCGCCGCG

GCCAACCTTATGGGCATGCTCATCaACGCGGTTAA

GGACTCCGAAGACATTCCCacCGAGCTcaaGGCGC

TAATAGACGCTCTGCCTAGCaAGATGCGCCGGGCG

-continued

CTTGGCGTGGTGGACGAGGTGAGGGAAGCGGTACG

CCaACCCGcCgATTAA

SEQ ID NO: 11

GPAKLEGASVPVMSTSYDVVVDREFDECLQGKDGL

LVYHKMLSDGTVKNALNYIFGRIRSAKWYVEPAST

DPEDIAIAAFIHAQLGIDDASVGKYPFGRLFAIYE

NAYIYGMAAGEIVLTLGADGKLILDKIVPIHPFNI

DEVLYDEEGGPKALKLSGEVKGGSQFVSGLEIPIW

KTVVFLHNDDGSFTGQSALRAAVPHWLAKRALILL

INHGLERFMIGVPTLTIPKSVRQGTKQWEAAKEIV

KNFVQXPRHGIILPDDWKFDTVDLKSAMPDAIPYL

TYHDAGIARALGIDFNTVQLNMGVQAINIGEFVSL

TQQTIISLQREFASAVNLYLIPKLVLPNWPSATRF

PRLTFEMEERNDFSAAANLMGMLINAVKDSEDIPT

ELKALIDALPSKMRRALGVVDEVREAVRQPAD

SEQ ID NO: 12

ATGGGCAGCAGCCATCATCATCATCATCACAGCAG

CGGCCtGgAAGTTCTGTTCCAGGGACCAGCAAAGC

TCGAGGGCGCCTCCgtGCCGGTGATGTCCACCAGT tACGACGTGGTGGTGGACCGGGAGTTTGACGAGTG

TCTGCAGGGCAAGGACGGCTTGCTCGTCTACCACA

AGATGCTCTCGGACGGCACGGTTAAGAACGCCCTC

AACTACATCTTCGGACGCATCCGCTCGGCGAAGTG

GTACGTAGAGCCCGCCTCTACCGACCCGGAAGACA

TCGCCATCGCCGCCTTCATCCACGCCCAGTTAGGC

ATAGACGACGCTTCGGTGGGCAAGTATCCCTTTGG

CCGCCTTTTCGCCATCTACGAAAACGCCTACATAT

ACGGCATGGCCGCCGGGGAAATCGTACTAACCCTT

GGCGCGGACGGCAAGCTCATCCTTGACAAAATCGT

CCCTATCCACCCTTTCAACATTGACGAGGTGCTTT

ACGACGAGGAAGGCGGTCCAAAGGCGCTAAAGCTA

AGCGGAGAGGTGAAGGGCGGAAGCCAGTTTGTGAG

CGGGTTGGAGATTCCTATATGGAAGACCGTGGTCT

TCCTGCACAACGACGACGGCTCCTTCACCGGACAG

AGCGCCCTCAGAGCCGCCGTGCCGCATTGGCTAGC

CAAACGAGCCCTCATTCTCCTCATCAACCACGGGT

TGGAGCGCTTCATGATTGGCGTGCCCACCCTCACC

ATCCCCAAGAGCGTGCGTCAGGGAACCAAGCAATG

GGAGGCCGCCAAGGAaaTCGTCAAGAACTTtGTTC

AAAAnCCACGGCATGGTATAATACTGCCTGACGAC

TGGAAGTTTGACACGGTAGACCTgAaGTCGGCCAT

GCCCGACGCCATTCCCTACCTGACCTACCACGACG

-continued

CGGGCATCGCTAGGGCGCTtGGCATAGACTTcaaC
ACCgTtCAACTAAACATGGGGGTACAGGCGATAAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACTTCtcCGCCGCG
GCCAACCTTATGGGCATGCTCATCaACGCGGTTAA
GGACTCCGAAGACATTCCCacCGAGCTcaaGGCGC
TAATAGACGCTCTGCCTAGCaAGATGCGCCGGGCG
CTTGGCGTGGTGGACGAGGTGAGGGAAGCGGTACG
CCaACCCGcCgATTAA

SEQ ID NO: 13

GPAKLEGASVPVMSTSYDEVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQXPRHGIILPDDWKFDTVDLKSAMPDAIPYL
TYHDAGIARALGIDFNTVQLNMGVQAINIGEFVSL
TQQTIISLQREFASAVNLYLIPKLVLPNWPSATRF
PRLTFEMEERNDFSAAANLMGMLINAVKDSEDIPT
ELKALIDALPSKMRRALGVVDEVREAVRQPAD

SEQ ID NO: 14

ATGGGCAGCAGCCATCATCATCATCATCACAGCAG
CGGCCtGgAAGTTCTGTTCCAGGGACCAGCAAAGC
TCGAGGGCGCCTCCgtGCCGGTGATGTCCACCAGT
tACGACGAGGTGGTGGACCGGGAGTTTGACGAGCT
ACTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCGGGGAAATCGTACTAACCCTT
GGCGCGGACGGCAAGCTCATCCTTGACAAAATCGT
CCCTATCCACCCTTTCAACATTGACGAGGTGCTTT
ACGACGAGGAAGGCGGTCCAAAGGCGCTAAAGCTA
AGCGGAGAGGTGAAGGGCGGAAGCCAGTTTGTGAG

-continued

CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAaTCGTCAAGAACTTTtGTTC
AAAAnCCACGGCATGGTATAATACTGCCTGACGAC
TGGAAGTTTGACACGGTAGACCTgAaGTCGGCCAT
GCCCGACGCCATTCCCTACCTGACCTACCACGACG
CGGGCATCGCTAGGGCGCTtGGCATAGACTTcaaC
ACCgTtCAACTAAACATGGGGGTACAGGCGATAAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACTTCtcCGCCGCG
GCCAACCTTATGGGCATGCTCATCaACGCGGTTAA
GGACTCCGAAGACATTCCCacCGAGCTcaaGGCGC
TAATAGACGCTCTGCCTAGCaAGATGCGCCGGGCG
CTTGGCGTGGTGGACGAGGTGAGGGAAGCGGTACG
CCaACCCGcCgATTAA

SEQ ID NO: 15

GPAKLEGASVPVMSTSYDVVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPDDWKFDTVDLKSAMPDAIPYL
TYHDAGIARALGIDFNTVQLNMGGQAINIGEFVSL
TQQTIISLQREFASAVNLYLIPKLVLPNWPSATRF
PRLTFEMEERNDFSAAANLMGMLINAVKDSEDIPT
ELKALIDALPSKMRRALGVVDEVREAVRQPAD

SEQ ID NO: 16

ATGGGCAGCAGCCATCATcATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGCT
ACTGCAGGGCAAGGACGGCTTGCTCGTCTACCACA
AGATGCTCTCGGACGGCACGGTTAAGAACGCCCTC

-continued

AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCgggGAAATCGTACTAAcCCtt
GGCGCGGACGGCAAGCTCATCCTTGACaaaATCGT
CCCTAtcCACCCttTCAACATTGACGAGGTGCTTT
ACGACGAGGAAGGCGGTCCAAAGGCGCTAAAGCTA
AGCGGAGAGGTGAAgGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAATCGTCAAGAACTTTGTTC
AAAAACCACGGCATGGTATAATACTGCCTGACGAC
TGGAAGTTTGACACGGTAGACCTGAAGTCGGCCAT
GCCCGACGCCATTCCCTACCTGACCTACCACGACG
CGGGCATCGCTAGGGCGCTTGGCATAGACTTCAAC
ACCGTTCAACTAAACATGGGGGACAGGCGATAAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACtTctcCGCCGCG
GCCAACCTTATGGGCATGCTCATCaACGCGGTTAA
GGACTCCGAAGACATTCCCACCGAGCTcaAGGCGC
TAATAGACGCTCTGCCTAGCAAGATGCGCCGGGCG
CTTGGCGTGGTGGacgAGGTGAGGGAAGCGGTAcG
CCaACCCGCCGATTaa

SEQ ID NO: 17

GPAKLEGASVPVMSTSYDVVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPDDWKFDTVDLKSAMPDAIPYL
TYHDAGIARALGIDFNTVQLNMGMQAINIGEFVSL
TQQTIISLQREFASAVNLYLIPKLVLPNWPSATRF
PRLTFEMEERNDFSAAANLMGMLINAVKDSEDIPT
ELKALIDALPSKMRRALGVVDEVREAVRQPAD

SEQ ID NO: 18

ATGGGCAGCAGCCATCATcATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGCT
ACTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCgggGAAATCGTACTAAcCCtt
GGCGCGGACGGCAAGCTCATCCTTGACaaaATCGT
CCCTAtcCACCCttTCAACATTGACGAGGTGCTTT
ACGACGAGGAAGGCGGTCCAAAGGCGCTAAAGCTA
AGCGGAGAGGTGAAgGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAATCGTCAAGAACTTTGTTC
AAAAACCACGGCATGGTATAATACTGCCTGACGAC
TGGAAGTTTGACACGGTAGACCTGAAGTCGGCCAT
GCCCGACGCCATTCCCTACCTGACCTACCACGACG
CGGGCATCGCTAGGGCGCTTGGCATAGACTTCAAC
ACCGTTCAACTAAACATGGGGATGCAGGCGATAAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACtTctcCGCCGCG
GCCAACCTTATGGGCATGCTCATCaACGCGGTTAA
GGACTCCGAAGACATTCCCACCGAGCTcaAGGCGC
TAATAGACGCTCTGCCTAGCAAGATGCGCCGGGCG -continued CTTGGCGTGGTGGacgAGGTGAGGGAAGCGGTAcG CCaACCCGCCGATTaa

SEQ ID NO: 19

GPAKLEGASVPVMSTSYDVVVDREFDELLQGKDGL

LVYHKMLSDGTVKNALNYIFGRIRSAKWYVEPAST

DPEDIAIAAFIHAQLGIDDASVGKYPFGRLFAIYE

NAYIYGMAAGEIVLTLGADGKLILDKIVPIHPFNI

DEVLYDEEGGPKALKLSGEVKGGSQFVSGLEIPIW

KTVVFLHNDDGSFTGQSALRAAVPHWLAKRALILL

INHGLERFMIGVPTLTIPKSVRQGTKQWEAAKEIV

KNFVQKPRHGIILPDDWKFDTVDLKSAMPDAIPYL

TYHDAGIARALGIDFNTVQLNMGVQAKNIGEFVSL

TQQTIISLQREFASAVNLYLIPKLVLPNWPSATRF

PRLTFEMEERNDFSAAANLMGMLINAVKDSEDIPT

ELKALIDALPSKMRRALGVVDEVREAVRQPAD

SEQ ID NO: 20

ATGGGCAGCAGCCATCATCATCATCATCACAGCAG

CGGCCTGGAAGTTCTGTTCCAGGGACCAGCAAAGC

TCGAGGGCGCCTCCGTGCCGGTGATGTCCACCAGT

TACGACGTGGTGGTGGACCGGGAGTTTGACGAGCT

ACTGCAGGGCAAGGACGGCTTGCTCGTCTACCACA

AGATGCTCTCGGACGGCACGGTTAAGAACGCCCTC

AACTACATCTTCGGACGCATCCGCTCGGCGAAGTG

GTACGTAGAGCCCGCCTCTACCGACCCGGAAGACA

TCGCCATCGCCGCCTTCATCCACGCCCAGTTAGGC

ATAGACGACGCTTCGGTGGGCAAGTATCCCTTTGG

CCGCCTTTTCGCCATCTACGAAAACGCCTACATAT

ACGGCATGGCCGCCGGGGAAATCGTACTAACCCTT

GGCGCGGACGGCAAGCTCATCCTTGACAAAATCGT

CCCTATCCACCCTTTCAACATTGACGAGGTGCTTT

ACGACGAGGAAGGCGGTCCAAAGGCGCTAAAGCTA

AGCGGAGAGGTGAAGGGCGGAAGCCAGTTTGTGAG

CGGGTTGGAGATTCCTATATGGAAGACCGTGGTCT

TCCTGCACAACGACGACGGCTCCTTCACCGGACAG

AGCGCCCTCAGAGCCGCCGTGCCGCATTGGCTAGC

CAAACGAGCCCTCATTCTCCTCATCAACCACGGGT

TGGAGCGCTTCATGATTGGCGTGCCCACCCTCACC

ATCCCCAAGAGCGTGCGTCAGGGAACCAAGCAATG

GGAGGCCGCCAAGGAAATCGTCAAGAACTTTGTTC

AAAAACCACGGCATGGTATAATACTGCCTGACGAC

TGGAAGTTTGACACGGTAGACCTGAAGTCGGCCAT

GCCCGACGCCATTCCCTACCTGACCTACCACGACG

-continued

CGGGCATCGCTAGGGCGCTTGGCATAGACTTCAAC

ACCGTTCAACTAAACATGGGGGTACAGGCGAAGAA

CATCGGCGAGTTCGTAAGCCTGACCCAGCAGACCA

TCATTTCGCTCCAGCGGGAGTTCGCTAGCGCGGTC

AACCTCTACCTCATCCCCAAGCTAGTGCTTCCCAA

CTGGCCGAGCGCTACTCGCTTTCCTAGGCTCACCT

TTGAGATGGAGGAGCGCAACGACTTCTCCGCCGCG

GCCAACCTTATGGGCATGCTCATCAACGCGGTTAA

GGACTCCGAAGACATTCCCACCGAGCTCAAGGCGC

TAATAGACGCTCTGCCTAGCAAGATGCGCCGGGCG

CTTGGCGTGGTGGACGAGGTGAGGGAAGCGGTACG

CCAACCCGCCGATTAA

SEQ ID NO: 21

GPAKLEGASVPVMSTSYDVVVDREFDECLQGKDGL

LVYHKMLSDGTVKNALNYIFGRIRSAKWYVEPAST

DPEDIAIAAFIHAQLGIDDASVGKYPFGRLFAIYE

NAYIYGMAAGEIVLTLGADGKLILDKIVPIHPFNI

DEVLYDEEGGPKALKLSGEVKGGSQFVSGLEIPIW

KTVVFLHNDDGSFTGQSALRAAVPHWLAKRALILL

INHGLERFMIGVPTLTIPKSVRQGTKQWEAAKEIV

KNFVQKPRHGIILPDDWKFDTVDLKSAMPDAIPYL

TYHDAGIARALGIDFNTVQLNMGGQAGNIGEFVSL

TQQTIISLQREFASAVNLYLIPKLVLPNWPSATRF

PRLTFEMEERNDFSAAANLMGMLINAVKDSEDIPT

ELKALIDALPSKMRRALGVVDEVREAVRQPAD

SEQ ID NO: 22

ATGGGCAGCAGCCATCATcATCATCATCACAGCAG

CGGCCTGGAAGTTCTGTTCCAGGGACCAGCAAAGC

TCGAGGGCGCCTCCGTGCCGGTGATGTCCACCAGT

TACGACGTGGTGGTGGACCGGGAGTTTGACGAGTG

TCTGCAGGGCAAGGACGGCTTGCTCGTCTACCACA

AGATGCTCTCGGACGGCACGGTTAAGAACGCCCTC

AACTACATCTTCGGACGCATCCGCTCGGCGAAGTG

GTACGTAGAGCCCGCCTCTACCGACCCGGAAGACA

TCGCCATCGCCGCCTTCATCCACGCCCAGTTAGGC

ATAGACGACGCTTCGGTGGGCAAGTATCCCTTTGG

CCGCCTTTTCGCCATCTACGAAAACGCCTACATAT

ACGGCATGGCCGCCgggGAAATCGTACTAAcCCtt

GGCGCGGACGGCAAGCTCATCCTTGACaaaATCGT

CCCTAtcCACCCttTCAACATTGACGAGGTGCTTT

ACGACGAGGAAGGCGGTCCAAAGGCGCTAAAGCTA

AGCGGAGAGGTGAAgGGCGGAAGCCAGTTTGTGAG

-continued

CGGGTTGGAGATTCCTATATGGAAGACCGTGGTCT

TCCTGCACAACGACGACGGCTCCTTCACCGGACAG

AGCGCCCTCAGAGCCGCCGTGCCGCATTGGCTAGC

CAAACGAGCCCTCATTCTCCTCATCAACCACGGGT

TGGAGCGCTTCATGATTGGCGTGCCCACCCTCACC

ATCCCCAAGAGCGTGCGTCAGGGAACCAAGCAATG

GGAGGCCGCCAAGGAAATCGTCAAGAACTTTGTTC

AAAAACCACGGCATGGTATAATACTGCCTGACGAC

TGGAAGTTTGACACGGTAGACCTGAAGTCGGCCAT

GCCCGACGCCATTCCCTACCTGACCTACCACGACG

CGGGCATCGCTAGGGCGCTTGGCATAGACTTCAAC

ACCGTTCAACTAAACATGGGGGGACAGGCGGGAAA

CATCGGCGAGTTCGTAAGCCTGACCCAGCAGACCA

TCATTTCGCTCCAGCGGGAGTTCGCTAGCGCGGTC

AACCTCTACCTCATCCCCAAGCTAGTGCTTCCCAA

CTGGCCGAGCGCTACTCGCTTTCCTAGGCTCACCT

TTGAGATGGAGGAGCGCAACGACtTctcCGCCGCG

GCCAACCTTATGGGCATGCTCATCaACGCGGTTAA

GGACTCCGAAGACATTCCCACCGAGCTcaAGGCGC

TAATAGACGCTCTGCCTAGCAAGATGCGCCGGGCG

CTTGGCGTGGTGGacgAGGTGAGGGAAGCGGTAcG

CCaACCCGCCGATTaa

SEQ ID NO: 23

GPAKLEGASVPVMSTSYDVVVDREFDELLQGKDGL

LVYHKMLSDGTVKNALNYIFGRIRSAKWYVEPAST

DPEDIAIAAFIHAQLGIDDASVGKYPFGRLFAIYE

NAYIYGMAAGEIVLTLGADGKLILDKIVPIHPFNI

DEVLYDEEGGPKALKLSGEVKGGSQFVSGLEIPIW

KTVVFLHNDDGSFTGQSALRAAVPHWLAKRALILL

INHGLERFMIGVPTLTIPKSVRQGTKQWEAAKEIV

KNFVQKPRHGIILPDDWKFDTVDLKSAMPDAIPYL

TYHDAGIARALGIDFNTVQLNMGGGGNIGEFVSLT

QQTIISLQREFASAVNLYLIPKLVLPNWPSATRFP

RLTFEMEERNDFSAAANLMGMLINAVKDSEDIPTE

LKALIDALPSKMRRALGVVDEVREAVRQPAD

SEQ ID NO: 24

ATGGGCAGCAGCCATCATCATCATCATCACAGCAG

CGGCCTGGAAGTTCTGTTCCAGGGACCAGCAAAGC

TCGAGGGCGCCTCCGTGCCGGTGATGTCCACCAGT

TACGACGTGGTGGTGGACCGGGAGTTTGACGAGCT

ACTGCAGGGCAAGGACGGCTTGCTCGTCTACCACA

AGATGCTCTCGGACGGCACGGTTAAGAACGCCCTC

-continued

AACTACATCTTCGGACGCATCCGCTCGGCGAAGTG

GTACGTAGAGCCCGCCTCTACCGACCCGGAAGACA

TCGCCATCGCCGCCTTCATCCACGCCCAGTTAGGC

ATAGACGACGCTTCGGTGGGCAAGTATCCCTTTGG

CCGCCTTTTCGCCATCTACGAAAACGCCTACATAT

ACGGCATGGCCGCCGGGGAAATCGTACTAACCCTT

GGCGCGGACGGCAAGCTCATCCTTGACAAAATCGT

CCCTATCCACCCTTTCAACATTGACGAGGTGCTTT

ACGACGAGGAAGGCGGTCCAAAGGCGCTAAAGCTA

AGCGGAGAGGTGAAGGGCGGAAGCCAGTTTGTGAG

CGGGTTGGAGATTCCTATATGGAAGACCGTGGTCT

TCCTGCACAACGACGACGGCTCCTTCACCGGACAG

AGCGCCCTCAGAGCCGCCGTGCCGCATTGGCTAGC

CAAACGAGCCCTCATTCTCCTCATCAACCACGGGT

TGGAGCGCTTCATGATTGGCGTGCCCACCCTCACC

ATCCCCAAGAGCGTGCGTCAGGGAACCAAGCAATG

GGAGGCCGCCAAGGAAATCGTCAAGAACTTTGTTC

AAAAACCACGGCATGGTATAATACTGCCTGACGAC

TGGAAGTTTGACACGGTAGACCTGAAGTCGGCCAT

GCCCGACGCCATTCCCTACCTGACCTACCACGACG

CGGGCATCGCTAGGGCGCTTGGCATAGACTTCAAC

ACCGTTCAACTAAACATGGGGGGAGGCGGTAACAT

CGGCGAGTTCGTAAGCCTGACCCAGCAGACCATCA

TTTCGCTCCAGCGGGAGTTCGCTAGCGCGGTCAAC

CTCTACCTCATCCCCAAGCTAGTGCTTCCCAACTG

GCCGAGCGCTACTCGCTTTCCTAGGCTCACCTTTG

AGATGGAGGAGCGCAACGACTTCTCCGCCGCGGCC

AACCTTATGGGCATGCTCATCAACGCGGTTAAGGA

CTCCGAAGACATTCCCACCGAGCTCAAGGCGCTAA

TAGACGCTCTGCCTAGCAAGATGCGCCGGGCGCTT

GGCGTGGTGGACGAGGTGAGGGAAGCGGTACGCCA

ACCCGCCGATTAA

SEQ ID NO: 25

GPAKLEGASVPVMSTSYDVVVDREFDECLQGKDGL

LVYHKMLSDGTVKNALNYIFGRIRSAKWYVEPAST

DPEDIAIAAFIHAQLGIDDASVGKYPFGRLFAIYE

NAYIYGMAAGEIVLTLGADGKLILDKIVPIHPFNI

DEVLYDEEGGPKALKLSGEVKGGSQFVSGLEIPIW

KTVVFLHNDDGSFTGQSALRAAVPHWLAKRALILL

INHGLERFMIGVPTLTIPKSVRQGTKQWEAAKEIV

KNFVQKPRHGIILPDDWKFDTVDLKSAMPDAIPYL

-continued

TYHDAGIARALGIDFNTVQLGIGEFVSLTQQTIIS
LQREFASAVNLYLIPKLVLPNWPSATRFPRLTFEM
EERNDFSAAANLMGMLINAVKDSEDIPTELKALID
ALPSKMRRALGVVDEVREAVRQPAD

SEQ ID NO: 26 cATCATCACAGCAGCGGCCTGGAAGTTCTGTTCCA
GGGACCAGCAAAGCTCGAGGGCGCCTCCGTGCCGG
TGATGTCCACCAGTTACGACGTGGTGGTGGACCGG
GAGTTTGACGAGTGTCTGCAGGGCAAGGACGGCTT
GCTCGTCTACCACAAGATGCTCTCGGACGGCACGG
TTAAGAACGCCCTCAACTACATCTTCGGACGCATC
CGCTCGGCGAAGTGGTACGTAGAGCCCGCCTCTAC
CGACCCGGAAGACATCGCCATCGCCGCCTTCATCC
ACGCCCAGTTAGGCATAGACGACGCTTCGGTGGGC
AAGTATCCCTTTGGCCGCCTTTTCGCCATCTACGA
AAACGCCTACATATACGGCATGGCCGCCGGGGAAA
TCGTACTAACCCTTGGCGCGGACGGCAAGCTCATC
CTTGACAAAATCGTCCCTATCCACCCTTTCAACAT
TGACGAGGTGCTTTACGACGAGGAAGGCGGTCCAA
AGGCGCTAAAGCTAAGCGGAGAGGTGAAGGGCGGA
AGCCAGTTTGTGAGCGGGTTGGAGATTCCTATATG
GAAGACCGTGGTCTTCCTGCACAACGACGACGGCT
CCTTCACCGGACAGAGCGCCCTCAGAGCCGCCGTG
CCGCATTGGCTAGCCAAACGAGCCCTCATTCTCCT
CATCAACCACGGGTTGGAGCGCTTCATGATTGGCG
TGCCCACCCTCACCATCCCCAAGAGCGTGCGTCAG
GGAACCAAGCAATGGGAGGCCGCCAAGGAAATCGT
CAAGAACTTTGTTCAAAAACCACGGCATGGTATAA
TACTGCCTGACGACTGGAAGTTTGACACGGTAGAC
CTGAAGTCGGCCATGCCCGACGCCATTCCCTACCT
GACCTACCACGACGCGGGCATCGCTAGGGCGCTTG
GCATAGACTTCAACACCGTTCAACTAGGTATCGGC
GAGTTCGTAAGCCTGACCCAGCAGACCATCATTTC
GCTCCAGCGGGAGTTCGCTAGCGCGGTCAACCTCT
ACCTCATCCCCAAGCTAGTGCTTCCCAACTGGCCG
AGCGCTACTCGCTTTCCTAGGCTCACCTTTGAGAT
GGAGGAGCGCAACGACTTCTCCGCCGCGGCCAACC
TTATGGGCATGCTCATCAACGCGGTTAAGGACTCC
GAAGACATTCCCACCGAGCTCAAGGCGCTAATAGA
CGCTCTGCCTAGCAAGATGCGCCGGGCGCTTGGCG

-continued

TGGTGGACGAGGTGAGGGAAGCGGTACGCCAACCC
GCCGantaa

SEQ ID NO: 27

GPAKLEGASVPVMSTSYDVVVDREFDECLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPNDWKFNTVNLKSAMPNAIPYL
TYHDAGIARALGIDFNTVQLNMGVQAINIGEFVSL
TQQTIISLQREFASAANLYLIPKLVLPNWPSATRF
PRLTFEMEERNDFSAAANLMGMLINAVKDSEDIPT
ELKALIDALPSKMRRALGVVDEVREAVRQPAD

SEQ ID NO: 28

ATGGGCAGCAGCCATCATCATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGTG
TCTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCGGGGAAATCGTACTAACCCTT
GGCGCGGACGGCAAGCTCATCCTTGACAAAATCGT
CCCTATCCACCCTTTCAACATTGACGAGGTGCTTT
ACGACGAGGAAGGCGGTCCAAAGGCGCTAAAGCTA
AGCGGAGAGGTGAAGGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAATCGTCAAGAACTTTGTTC
AAAAACCACGGCATGGTATAATACTGCCTAACGAC
TGGAAGTTTAACACGGTAAACCTGAAGTCGGCCAT
GCCCAACGCCATTCCCTACCTGACCTACCACGACG

-continued

CGGGCATCGCTAGGGCGCTTGGCATAGACTTCAAC
ACCGTTCAACTAAACATGGGGGTACAGGCGATAAA
CATCGGCGAGTTCGTAAGCCTGACCCAGCAGACCA
TCATTTCGCTCCAGCGGGAGTTCGCTAGCGCGGCC
AACCTCTACCTCATCCCCAAGCTAGTGCTTCCCAA
CTGGCCGAGCGCTACTCGCTTTCCTAGGCTCACCT
TTGAGATGGAGGAGCGCAACGACTTCTCCGCCGCG
GCCAACCTTATGGGCATGCTCATCAACGCGGTTAA
GGACTCCGAAGACATTCCCACCGAGCTCAAGGCGC
TAATAGACGCTCTGCCTAGCAAGATGCGCCGGGCG
CTTGGCGTGGTGGACGAGGTGAGGGAAGCGGTACG
CCAACCCGCCGATTAA

SEQ ID NO: 29

GPAKLEGASVPVMSTSYDVVVDREFDEGTPGSRGL
LQGKDGLLVYHKMLSDGTVKNALNYIFGRIRSAKW
YVEPASTDPEDIAIAAFIHAQLGIDDASVGKYPFG
RLFAIYENAYIYGMAAGEIVLTLGADGKLILDKIV
PIHPFNIDEVLYDEEGGPKALKLSGEVKGGSQFVS
GLEIPIWKTVVFLHNDDGSFTGQSALRAAVPHWLA
KRALILLINHGLERFMIGVPTLTIPKSVRQGTKQW
EAAKEIVKNFVQKPRHGIILPNDWKFNTVNLKSAM
PNAIPYLTYHDAGIARALGIDFNTVQLNMGVQAIN
IGEFVSLTQQTIISLQREFASAVNLYLIPKLVLPN
WPSATRFPRLTFEMEERNDFSAAANLMGMLINAVK
DSEDIPTELKALIDALPSKMRRALGVVDEVREAVR
QPAD

SEQ ID NO: 30

ATGGGCAGCAGCCATCATCATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGGG
TACGCCAGGTTCTCGCGGCCTACTGCAGGGCAAGG
ACGGCTTGCTCGTCTACCACAAGATGCTCTCGGAC
GGCACGGTTAAGAACGCCCTCAACTACATCTTCGG
ACGCATCCGCTCGGCGAAGTGGTACGTAGAGCCCG
CCTCTACCGACCCGGAAGACATCGCCATCGCCGCC
TTCATCCACGCCCAGTTAGGCATAGACGACGCTTC
GGTGGGCAAGTATCCCTTTGGCCGCCTTTTCGCCA
TCTACGAAAACGCCTACATATACGGCATGGCCGCC
GGGGAAATCGTACTAACCCTTGGCGCGGACGGCAA
GCTCATCCTTGACAAAATCGTCCCTATCCACCCTT
TCAACATTGACGAGGTGCTTTACGACGAGGAAGGC

-continued

GGTCCAAAGGCGCTAAAGCTAAGCGGAGAGGTGAA
GGGCGGAAGCCAGTTTGTGAGCGGGTTGGAGATTC
CTATATGGAAGACCGTGGTCTTCCTGCACAACGAC
GACGGCTCCTTCACCGGACAGAGCGCCCTCAGAGC
CGCCGTGCCGCATTGGCTAGCCAAACGAGCCCTCA
TTCTCCTCATCAACCACGGGTTGGAGCGCTTCATG
ATTGGCGTGCCCACCCTCACCATCCCCAAGAGCGT
GCGTCAGGGAACCAAGCAATGGGAGGCCGCCAAGG
AAATCGTCAAGAACTTTGTTCAAAAACCACGGCAT
GGTATAATACTGCCTAACGACTGGAAGTTTAACAC
GGTAAACCTGAAGTCGGCCATGCCCAACGCCATTC
CCTACCTGACCTACCACGACGCGGGCATCGCTAGG
GCGCTTGGCATAGACTTCAACACCGTTCAACTAAA
CATGGGGGTACAGGCGATAAACATCGGCGAGTTCG
TAAGCCTGACCCAGCAGACCATCATTTCGCTCCAG
CGGGAGTTCGCTAGCGCGGTCAACCTCTACCTCAT
CCCCAAGCTAGTGCTTCCCAACTGGCCGAGCGCTA
CTCGCTTTCCTAGGCTCACCTTTGAGATGGAGGAG
CGCAACGACTTCTCCGCCGCGGCCAACCTTATGGG
CATGCTCATCAACGCGGTTAAGGACTCCGAAGACA
TTCCCACCGAGCTCAAGGCGCTAATAGACGCTCTG
CCTAGCAAGATGCGCCGGGCGCTTGGCGTGGTGGA
CGAGGTGAGGGAAGCGGTACGCCAACCCGCCGATT
AA

SEQ ID NO: 31

GPAKLEGASVPVMSTSYDVVVDREFDEGRKLPDAG
LLQGKDGLLVYHKMLSDGTVKNALNYIFGRIRSAK
WYVEPASTDPEDIAIAAFIHAQLGIDDASVGKYPF
GRLFAIYENAYIYGMAAGEIVLTLGADGKLILDKI
VPIHPFNIDEVLYDEEGGPKALKLSGEVKGGSQFV
SGLEIPIWKTVVFLHNDDGSFTGQSALRAAVPHWL
AKRALILLINHGLERFMIGVPTLTIPKSVRQGTKQ
WEAAKEIVKNFVQKPRHGIILPNDWKFNTVNLKSA
MPNAIPYLTYHDAGIARALGIDFNTVQLNMGVQAI
NIGEFVSLTQQTIISLQREFASAVNLYLIPKLVLP
NWPSATRFPRLTFEMEERNDFSAAANLMGMLINAV
KDSEDIPTELKALIDALPSKMRRALGVVDEVREAV
RQPAD

SEQ ID NO: 32

ATGGGCAGCAGCCatCaTCAtcatCATCACAGCAG
CGGCCTGGAAGTTCTGTTCCAGGGACCAGCAAAGC

-continued

TCGAGGGCGCCTCCGTGCCGGTGATGTCCACCAGT
TACGACGTGGTGGTGGACCGGGAGTTTGACGAGGG
TCGTAAACTGCCGGATGCAGGCCTACTGCAGGGCA
AGGACGGCTTGCTCGTCTACCACAAGATGCTCTCG
GACGGCACGGTTAAGAACGCCCTCAACTACATCTT
CGGACGCATCCGCTCGGCGAAGTGGTACGTAGAGC
CCGCCTCTACCGACCCGGAAGACATCGCCATCGCC
GCCTTCATCCACGCCCAGTTAGGCATAGACGACGC
TTCGGTGGGCAAGTATCCCTTTGGCCGCCTTTTCG
CCATCTACGAAAACGCCTACATATACGGCATGGCC
GCCGGGGAAATCGTACTAACCCTTGGCGCGGACGG
CAAGCTCATCCTTGACAAAATCGTCCCTATCCACC
CTTTCAACATTGACGAGGTGCTTTACGACGAGGAA
GGCGGTCCAAAGGCGCTAAAGCTAAGCGGAGAGGT
GAAGGGCGGAAGCCAGTTTGTGAGCGGGTTGGAGA
TTCCTATATGGAAGACCGTGGTCTTCCTGCACAAC
GACGACGGCTCCTTCACCGGACAGAGCGCCCTCAG
AGCCGCCGTGCCGCATTGGCTAGCCAAACGAGCCC
TCATTCTCCTCATCAACCACGGGTTGGAGCGCTTC
ATGATTGGCGTGCCCACCCTCACCATCCCCAAGAG
CGTGCGTCAGGGAACCAAGCAATGGGAGGCCGCCA
AGGAAATCGTCAAGAACTTTGTTCAAAAACCACGG
CATGGTATAATACTGCCTAACGACTGGAAGTTTAA
CACGGTAAACCTGAAGTCGGCCATGCCCAACGCCA
TTCCCTACCTGACCTACCACGACGCGGGCATCGCT
AGGGCGCTTGGCATAGACTTCAACACCGTTCAACT
AAACATGGGGGTACAGGCGATAAACATCGGCGAGT
TCGTAAGCCTGACCCAGCAGACCATCATTTCGCTC
CAGCGGGAGTTCGCTAGCGCGGTCAACCTCTACCT
CATCCCCAAGCTAGTGCTTCCCAACTGGCCGAGCG
CTACTCGCTTTCCTAGGCTCACCTTTGAGATGGAG
GAGCGCAACGACTTCTCCGCCGCGGCCAACCTTAT
GGGCATGCTCATCAACGCGGTTAAGGACTCCGAAG
ACATTCCCACCGAGCTCAAGGCGCTAATAGACGCT
CTGCCTAGCAAGATGCGCCGGGCGCTTGGCGTGGT
GGACGAGGTGAGGGAAGCGGTACGCCAACCCGCCG
AtTAA

-continued

SEQ ID NO: 33

GPASSKKSGSYSGSKGSKLEGASVPVMSTSYDVVV
DREFDECLQGKDGLLVYHKMLSDGTVKNALNYIFG
RIRSAKWYVEPASTDPEDIAIAAFIHAQLGIDDAS
VGKYPFGRLFAIYENAYIYGMAAGEIVLTLGADGK
LILDKIVPIHPFNIDEVLYDEEGGPKALKLSGEVK
GGSQFVSGLEIPIWKTVVFLHNDDGSFTGQSALRA
AVPHWLAKRALILLINHGLERFMIGVPTLTIPKSV
RQGTKQWEAAKEIVKNFVQKPRHGIILPNDWKFNT
VNLKSAMPNAIPYLTYHDAGIARALGIDFNTVQLN
MGVQAINIGEFVSLTQQTIISLQREFASAANLYLI
PKLVLPNWPSATRFPRLTFEMEERNDFSAAANLMG
MLINAVKDSEDIPTELKALIDALPSKMRRALGVVD
EVREAVRQPAD

SEQ ID NO: 34

ATGGGCAGCAGCCATCATCATCATCATCACAGCAG
CGGCCTGGAAGTTCTGTTCCAGGGACCAGCAAGCA
GTAAGAAAAGTGGAAGCTATAGCGGCAGCAAAGGC
AGCAAGCTCGAGGGCGCCTCCGTGCCGGTGATGTC
CACCAGTTACGACGTGGTGGTGGACCGGGAGTTTG
ACGAGTGTCTGCAGGGCAAGGACGGCTTGCTCGTC
TACCACAAGATGCTCTCGGACGGCACGGTTAAGAA
CGCCCTCAACTACATCTTCGGACGCATCCGCTCGG
CGAAGTGGTACGTAGAGCCCGCCTCTACCGACCCG
GAAGACATCGCCATCGCCGCCTTCATCCACGCCCA
GTTAGGCATAGACGACGCTTCGGTGGGCAAGTATC
CCTTTGGCCGCCTTTTCGCCATCTACGAAAACGCC
TACATATACGGCATGGCCGCCGGGGAAATCGTACT
AACCCTTGGCGCGGACGGCAAGCTCATCCTTGACA
AAATCGTCCCTATCCACCCTTTCAACATTGACGAG
GTGCTTTACGACGAGGAAGGCGGTCCAAAGGCGCT
AAAGCTAAGCGGAGAGGTGAAGGGCGGAAGCCAGT
TTGTGAGCGGGTTGGAGATTCCTATATGGAAGACC
GTGGTCTTCCTGCACAACGACGACGGCTCCTTCAC
CGGACAGAGCGCCCTCAGAGCCGCCGTGCCGCATT
GGCTAGCCAAACGAGCCCTCATTCTCCTCATCAAC
CACGGGTTGGAGCGCTTCATGATTGGCGTGCCCAC
CCTCACCATCCCCAAGAGCGTGCGTCAGGGAACCA
AGCAATGGGAGGCCGCCAAGGAAATCGTCAAGAAC
TTTGTTCAAAAACCACGGCATGGTATAATACTGCC
TAACGACTGGAAGTTTAACACGGTAAACCTGAAGT
CGGCCATGCCCAACGCCATTCCCTACCTGACCTAC

-continued

CACGACGCGGGCATCGCTAGGGCGCTTGGCATAGA

CTTCAACACCGTTCAACTAAACATGGGGGTACAGG

CGATAAACATCGGCGAGTTCGTAAGCCTGACCCAG

CAGACCATCATTTCGCTCCAGCGGGAGTTCGCTAG

CGCGGCCAACCTCTACCTCATCCCCAAGCTAGTGC

TTCCCAACTGGCCGAGCGCTACTCGCTTTCCTAGG

CTCACCTTTGAGATGGAGGAGCGCAACGACTTCTC

CGCCGCGGCCAACCTTATGGGCATGCTCATCAACG

CGGTTAAGGACTCCGAAGACATTCCCACCGAGCTC

AAGGCGCTAATAGACGCTCTGCCTAGCAAGATGCG

CCGGGCGCTTGGCGTGGTGGACGAGGTGAGGGAAG

CGGTACGCCAACCCGCCGATTAA

SEQ ID NO: 35

GPAKLEGASVPVMSTSYDVVVDREFDEGYRPGFYF

RLLQGKDGLLVYHKMLSDGTVKNALNYIFGRIRSA

KWYVEPASTDPEDIAIAAFIHAQLGIDDASVGKYP

FGRLFAIYENAYIYGMAAGEIVLTLGADGKLILDK

IVPIHPFNIDEVLYDEEGGPKALKLSGEVKGGSQF

VSGLEIPIWKTVVFLHNDDGSFTGQSALRAAVPHW

LAKRALILLINHGLERFMIGVPTLTIPKSVRQGTK

QWEAAKEIVKNFVQKPRHGIILPNDWKFNTVNLKS

AMPNAIPYLTYHDAGIARALGIDFNTVQLNMGVQA

INIGEFVSLTQQTIISLQREFASAVNLYLIPKLVL

PNWPSATRFPRLTFEMEERNDFSAAANLMGMLINA

VKDSEDIPTELKALIDALPSKMRRALGVVDEVREA

VRQPAD

SEQ ID NO: 36

ATGGGCAGCAGCCATCATCATCATCATCACAGCAG

CGGCCTGGAAGTTCTGTTCCAGGGACCAGCAAAGC

TCGAGGGCGCCTCCGTGCCGGTGATGTCCACCAGT

TACGACGTGGTGGTGGACCGGGAGTTTGACGAGGG

ATATCGCCCGGGCTTTTATTTTCGCCTACTGCAGG

GCAAGGACGGCTTGCTCGTCTACCACAAGATGCTC

TCGGACGGCACGGTTAAGAACGCCCTCAACTACAT

CTTCGGACGCATCCGCTCGGCGAAGTGGTACGTAG

AGCCCGCCTCTACCGACCCGGAAGACATCGCCATC

GCCGCCTTCATCCACGCCCAGTTAGGCATAGACGA

CGCTTCGGTGGGCAAGTATCCCTTTGGCCGCCTTT

TCGCCATCTACGAAAACGCCTACATATACGGCATG

GCCGCCGGGGAAATCGTACTAACCCTTGGCGCGGA

CGGCAAGCTCATCCTTGACAAAATCGTCCCTATCC

ACCCTTTCAACATTGACGAGGTGCTTTACGACGAG

GAAGGCGGTCCAAAGGCGCTAAAGCTAAGCGGAGA

GGTGAAGGGCGGAAGCCAGTTTGTGAGCGGGTTGG

AGATTCCTATATGGAAGACCGTGGTCTTCCTGCAC

AACGACGACGGCTCCTTCACCGGACAGAGCGCCCT

CAGAGCCGCCGTGCCGCATTGGCTAGCCAAACGAG

CCCTCATTCTCCTCATCAACCACGGGTTGGAGCGC

TTCATGATTGGCGTGCCCACCCTCACCATCCCCAA

GAGCGTGCGTCAGGGAACCAAGCAATGGGAGGCCG

CCAAGGAAATCGTCAAGAACTTTGTTCAAAAACCA

CGGCATGGTATAATACTGCCTAACGACTGGAAGTT

TAACACGGTAAACCTGAAGTCGGCCATGCCCAACG

CCATTCCCTACCTGACCTACCACGACGCGGGCATC

GCTAGGGCGCTTGGCATAGACTTCAACACCGTTCA

ACTAAACATGGGGGTACAGGCGATAAACATCGGCG

AGTTCGTAAGCCTGACCCAGCAGACCATCATTTCG

CTCCAGCGGGAGTTCGCTAGCGCGGTCAACCTCTA

CCTCATCCCCAAGCTAGTGCTTCCCAACTGGCCGA

GCGCTACTCGCTTTCCTAGGCTCACCTTTGAGATG

GAGGAGCGCAACGACTTCTCCGCCGCGGCCAACCT

TATGGGCATGCTCATCAACGCGGTTAAGGACTCCG

AAGACATTCCCACCGAGCTCAAGGCGCTAATAGAC

GCTCTGCCTAGCAAGATGCGCCGGGCGCTTGGCGT

GGTGGACGAGGTGAGGGAAGCGGTACGCCAACCCG

CCGATTAA

SEQ ID NO: 37

MAKRGRKPKELVPGPGSIDPSDVPKLEGASVPVMS

TSYDVVVDREFDELLQGKDGLLVYHKMLSDGTVKN

ALNYIFGRIRSAKWYVEPASTDPEDIAIAAFIHAQ

LGIDDASVGKYPFGRLFAIYENAYIYGMAAGEIVL

TLGADGKLILDKIVPIHPFNIDEVYDEEGGPKALK

LSGEVKGGSQFVSGLEIPIWKTVVFLHNDDGSFTG

QSALRAAVPHWLAKRALILLINHGLERFMIGVPTL

TIPKSVRQGTKQWEAAKEIVKNFVQKPRHGIILPD

DWKFDTVDLKSAMPDAIPYLTYHDAGIARALGIDF

NTVQLNMGVQAINIGEFVSLTQQTIISLQREFASA

VNLYLIPKLVLPNWPSATRFPRLTFEMEERNDFSA

AANLMGMLINAVKCSEDIPTELKALIDALPSKMRR

ALGVVDEVREAVRQPADLEHHHHHH

SEQ ID NO: 38

ATGGCTAAGCGAGGACGTAAACCCAAAGAGCTGGT

CCCCGGACCTGGCTCCATTGACCCATCTGACGTTC

CCAAGCTCGAGGGCGCCTCCGTGCCGGTGATGTCC

-continued

ACCAGTTACGACGTGGTGGTGGACCGGGAGTTTGA
CGAGCTACTGCAGGGCAAGGACGGCTTGCTCGTCT
ACCACAAGATGCTCTCGGACGGCACGGTTAAGAAC
GCCCTCAACTACATCTTCGGACGCATCCGCTCGGC
GAAGTGGTACGTAGAGCCCGCCTCTACCGACCCGG
AAGACATCGCCATCGCCGCCttCATccacgcCCAG
TTAGGCATAGACGACGCTTCgGtgGGCAAGTATcC
CtttgGCCGcCTTTTcgCCATctACGAAAACGCCT
ACATATACGGCATGGCCGCCggGGAAATCGTACTA
AccCTTGGCGCGGACGGCAAGCTCATCCTTGACAA
AATCGTcCCTATCCACCCTTTCAACATTGACGAGG
TGCnTTACGACGAGGAAGGCGGTCCAAAGGCGCTA
AAGCTAAGCGGAGAGGTGAAGGGCGGAAGCCAGTT
TGTGAGCGGGTTGGAGATTCCTATATGGAAGACCG
TGGTCTTCCTGCACAACGACGACGGCTCCTTCACC
GGACAGAGCGCCCTCAGAGCCGCCGTGCCGCATTG
GCTAGCCAAACGAGCCCTCATTCTCCTCATCAACC
ACGGGTTGGAGCGCTTCATGATTGGCGTGCCCACC
CTCACCATCCCCAAGAGCGTGCGTCAGGGAACCAA
GCAATGGGAGGCCGCCAAGGAAATCGTCAAGAACT
TTGTTCAAAAACCACGGCATGGTATAATACTGCCT
GACGACTGGAAGTTTGACACGGTAGACCTGAAGTC
GGCCATGCCCGACGCCATTCCCTACCTGACCTACC
ACGACGCGGGCATCGCTAGGGCGCTTGGCATAGAC
TTCAACACCGTTCAACTAAACATGGGGGTACAGGC
GATAAACATCGGCGAGTTCGTAAGCCTGACCCAGC
AGACCATCATTTCGCTCCAGCGGGAGTTCGCTAGC
GCGGTCAACCTCTACCTCATCCCCAAGCTAGTGCT
TCCCAACTGGCCGAGCGCTACTCGCTTTCCTAGGC
TCACCTTTGAGATGGAGGAGCGCAACGACTTCTCC
GCCGCGGCCAACCTTATGGGCATGCTCATCAACGC
GGTTAAGTGCTCCGAAGACATTCCCACCGAGCTCA
AGGCGCTAATAGACGCTCTGCCTAGCAAGATGCGC
CGGGCGCTTGGCGTGGTGGACGAGGTGAGGGAAGC
GGTACGCCAACCCGCCGATCTCGAGCACCACCACC
ACCACCACTGA

SEQ ID NO: 39

MGSSHHHHHHSSGLEVLFQGPAKLEGASVPVMSTS
YDVVVDREFDELLQGKDGLLVYHKMLSDGTVKNAL
NYIFGRIRSAKWYVEPASTDPEDIAIAAFIHAQLG
IDDASVGKYPFGRLFAIYENAYIYGMAAGEIVLTL
GADGKLILDKIVPIHPFNIDEVLYDEEGGPKALKL
SGEVKGGSQFVSGLEIPIWKTVVFLHNDDGSFTGQ
SALRAAVPHWLAKRALILLINHGLERFMIGVPTLT
IPKSVRQGTKQWEAAKEIVKNFVQKPRHGIILPDD
WKFDTVDLKSAMPDAIPYLTYHDAGIARALGIDFN
TVQLNMGVQAINIGEFVSLTQQTIISLQREFASAV
NLYLIPKLVLPNWPSATRFPRLTFEMEERNDFSAA
ANLMGMLINAVKDSEDIPTELKALIDALPSKMRRA
LGVVDEVREAVRQPAD

SEQ ID NO: 40

MAKRGRKPKELVPGPGSIDPSDVPKLEGASVPVMS
TSYDVVVDREFDELLQGKDGLLVYHKMLSDGTVKN
ALNYIFGRIRSAKWYVEPASTDPEDIAIAAFIHAQ
LGIDDASVGKYPFGRLFAIYENAYIYGMAAGEIVL
TLGADGKLILDKIVPIHPFNIDEVLYDEEGGPKAL
KLSGEVKGGSQFVNGLEIPIWKTVVFLHNDDGSFT
GQSALRAAVPHWLAKRALILLINHGLERFMIGVPT
LTIPKSVRQGTKQWEAAKEIVKNFVQKPRHGIILP
DDWKFDTVDLKSAMPDAIPYLTYHDAGIARALGID
FNTVQLNMGVQAVNIGEFVSLTQQTIISLQREFAS
AVNLYLIPKLVLPNWPGATRFPRLTFEMEERNDFS
AAANLMGMLINAVKDSEDIPTELKALIDALPSKMR
RALGVVDEVREAVRQPADSRYLYTRRRR

SEQ ID NO: 41

ATGGCTAAGCGAGGACGTAAACCCAAGGAGCTGGT
CCCCGGACCTGGCTCCATTGACCCATCCGACGTTC
CCAAGCTCGAGGGCGCCTCCGTGCCGGTGATGTCC
ACCAGCTACGACGTGGTGGTTGACCGGGAGTTTGA
CGAGCTACTGCAGGGCAAGGACGGCCTGCTCGTCT
ACCACAAGATGCTCTCGGACGGCACGGTCAAGAAC
GCCCTCAACTACATCTTCGGGCGCATCCGCTCGGC
GAAGTGGTACGTAGAGCCCGCCTCTACCGACCCGG
AGGACATCGCCATCGCCGCCTTCATCCACGCCCAG
TTAGGCATAGACGATGCTTCGGTAGGCAAGTATCC
TTTTGGCCGTCTTTTCGCCATCTACGAAAACGCCT
ACATATACGGCATGGCCGCCGGGGAAATCGTACTG
ACCCTTGGCGCGGACGGCAAGCTCATCCTTGACAA
AATCGTCCCTATCCACCCTTTCAACATTGACGAGG
TGCTTTACGACGAGGAAGGCGGTCCAAAGGCGCTA
AAGCTAAGCGGAGAGGTGAAGGGCGGAAGCCAGTT
CGTGAACGGGCTGGAGATTCCTATCTGGAAGACCG
TGGTCTTCCTGCACAACGACGACGGCTCCTTCACC

-continued

```
GGACAGAGCGCCCTCAGAGCCGCCGTTCCGCATTG

GCTAGCCAAACGCGCCCTTATCCTCCTCATCAACC

ACGGGCTAGAGCGCTTCATGATTGGCGTGCCCACC

CTCACCATCCCCAAGAGCGTGCGTCAGGGGACCAA

GCAATGGGAGGCCGCCAAGGAAATCGTCAAGAACT

TTGTTCAAAAACCACGGCATGGTATAATACTGCCT

GACGACTGGAAGTTTGACACGGTAGACCTGAAGTC

GGCCATGCCCGACGCCATTCCCTACCTGACCTACC

ACGACGCGGGCATCGCTAGGGCGCTTGGCATAGAC

TTCAACACCGTTCAGCTAAACATGGGGGTACAGGC

GGTCAACATCGGCGAGTTCGTAAGCCTGACCCAGC

AGACCATCATTTCGCTCCAGCGGGAGTTCGCTAGC

GCGGTCAACCTCTACCTCATCCCCAAGCTAGTGCT

TCCCAACTGGCCGGGCGCCACCCGCTTTCCCAGGC

TCACCTTTGAGATGGAGGAGCGTAACGACTTCTCC

GCCGCGGCCAACCTTATGGGCATGCTCATCAACGC

GGTTAAGGACTCCGAAGACATTCCCACCGAGCTCA

AGGCGCTAATAGACGCTCTGCCCAGCAAGATGCGC

CGGGCGCTTGGCGTGGTGGACGAGGTGAGGGAAGC

GGTACGCCAACCCGCCGATTCCCGCTACCTGTACA

CGCGAAGGAGGAGGTAG
```

REFERENCES

1. Wang, H. et al. Determining the Physical Properties of Molecules with Nanometer-Scale Pores. *ACS Sensors* 3, 251-263 (2018).
2. Derrington, I. M. et al. Nanopore DNA sequencing with MspA. *Proc. Natl. Acad. Sci. U.S.A.* 107, 16060-16065 (2010).
3. Nivala, J., Marks, D. B. & Akeson, M. Unfoldase-mediated protein translocation through an α-hemolysin nanopore. *Nat Biotechnol* 31, 247-250 (2013).
4. Rodriguez-Larrea, D. & Bayley, H. Multistep protein unfolding during nanopore translocation. *Nature Nanotech* 8, 288-295 (2013).
5. Gu, L. Q., Braha, O., Conlan, S., Cheley, S. & Bayley, H. Stochastic sensing of organic analytes by a pore-forming protein containing a molecular adapter. *Nature* 398, 686-690 (1999).
6. Butler, T. Z., Pavlenok, M., Derrington, I. M., Niederweis, M. & Gundlach, J. H. Single-molecule DNA detection with an engineered MspA protein nanopore. *Proc. Natl. Acad. Sci. U.S.A.* 105, 20647-20652 (2008).
7. Kasianowicz, J. J. et al. Analytical applications for pore-forming proteins. *Biochim Biophys Acta* 1858, 593-606 (2016).
8. Zhang, M. et al. Thermophoresis-Controlled Size-Dependent DNA Translocation through an Array of Nanopores. *ACS Nano* acsnano.8b00961 (2018). doi:10.1021/acsnano.8b00961
9. Larkin, J., Henley, R. Y., Jadhav, V., Korlach, J. & Wanunu, M. Length-independent DNA packing into nanopore zero-mode waveguides for low-input DNA sequencing. *Nat Nano* 12, 1169-1175 (2017).
10. McNally, B. et al. Optical Recognition of Converted DNA Nucleotides for Single-Molecule DNA Sequencing Using Nanopore Arrays. *Nano Lett* 10, 2237-2244 (2010).
11. Jain, M. et al. Nanopore sequencing and assembly of a human genome with ultra-long reads. *Nature Biotechnology* 36, 338-345 (2018).
12. Jain, M. et al. Improved data analysis for the MinION nanopore sequencer. *Nature Methods* 12, 351-356 (2015).
13. Loman, N. J., Quick, J. & Simpson, J. T. A complete bacterial genome assembled de novo using only nanopore sequencing data. *Nature Methods* 12, 733-735 (2015).
14. Garalde, D. R. et al. Highly parallel direct RNA sequencing on an array of nanopores. *Nature Methods* 15, 201-206 (2018).
15. Howorka, S. & Si, Z. Nanopore analytics: sensing of single molecules. *Chem. Soc. Rev.* 38, 2360 (2009).
16. Kasianowicz, J. J., Brandin, E., Branton, D. & Deamer, D. W. Characterization of individual polynucleotide molecules using a membrane channel. *Proc. Natl. Acad. Sci. U.S.A.* 93, 13770-13773 (1996).
17. Mohammad, M. M. et al. Engineering a rigid protein tunnel for biomolecular detection. *JAm Chem Soc* 134, 9521-9531 (2012).
18. Robertson, J. W. F. et al. Single-molecule mass spectrometry in solution using a solitary nanopore. *Proc. Natl. Acad. Sci. U.S.A.* 104, 8207-8211 (2007).
19. Merstorf, C. et al. Wild type, mutant protein unfolding and phase transition detected by single-nanopore recording. *ACS Chem Biol* 7, 652-658 (2012).
20. Huang, G., Willems, K., Soskine, M., Wloka, C. & Maglia, G. Electro-osmotic capture and ionic discrimination of peptide and protein biomarkers with FraC nanopores. *Nature Communications* 8, 935 (2017).
21. Piguet, F. et al. Identification of single amino acid differences in uniformly charged homopolymeric peptides with aerolysin nanopore. *Nature Communications* 9, (2018).
22. Luchian, T., Shin, S.-H. & Bayley, H. Kinetics of a three-step reaction observed at the single-molecule level. *Angew Chem Int Ed Engl* 42, 1926-1929 (2003).
23. Wescoe, Z. L., Schreiber, J. & Akeson, M. Nanopores discriminate among five C5-cytosine variants in DNA. *JAm Chem Soc* 136, 16582-16587 (2014).
24. Baaken, G. et al. High-Resolution Size-Discrimination of Single Nonionic Synthetic Polymers with a Highly Charged Biological Nanopore. *ACS Nano* 9, 6443-6449 (2015).
25. Fennouri, A. A. et al. Single molecule detection of glycosaminoglycan hyaluronic acid oligosaccharides and depolymerization enzyme activity using a protein nanopore. *ACS Nano* 6, 9672-9678 (2012).
26. Lee, J. et al. Semisynthetic Nanoreactor for Reversible Single-Molecule Covalent Chemistry. *ACS Nano* 10, 8843-8850 (2016).
27. Willems, K., Van Meervelt, V., Wloka, C. & Maglia, G. Single-molecule nanopore enzymology. *Philos. Trans. R. Soc. Lond., B, Biol. Sci.* 372, (2017).
28. Rosen, C. B., Rodriguez-Larrea, D. & Bayley, H. Single-molecule site-specific detection of protein phosphorylation with a nanopore. *Nat Biotechnol* 32, 179-181 (2014).
29. Verschueren, D. V., Jonsson, M. P. & Dekker, C. Temperature dependence of DNA translocations through solid-state nanopores. *Nanotechnology* 26, 234004 (2015).

30. Oukhaled, A. et al. Dynamics of completely unfolded and native proteins through solid-state nanopores as a function of electric driving force. *ACS Nano* 5, 3628-3638 (2011).

31. Yamazaki, H. et al. Label-Free Single-Molecule Thermoscopy Using a Laser-Heated Nanopore. *Nano Lett* 17, 7067-7074 (2017).

32. Song, L. et al. Structure of staphylococcal alpha-hemolysin, a heptameric transmembrane pore. *Science* 274, 1859-1866 (1996).

33. Cressiot, B. et al. Porphyrin-Assisted Docking of a Thermophage Portal Protein into Lipid Bilayers: Nanopore Engineering and Characterization. *ACS Nano* 11, 11931-11945 (2017).

34. Castell, O. K., Berridge, J. & Wallace, M. I. Quantification of membrane protein inhibition by optical ion flux in a droplet interface bilayer array. *Angewandte Chemie International Edition* 51, 3134-3138 (2012).

35. Hall, A. R. et al. Hybrid pore formation by directed insertion of α-haemolysin into solid-state nanopores. *Nature Nanotech* 5, 874-877 (2010).

36. Williams, L. S., Levdikov, V. M., Minakhin, L., Severinov, K. & Antson, A. A. 12-Fold symmetry of the putative portal protein from the *Thermus thermophilus* bacteriophage G20C determined by X-ray analysis. *Acta Crystallogr Sect F Struct Biol Cryst Commun* 69, 1239-1241 (2013).

37. Casjens, S. R. & Gilcrease, E. B. Determining DNA packaging strategy by analysis of the termini of the chromosomes in tailed-bacteriophage virions. *Methods Mol Biol* 502, 91-111 (2009).

38. Lebedev, A. A. et al. Structural framework for DNA translocation via the viral portal protein. *EMBO J* 26, 1984-1994 (2007).

39. Hoogerheide, D. P., Garaj, S. & Golovchenko, J. A. Probing Surface Charge Fluctuations with Solid-State Nanopores. *Physical Review Letters* 102, 256804 (2009).

40. Henrickson, S. E., Misakian, M., Robertson, B. & Kasianowicz, J. J. Driven DNA transport into an asymmetric nanometer-scale pore. *Phys Rev Lett* 85, 3057-3060 (2000).

41. Meller, A. & Branton, D. Single molecule measurements of DNA transport through a nanopore. *Electrophoresis* 23, 2583-2591 (2002).

42. Japrung, D., Henricus, M., Li, Q., Maglia, G. & Bayley, H. Urea Facilitates the Translocation of Single-Stranded DNA and RNA Through the α-Hemolysin Nanopore. *Biophysical Journal* 98, 1856-1863 (2010).

43. Cressiot, B. et al. Dynamics and Energy Contributions for Transport of Unfolded Pertactin through a Protein Nanopore. *ACS Nano* 9, 9050-9061 (2015).

44. Pastoriza-Gallego, M. et al. Dynamics of unfolded protein transport through an aerolysin pore. *J Am Chem Soc* 133, 2923-2931 (2011).

45. Oukhaled, A., Bacri, L., Pastoriza-Gallego, M., Betton, J.-M. & Pelta, J. Sensing proteins through nanopores: fundamental to applications. *ACS Chem Biol* 7, 1935-1949 (2012).

46. Stefureac, R., Long, Y.-T., Kraatz, H.-B., Howard, P. & Lee, J. S. Transport of alpha-helical peptides through alpha-hemolysin and aerolysin pores. *Biochemistry* 45, 9172-9179 (2006).

47. Pastoriza-Gallego, M. et al. Evidence of unfolded protein translocation through a protein nanopore. *ACS Nano* 8, 11350-11360 (2014).

48. Wang, H.-Y., Ying, Y.-L., Li, Y., Kraatz, H.-B. & Long, Y.-T. Nanopore Analysis of β-Amyloid Peptide Aggregation Transition Induced by Small Molecules. *Anal Chem* 83, 1746-1752 (2011).

49. Sutherland, T. C. et al. Structure of peptides investigated by nanopore analysis. *Nano Lett* 4, 1273-1277 (2004).

50. Meng, H. et al. Nanopore analysis of tethered peptides. *J Pept Sci* 16, 701-708 (2010).

51. Mereuta, L. et al. Slowing down single-molecule trafficking through a protein nanopore reveals intermediates for peptide translocation. *Sci Rep* 4, 3885-3885 (2014).

52. Whittingham, J. L., Edwards, D. J., Antson, A. A., Clarkson, J. M. & Dodson, G. G. Interactions of phenol and m-cresol in the insulin hexamer, and their effect on the association properties of B28 pro→Asp insulin analogues. *Biochemistry* 37, 11516-11523 (1998).

53. Kadima, W. et al. The influence of ionic strength and pH on the aggregation properties of zinc-free insulin studied by static and dynamic laser light scattering. *Biopolymers* 33, 1643-1657 (1993).

54. Van Meervelt, V. et al. Real-Time Conformational Changes and Controlled Orientation of Native Proteins Inside a Protein Nanoreactor. *J Am Chem Soc* 139, 18640-18646 (2017).

55. Skinner, G. M., van den Hout, M., Broekmans, O., Dekker, C. & Dekker, N. H. Distinguishing single- and double-stranded nucleic acid molecules using solid-state nanopores. *Nano Lett* 9, 2953-2960 (2009).

56. Lin, J., Fabian, M., Sonenberg, N. & Meller, A. Nanopore detachment kinetics of poly(A) binding proteins from RNA molecules reveals the critical role of C-terminus interactions. *Biophysical Journal* 102, 1427-1434 (2012).

57. Akeson, M., Branton, D., Kasianowicz, J. J., Brandin, E. & Deamer, D. W. Microsecond time-scale discrimination among polycytidylic acid, polyadenylic acid, and polyuridylic acid as homopolymers or as segments within single RNA molecules. *Biophysj* 77, 3227-3233 (1999).

58. Larkin, J. et al. Slow DNA transport through nanopores in hafnium oxide membranes. *ACS Nano* 7, 10121-10128 (2013).

59. Wanunu, M. et al. Rapid electronic detection of probe-specific microRNAs using thin nanopore sensors. *Nature Nanotech* 5, 807-814 (2010).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A protein variant, the protein variant comprising a modification of an amino acid sequence comprising SEQ ID NO: 1, the modification comprising one or more of:

(i) a modification of an upper internal surface residue or a lower internal surface residue of the protein variant, the modification comprising an alteration of an electrostatic surface potential of an upper internal surface or a lower internal surface of SEQ ID NO: 1;

(ii) a modification comprising an insertion of a cysteine residue into SEQ ID NO: 1 or a replacement of an amino acid residue of SEQ ID NO: 1 with a cysteine residue;

(iii) a modification of a tunnel loop residue of the protein variant, the modification comprising an expansion of a narrowest constriction of a tunnel loop of SEQ ID NO: 1, a restriction of the narrowest constriction of the tunnel loop of SEQ ID NO: 1, or a removal of the narrowest constriction of the tunnel loop of SEQ ID NO: 1;

(iv) a modification of a tunnel loop residue of the protein variant, the modification resulting in an alteration of an electrostatic charge property of a tunnel loop of SEQ ID NO: 1;

(v) a modification which alters an external charge of the protein variant;

(vi) a modification which promotes binding of the protein variant to a solid-state matrix;

(vii) a modification which extends an N-terminus or a C-terminus of SEQ ID NO: 1 or an N-terminus or a C-terminus of a cleaved portion of SEQ ID NO: 1; and (viii) a deletion of an amino acid residue of at least one of a C-terminal region and an N-terminal region of SEQ ID NO: 1.

2. The protein variant of claim 1, wherein the modification of SEQ ID NO: 1 comprises a modification of a lower internal surface residue of the protein variant, the modification comprising the alteration of the electrostatic surface potential of the lower internal surface of SEQ ID NO: 1, and wherein the protein variant comprises SEQ ID NO: 27.

3. The protein variant of claim 1, wherein the modification of SEQ ID NO: 1 comprises a replacement of an amino acid residue of SEQ ID NO: 1 with a cysteine residue, and wherein the protein variant comprises SEQ ID NO: 11 or SEQ ID NO: 37.

4. The protein variant of claim 1, wherein the modification of SEQ ID NO: 1 comprises a modification of the tunnel loop residue of the protein variant, the modification comprising the expansion of a narrowest constriction of a tunnel loop of SEQ ID NO: 1, the restriction of the narrowest constriction of the tunnel loop of SEQ ID NO: 1, or the removal of the narrowest constriction of the tunnel loop of SEQ ID NO: 1, and wherein the protein variant comprises one of: SEQ ID NO: 15, SEQ ID NO: 17, SEQ ID NO: 21, SEQ ID NO: 23, and SEQ ID NO: 25.

5. The protein variant of claim 1, wherein the modification of SEQ ID NO: 1 comprises the modification in a tunnel loop residue of the protein variant, the modification resulting in the alteration of the electrostatic charge property of the tunnel loop of SEQ ID NO: 1, and wherein the protein variant comprises SEQ ID NO: 19.

6. The protein variant of claim 1, wherein the modification of SEQ ID NO: 1 comprises the modification which alters the external charge of the protein variant, and wherein the protein variant comprises one of: SEQ ID NO: 9 and SEQ ID NO: 13.

7. The protein variant of claim 1, wherein the modification of SEQ ID NO: 1 comprises the modification which promotes binding of the protein variant to a solid-state matrix, and wherein the protein variant comprises one of: SEQ ID NO: 29, SEQ ID NO: 31 and SEQ ID NO: 35.

8. The protein variant of claim 1, wherein the modification of SEQ ID NO: 1 comprises the modification which extends the N-terminus of the cleaved portion of SEQ ID NO: 1, and wherein the protein variant comprises SEQ ID NO: 33.

9. The protein variant of claim 1, wherein the modification of SEQ ID NO: 1 comprises the deletion of an amino acid residue of at least one of the C-terminal region and the N-terminal region of SEQ ID NO: 1, and wherein the modification comprises a modification of one of: SEQ ID NO: 3, SEQ ID NO: 5 and SEQ ID NO: 7.

10. The protein variant of claim 1, wherein the modification of SEQ ID NO: 1 comprises a modification in one or more of: a wing loop residue, a tunnel loop residue, an upper internal surface residue, a lower internal surface residue, an external surface residue, a C-terminal residue, and an N-terminal residue.

11. A protein variant, the protein variant comprising a modification of an amino acid sequence comprising SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

12. A protein variant, the protein variant comprising a modification of an amino acid sequence comprising SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

13. A protein variant encoded by a modification of a nucleic acid sequence of SEQ ID NO: 2, the modification comprising one or more of:

(i) a modification in a portion of the nucleic acid sequence that encodes an upper internal surface residue or a lower internal surface residue of the protein variant encoded by the nucleic acid sequence, the modification producing an alteration of an electrostatic surface potential of an upper internal surface or a lower internal surface of the protein variant encoded by the nucleic acid sequence;

(ii) a modification comprising an insertion of a cysteine residue into the protein variant encoded by the nucleic acid sequence or a replacement of an amino acid residue of the protein variant encoded by the nucleic acid sequence with a cysteine residue;

(iii) a modification to produce a modification of a tunnel loop residue of the protein variant encoded by the nucleic acid sequence, the modification in the tunnel loop residue comprising an expansion of a narrowest constriction of a tunnel loop of the protein variant encoded by the nucleic acid sequence, a restriction of the narrowest constriction of the tunnel loop of the protein variant encoded by the nucleic acid sequence, or a removal of the narrowest constriction of the tunnel loop of the protein variant encoded by the nucleic acid sequence;

(iv) a modification to produce a modification of a tunnel loop residue of the protein variant encoded by the nucleic acid sequence, the modification resulting in an alteration of an electrostatic charge property of a tunnel loop of the protein variant encoded by the nucleic acid sequence;

(v) a modification which alters an external charge of the protein variant encoded by the nucleic acid sequence;

(vi) a modification which promotes binding of the protein variant encoded by the nucleic acid sequence to a solid-state matrix;

(vii) a modification which extends an N-terminus or a C-terminus of the protein variant encoded by the nucleic acid sequence or an N-terminus or a C-terminus of a cleaved portion of the protein variant encoded by the nucleic acid sequence; and (viii) a deletion of an amino acid residue of at least one of a C-terminal region and an N-terminal region of the protein variant encoded by the nucleic acid sequence.

14. A protein variant encoded by a modification of a nucleic acid sequence of SEQ ID NO: 2, the modification comprising one or more of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

15. A protein variant encoded by a modification of a nucleic acid sequence of SEQ ID NO: 2, the modification comprising one or more of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

* * * * *